(12) United States Patent
Anderson et al.

(10) Patent No.: US 10,058,380 B2
(45) Date of Patent: Aug. 28, 2018

(54) DEVICES AND METHODS FOR MINIMALLY-INVASIVE SURGICAL PROCEDURES

(71) Applicants: Evan R. Anderson, San Francisco, CA (US); Alfredo R. Cantu, Pleasanton, CA (US); Albert K. Chin, Palo Alto, CA (US)

(72) Inventors: Evan R. Anderson, San Francisco, CA (US); Alfredo R. Cantu, Pleasanton, CA (US); Albert K. Chin, Palo Alto, CA (US)

(73) Assignee: MAQUET CORDIOVASCULAR LLC, San Jose, CA (US)

( * ) Notice: Subject to any disclaimer, the term of this patent is extended or adjusted under 35 U.S.C. 154(b) by 568 days.

(21) Appl. No.: 13/779,295

(22) Filed: Feb. 27, 2013

(65) Prior Publication Data

US 2013/0178849 A1    Jul. 11, 2013

Related U.S. Application Data

(63) Continuation of application No. 12/245,246, filed on Oct. 3, 2008, now abandoned.
(Continued)

(51) Int. Cl.
*A61B 18/14* (2006.01)
*A61B 17/00* (2006.01)
(Continued)

(52) U.S. Cl.
CPC ...... *A61B 18/1482* (2013.01); *A61B 17/0057* (2013.01); *A61B 17/3423* (2013.01);
(Continued)

(58) Field of Classification Search
CPC ............ A61B 18/1482; A61B 18/1492; A61B 2018/00577; A61B 2018/00214; A61B 2018/0022
See application file for complete search history.

(56) References Cited

U.S. PATENT DOCUMENTS 3,862,627 A    1/1975   Hans, Sr.
4,316,472 A    2/1982   Mirowski et al.
(Continued)

FOREIGN PATENT DOCUMENTS

EP    1181896 A1    2/2002
EP    1186274 B1    4/2006
(Continued)

OTHER PUBLICATIONS

Argenziano, Surgical Atrial Fibrillation Ablation. http://www.columbiasurgery.org/divisions/cardiac/afib_surg.html. pp. 1-4, downloaded Jan. 13, 2005.
(Continued)

*Primary Examiner* — Bradley J Osinski
(74) *Attorney, Agent, or Firm* — Wesley Scott Ashton

(57) ABSTRACT

Devices, instruments and tools for minimally invasive surgical procedures. Port devices and methods for hemostatically sealing and providing a port through a tissue wall that interfaces with a fluid containing chamber, by minimally invasive techniques. Assemblies, instruments and methods for minimally invasive access to and through a tissue wall that interfaces with a fluid containing chamber, and for visualizing same. Instruments, assemblies and methods for minimally invasive surgical procedures, including ablation.

27 Claims, 24 Drawing Sheets

Related U.S. Application Data

(60) Provisional application No. 60/997,985, filed on Oct. 5, 2007.

(51) Int. Cl.
*A61B 17/34* (2006.01)
*A61B 18/00* (2006.01)

(52) U.S. Cl.
CPC ............. *A61B 18/1492* (2013.01); *A61B 2017/00575* (2013.01); *A61B 2017/00584* (2013.01); *A61B 2017/00597* (2013.01); *A61B 2017/00615* (2013.01); *A61B 2017/00637* (2013.01); *A61B 2017/3425* (2013.01); *A61B 2018/0022* (2013.01); *A61B 2018/00214* (2013.01); *A61B 2018/00232* (2013.01); *A61B 2018/00577* (2013.01)

(56) References Cited

U.S. PATENT DOCUMENTS

| | | |
|---|---|---|
| 4,411,266 A | 10/1983 | Cosman |
| 4,449,528 A | 5/1984 | Auth et al. |
| 4,522,205 A | 6/1985 | Taylor et al. |
| 4,569,801 A | 2/1986 | Molloy et al. |
| 4,641,649 A | 2/1987 | Walinsky et al. |
| 4,660,571 A | 4/1987 | Hess et al. |
| 4,662,368 A | 5/1987 | Hussein et al. |
| 4,669,469 A | 6/1987 | Gifford, III et al. |
| 4,672,962 A | 6/1987 | Hershenson |
| 4,673,563 A | 6/1987 | Berne et al. |
| 4,676,258 A | 6/1987 | Inokuchi et al. |
| 4,699,147 A | 10/1987 | Chilson et al. |
| 4,736,749 A | 4/1988 | Lundback |
| 4,757,820 A | 7/1988 | Itoh |
| 4,762,129 A | 8/1988 | Bonzel |
| 4,784,133 A | 11/1988 | Mackin |
| 4,790,311 A | 12/1988 | Rutz |
| 4,802,475 A | 2/1989 | Weshahy |
| 4,807,620 A | 2/1989 | Strul et al. |
| 4,815,470 A | 3/1989 | Curtis et al. |
| 4,841,977 A | 6/1989 | Griffith et al. |
| 4,872,346 A | 10/1989 | Kelly-Fry et al. |
| 4,882,777 A | 11/1989 | Narula |
| 4,898,591 A | 2/1990 | Jang et al. |
| 4,917,095 A | 4/1990 | Fry et al. |
| 4,924,863 A | 5/1990 | Sterzer |
| 4,936,281 A | 6/1990 | Stasz |
| 4,940,064 A | 7/1990 | Desai |
| 4,945,912 A | 8/1990 | Langberg |
| 4,951,677 A | 8/1990 | Crowley et al. |
| 4,976,711 A | 12/1990 | Parins et al. |
| 4,977,887 A | 12/1990 | Gouda |
| 4,998,933 A | 3/1991 | Eggers et al. |
| 5,000,185 A | 3/1991 | Yock |
| 5,002,059 A | 3/1991 | Crowley et al. |
| 5,035,694 A | 7/1991 | Kasprzyk et al. |
| 5,078,717 A | 1/1992 | Parins et al. |
| 5,078,736 A | 1/1992 | Behl |
| 5,080,102 A | 1/1992 | Dory |
| 5,090,958 A | 2/1992 | Sahota |
| 5,104,393 A | 4/1992 | Isner et al. |
| 5,108,390 A | 4/1992 | Potocky et al. |
| 5,131,397 A | 7/1992 | Crowley |
| 5,147,355 A | 9/1992 | Friedman et al. |
| 5,156,157 A | 10/1992 | Valenta, Jr. et al. |
| 5,171,233 A | 12/1992 | Amplatz et al. |
| 5,178,618 A | 1/1993 | Kandarpa |
| 5,186,177 A | 2/1993 | O'Donnell et al. |
| 5,190,540 A | 3/1993 | Lee |
| 5,195,990 A | 3/1993 | Weldon |
| 5,207,672 A | 5/1993 | Roth et al. |
| 5,209,229 A | 5/1993 | Gilli |
| 5,222,501 A | 6/1993 | Ideker et al. |
| 5,224,943 A | 7/1993 | Goddard |
| 5,226,430 A | 7/1993 | Spears et al. |
| 5,228,442 A | 7/1993 | Imran |
| 5,231,995 A | 8/1993 | Desai |
| 5,246,438 A | 9/1993 | Langberg |
| 5,254,116 A | 10/1993 | Baust et al. |
| 5,255,679 A | 10/1993 | Imran |
| 5,263,493 A | 11/1993 | Avitall |
| 5,269,291 A | 12/1993 | Carter |
| 5,277,201 A | 1/1994 | Stern |
| 5,281,215 A | 1/1994 | Milder |
| 5,292,321 A | 3/1994 | Lee |
| 5,293,868 A | 3/1994 | Nardella |
| 5,293,869 A | 3/1994 | Edwards et al. |
| 5,295,484 A | 3/1994 | Marcus et al. |
| 5,306,234 A | 4/1994 | Johnson |
| 5,313,943 A | 5/1994 | Houser et al. |
| 5,314,466 A | 5/1994 | Stern et al. |
| 5,323,781 A | 6/1994 | Ideker et al. |
| 5,324,184 A | 6/1994 | Morey |
| 5,324,255 A | 6/1994 | Passafaro et al. |
| 5,325,860 A | 7/1994 | Seward et al. |
| 5,331,966 A | 7/1994 | Bennett et al. |
| 5,342,292 A | 8/1994 | Nita et al. |
| 5,344,435 A | 9/1994 | Turner et al. |
| 5,345,936 A | 9/1994 | Pomeranz et al. |
| 5,345,940 A | 9/1994 | Seward et al. |
| 5,348,554 A | 9/1994 | Imran et al. |
| 5,368,035 A | 11/1994 | Hamm et al. |
| 5,368,557 A | 11/1994 | Nita et al. |
| 5,368,558 A | 11/1994 | Nita |
| 5,370,649 A | 12/1994 | Gardetto et al. |
| 5,370,678 A | 12/1994 | Edwards et al. |
| 5,372,138 A | 12/1994 | Crowley et al. |
| 5,385,148 A | 1/1995 | Lesh et al. |
| 5,385,544 A | 1/1995 | Edwards et al. |
| 5,391,197 A | 2/1995 | Burdette et al. |
| 5,405,346 A | 4/1995 | Grundy et al. |
| 5,409,000 A | 4/1995 | Imran |
| 5,411,524 A | 5/1995 | Rahul |
| 5,421,338 A | 6/1995 | Crowley et al. |
| 5,423,808 A | 6/1995 | Edwards et al. |
| 5,423,811 A | 6/1995 | Imran et al. |
| 5,427,119 A | 6/1995 | Swartz et al. |
| 5,433,708 A | 7/1995 | Nichols et al. |
| 5,437,664 A | 8/1995 | Cohen et al. |
| 5,447,509 A | 9/1995 | Mills et al. |
| 5,449,380 A | 9/1995 | Chin |
| 5,454,373 A | 10/1995 | Koger et al. |
| 5,454,807 A | 10/1995 | Lennox et al. |
| 5,456,682 A | 10/1995 | Edwards et al. |
| 5,474,530 A | 12/1995 | Passafaro et al. |
| 5,484,400 A | 1/1996 | Edwards et al. |
| 5,487,385 A | 1/1996 | Avitall |
| 5,487,757 A | 1/1996 | Truckai et al. |
| 5,496,312 A | 3/1996 | Klicek |
| 5,496,346 A | 3/1996 | Horzewski et al. |
| 5,497,119 A | 3/1996 | Tedrow et al. |
| 5,497,774 A | 3/1996 | Swartz et al. |
| 5,500,012 A | 3/1996 | Brucker et al. |
| 5,501,227 A | 3/1996 | Yock |
| 5,505,702 A | 4/1996 | Arney |
| 5,505,730 A | 4/1996 | Edwards |
| 5,509,900 A | 4/1996 | Kirkman |
| 5,520,682 A | 5/1996 | Baust et al. |
| 5,522,872 A | 6/1996 | Hoff |
| 5,522,873 A | 6/1996 | Jackman et al. |
| 5,529,820 A | 6/1996 | Nomi et al. |
| 5,536,267 A | 7/1996 | Edwards et al. |
| 5,545,161 A | 8/1996 | Imran |
| 5,545,193 A | 8/1996 | Fleischman et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,672 A | 9/1996 | Edwards et al. |
| 5,558,720 A | 9/1996 | Sarraf et al. |
| 5,560,362 A | 10/1996 | Sliwa, Jr. et al. |
| 5,562,720 A | 10/1996 | Stern et al. |
| 5,564,440 A | 10/1996 | Swartz et al. |

(56) References Cited

U.S. PATENT DOCUMENTS

| | | | |
|---|---|---|---|
| 5,569,241 A | 10/1996 | Edwards |
| 5,571,088 A | 11/1996 | Lennox et al. |
| 5,571,159 A | 11/1996 | Alt |
| 5,571,215 A | 11/1996 | Sternman et al. |
| 5,575,766 A | 11/1996 | Swartz et al. |
| 5,575,772 A | 11/1996 | Lennox |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,593,404 A | 1/1997 | Costello et al. |
| 5,595,183 A | 1/1997 | Swanson et al. |
| 5,606,974 A | 3/1997 | Castellano et al. |
| 5,607,422 A | 3/1997 | Smeets et al. |
| 5,607,462 A | 3/1997 | Imran |
| 5,609,606 A | 3/1997 | O'Boyle |
| 5,617,854 A | 4/1997 | Munsif |
| 5,620,479 A | 4/1997 | Diederich |
| 5,630,837 A | 5/1997 | Crowley |
| 5,637,090 A | 6/1997 | McGee et al. |
| 5,642,736 A | 7/1997 | Avitall |
| 5,643,197 A | 7/1997 | Brucker et al. |
| 5,645,082 A | 7/1997 | Sung et al. |
| 5,656,029 A | 8/1997 | Imran et al. |
| 5,658,278 A | 8/1997 | Imran et al. |
| 5,666,954 A | 9/1997 | Chapelon et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | LaFontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,683,445 A | 11/1997 | Swoyer |
| 5,685,322 A | 11/1997 | Sung et al. |
| 5,685,839 A | 11/1997 | Edwards et al. |
| 5,685,878 A | 11/1997 | Falwell et al. |
| 5,687,723 A | 11/1997 | Avitall |
| 5,687,729 A | 11/1997 | Schaetzle |
| 5,688,267 A | 11/1997 | Panescu et al. |
| 5,690,611 A | 11/1997 | Swartz et al. |
| 5,693,078 A | 12/1997 | Desai et al. |
| 5,697,925 A | 12/1997 | Taylor |
| 5,697,927 A | 12/1997 | Imran et al. |
| 5,697,928 A | 12/1997 | Walcott et al. |
| 5,702,438 A * | 12/1997 | Avitall .............. A61B 18/1492 600/374 |
| 5,713,942 A | 2/1998 | Stern et al. |
| 5,715,818 A | 2/1998 | Swartz et al. |
| 5,716,389 A | 2/1998 | Walinsky et al. |
| 5,718,231 A | 2/1998 | Dewhurst et al. |
| 5,718,241 A | 2/1998 | Ben-Haim et al. |
| 5,718,701 A | 2/1998 | Shai et al. |
| 5,720,775 A | 2/1998 | Larnard |
| 5,722,401 A | 3/1998 | Pietroski et al. |
| 5,722,403 A | 3/1998 | McGee et al. |
| 5,722,963 A | 3/1998 | Lurie et al. |
| 5,725,494 A | 3/1998 | Brisken |
| 5,725,512 A | 3/1998 | Swartz et al. |
| 5,728,062 A | 3/1998 | Brisken |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,733,315 A | 3/1998 | Burdette et al. |
| 5,735,280 A | 4/1998 | Sherman et al. |
| 5,735,290 A | 4/1998 | Sterman et al. |
| 5,735,811 A | 4/1998 | Brisken |
| 5,735,846 A | 4/1998 | Panescu et al. |
| 5,741,249 A | 4/1998 | Moss et al. |
| 5,741,320 A | 4/1998 | Thornton et al. |
| 5,743,870 A | 4/1998 | Edwards |
| 5,743,903 A | 4/1998 | Stern et al. |
| 5,749,880 A | 5/1998 | Banas et al. |
| 5,755,663 A | 5/1998 | Larsen et al. |
| 5,755,664 A | 5/1998 | Rubenstein |
| 5,755,715 A | 5/1998 | Stern et al. |
| 5,755,760 A | 5/1998 | Maguire et al. |
| 5,769,846 A | 6/1998 | Edwards et al. |
| 5,782,239 A | 7/1998 | Webster, Jr. |
| 5,782,828 A | 7/1998 | Chen et al. |
| 5,782,900 A | 7/1998 | de la Rama et al. |
| 5,785,706 A | 7/1998 | Bednarek |
| RE35,880 E | 8/1998 | Waldman et al. |
| 5,797,877 A | 8/1998 | Hamilton et al. |
| 5,797,903 A | 8/1998 | Swanson et al. |
| 5,797,905 A | 8/1998 | Fleischman et al. |
| 5,797,960 A | 8/1998 | Stevens et al. |
| 5,800,378 A | 9/1998 | Edwards et al. |
| 5,800,379 A | 9/1998 | Edwards |
| 5,800,413 A | 9/1998 | Swartz et al. |
| 5,800,428 A | 9/1998 | Nelson et al. |
| 5,800,429 A | 9/1998 | Edwards |
| 5,800,432 A | 9/1998 | Swanson |
| 5,800,482 A | 9/1998 | Pomeranz et al. |
| 5,800,494 A | 9/1998 | Campbell et al. |
| 5,807,249 A | 9/1998 | Qin et al. |
| 5,807,308 A | 9/1998 | Edwards |
| 5,807,389 A | 9/1998 | Gardetto et al. |
| 5,807,391 A | 9/1998 | Wijkamp |
| 5,807,395 A | 9/1998 | Mulier et al. |
| 5,810,802 A | 9/1998 | Panescu et al. |
| 5,810,803 A | 9/1998 | Moss et al. |
| 5,823,956 A | 10/1998 | Roth et al. |
| 5,824,046 A | 10/1998 | Smith et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,842,984 A | 12/1998 | Avitall |
| 5,844,349 A | 12/1998 | Oakley et al. |
| 5,846,218 A | 12/1998 | Brisken et al. |
| 5,849,028 A | 12/1998 | Chen |
| 5,851,232 A | 12/1998 | Lois |
| 5,853,409 A | 12/1998 | Swanson et al. |
| 5,863,290 A | 1/1999 | Gough et al. |
| 5,871,523 A | 2/1999 | Fleischman et al. |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,882,346 A | 3/1999 | Pomeranz et al. |
| 5,885,278 A | 3/1999 | Fleischman |
| 5,891,134 A | 4/1999 | Goble et al. |
| 5,893,848 A | 4/1999 | Negus et al. |
| 5,895,417 A | 4/1999 | Pomeranz et al. |
| 5,897,554 A | 4/1999 | Chia et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,928,279 A | 7/1999 | Shannon et al. |
| 5,931,810 A | 8/1999 | Grabek |
| 5,931,848 A | 8/1999 | Saadat |
| 5,938,660 A | 8/1999 | Swartz et al. |
| 5,954,661 A | 9/1999 | Greenspon et al. |
| 5,971,980 A | 10/1999 | Sherman |
| 5,971,983 A | 10/1999 | Lesh |
| 5,993,447 A | 11/1999 | Blewett et al. |
| 6,004,269 A | 12/1999 | Crowley et al. |
| 6,006,755 A | 12/1999 | Edwards |
| 6,007,499 A | 12/1999 | Martin et al. |
| 6,012,457 A | 1/2000 | Lesh |
| 6,024,740 A | 2/2000 | Lesh et al. |
| 6,030,379 A | 2/2000 | Panescu et al. |

(56) References Cited

U.S. PATENT DOCUMENTS

| | | | |
|---|---|---|---|
| 6,036,689 A * | 3/2000 | Tu | A61B 18/1492 604/103.08 |
| 6,042,556 A | 3/2000 | Beach et al. | |
| 6,053,912 A | 4/2000 | Panescu et al. | |
| 6,056,745 A | 5/2000 | Panescu et al. | |
| 6,064,902 A | 5/2000 | Haissaguerre et al. | |
| 6,071,279 A | 6/2000 | Whayne et al. | |
| 6,071,281 A | 6/2000 | Burnside et al. | |
| 6,076,012 A | 6/2000 | Swanson et al. | |
| 6,088,894 A | 7/2000 | Oakley et al. | |
| 6,113,592 A | 9/2000 | Taylor | |
| 6,117,101 A | 9/2000 | Diederich et al. | |
| 6,120,434 A | 9/2000 | Kimura et al. | |
| 6,120,496 A | 9/2000 | Whayne et al. | |
| 6,126,682 A | 10/2000 | Sharkey | |
| 6,138,043 A | 10/2000 | Avitall | |
| 6,142,994 A | 11/2000 | Swanson et al. | |
| 6,152,144 A | 11/2000 | Lesh et al. | |
| 6,152,920 A | 11/2000 | Thompson et al. | |
| 6,161,543 A | 12/2000 | Cox et al. | |
| 6,179,835 B1 | 1/2001 | Panescu et al. | |
| 6,217,528 B1 | 4/2001 | Koblish et al. | |
| 6,217,576 B1 | 4/2001 | Tu et al. | |
| 6,231,518 B1 | 5/2001 | Grabek et al. | |
| 6,233,490 B1 | 5/2001 | Kasevich | |
| 6,237,605 B1 | 5/2001 | Vaska et al. | |
| 6,238,347 B1 | 5/2001 | Nix et al. | |
| 6,241,754 B1 | 6/2001 | Swanson et al. | |
| 6,245,062 B1 | 6/2001 | Berube et al. | |
| 6,245,064 B1 | 6/2001 | Lesh et al. | |
| 6,245,065 B1 | 6/2001 | Panescu et al. | |
| 6,251,109 B1 | 6/2001 | Hassett et al. | |
| 6,254,599 B1 | 7/2001 | Lesh et al. | |
| 6,264,670 B1 | 7/2001 | Chin | |
| 6,270,471 B1 | 8/2001 | Hechel et al. | |
| 6,277,113 B1 | 8/2001 | Berube | |
| 6,283,919 B1 | 9/2001 | Roundhill et al. | |
| 6,293,943 B1 | 9/2001 | Panescu et al. | |
| 6,296,619 B1 | 10/2001 | Brisken et al. | |
| 6,302,880 B1 | 10/2001 | Schaer | |
| 6,308,091 B1 | 10/2001 | Avitall | |
| 6,311,692 B1 | 11/2001 | Vaska et al. | |
| 6,312,383 B1 | 11/2001 | Lizzi et al. | |
| 6,312,427 B1 | 11/2001 | Berube et al. | |
| 6,314,962 B1 | 11/2001 | Vaska et al. | |
| 6,314,963 B1 | 11/2001 | Vaska et al. | |
| 6,325,796 B1 | 12/2001 | Berube et al. | |
| 6,325,797 B1 | 12/2001 | Stewart et al. | |
| 6,331,158 B1 | 12/2001 | Hu et al. | |
| 6,332,881 B1 | 12/2001 | Carner et al. | |
| 6,361,531 B1 | 3/2002 | Hissong | |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,375,654 B1 | 4/2002 | McIntyre | |
| 6,383,151 B1 | 5/2002 | Diederich et al. | |
| 6,383,182 B1 | 5/2002 | Berube et al. | |
| 6,385,472 B1 | 5/2002 | Hall et al. | |
| 6,387,043 B1 | 5/2002 | Yoon | |
| 6,398,792 B1 | 6/2002 | O'Connor | |
| 6,413,254 B1 | 7/2002 | Hissong et al. | |
| 6,419,648 B1 | 7/2002 | Vitek et al. | |
| 6,421,556 B2 | 7/2002 | Swanson | |
| 6,425,867 B1 | 7/2002 | Vaezy et al. | |
| 6,428,536 B2 | 8/2002 | Panescu et al. | |
| 6,428,537 B1 | 8/2002 | Swanson et al. | |
| 6,428,556 B1 | 8/2002 | Chin | |
| 6,430,426 B2 | 8/2002 | Avitall | |
| 6,447,507 B1 | 9/2002 | Bednarek et al. | |
| 6,461,314 B1 | 10/2002 | Pant et al. | |
| 6,461,956 B1 | 10/2002 | Hsuan et al. | |
| 6,464,700 B1 | 10/2002 | Koblish et al. | |
| 6,471,696 B1 | 10/2002 | Berube et al. | |
| 6,471,697 B1 | 10/2002 | Lesh | |
| 6,471,698 B1 | 10/2002 | Edwards et al. | |
| 6,474,340 B1 | 11/2002 | Vaska et al. | |
| 6,475,179 B1 | 11/2002 | Wang et al. | |
| 6,477,396 B1 | 11/2002 | Mest et al. | |
| 6,484,727 B1 | 11/2002 | Vaska et al. | |
| 6,488,679 B1 | 12/2002 | Swanson et al. | |
| 6,488,680 B1 | 12/2002 | Francischelli et al. | |
| 6,500,174 B1 | 12/2002 | Maguire et al. | |
| 6,514,249 B1 | 2/2003 | Maguire et al. | |
| 6,517,536 B2 | 2/2003 | Hooven et al. | |
| 6,522,930 B1 | 2/2003 | Schaer et al. | |
| 6,527,767 B2 | 3/2003 | Wang et al. | |
| 6,527,768 B2 | 3/2003 | Berube | |
| 6,527,769 B2 | 3/2003 | Langberg et al. | |
| 6,529,756 B1 | 3/2003 | Phan et al. | |
| 6,542,781 B1 | 4/2003 | Koblish et al. | |
| 6,546,935 B2 | 4/2003 | Hooven | |
| 6,547,788 B1 | 4/2003 | Maguire et al. | |
| 6,551,303 B1 | 4/2003 | Van Tassel et al. | |
| 6,558,375 B1 | 5/2003 | Sinofsky et al. | |
| 6,569,082 B1 | 5/2003 | Chin | |
| 6,572,612 B2 | 6/2003 | Stewart et al. | |
| 6,582,425 B2 | 6/2003 | Simpson | |
| 6,589,214 B2 | 7/2003 | McGuckin, Jr. et al. | |
| 6,595,989 B1 | 7/2003 | Schaer | |
| 6,599,288 B2 | 7/2003 | Maguire et al. | |
| 6,607,502 B1 | 8/2003 | Maguire et al. | |
| 6,607,520 B2 | 8/2003 | Keane | |
| 6,610,055 B1 | 8/2003 | Swanson et al. | |
| 6,626,830 B1 | 9/2003 | Califiore et al. | |
| 6,635,054 B2 | 10/2003 | Fjield et al. | |
| 6,645,199 B1 | 11/2003 | Jenkins et al. | |
| 6,645,202 B1 | 11/2003 | Pless et al. | |
| 6,652,515 B1 | 11/2003 | Maguire et al. | |
| 6,652,518 B2 | 11/2003 | Wellman et al. | |
| 6,666,858 B2 | 12/2003 | Lafontaine | |
| 6,673,068 B1 | 1/2004 | Berube | |
| 6,679,269 B2 | 1/2004 | Swanson | |
| 6,689,128 B2 | 2/2004 | Sliwa, Jr. et al. | |
| 6,696,844 B2 | 2/2004 | Wong et al. | |
| 6,701,931 B2 | 3/2004 | Sliwa, Jr. et al. | |
| 6,706,052 B1 * | 3/2004 | Chin | A61B 17/00008 606/198 |
| 6,719,755 B2 | 4/2004 | Sliwa, Jr. et al. | |
| 6,723,092 B2 | 4/2004 | Brown et al. | |
| 6,728,563 B2 | 4/2004 | Rashidi | |
| 6,802,840 B2 | 10/2004 | Chin et al. | |
| 6,817,999 B2 | 11/2004 | Berube et al. | |
| 6,823,218 B2 | 11/2004 | Berube | |
| 6,849,075 B2 | 2/2005 | Bertolero et al. | |
| 6,885,632 B1 | 4/2005 | Mattson | |
| 6,904,303 B2 | 6/2005 | Phan et al. | |
| 6,926,662 B1 | 8/2005 | Aboul-Hosn et al. | |
| 6,962,586 B2 | 11/2005 | Berube et al. | |
| 7,033,352 B1 | 4/2006 | Gauthier et al. | |
| 7,226,446 B1 | 6/2007 | Mody et al. | |
| 7,255,695 B2 | 8/2007 | Falwell et al. | |
| 7,708,753 B2 * | 5/2010 | Hardert | A61M 25/104 606/128 |
| 7,721,742 B2 | 5/2010 | Kalloo et al. | |
| 7,860,555 B2 | 12/2010 | Saadat | |
| 7,860,556 B2 | 12/2010 | Saadat | |
| 7,918,787 B2 | 4/2011 | Saadat | |
| 7,930,016 B1 | 4/2011 | Saadat | |
| 2001/0007940 A1 | 7/2001 | Tu et al. | |
| 2001/0025174 A1 | 9/2001 | Daniel et al. | |
| 2001/0031961 A1 | 10/2001 | Hooven | |
| 2002/0017306 A1 | 2/2002 | Cox et al. | |
| 2002/0022839 A1 | 2/2002 | Stewart et al. | |
| 2002/0032440 A1 | 3/2002 | Hooven et al. | |
| 2002/0068924 A1 | 6/2002 | Sinofsky | |
| 2002/0068970 A1 | 6/2002 | Cox et al. | |
| 2002/0087151 A1 | 7/2002 | Mody et al. | |
| 2002/0087208 A1 | 7/2002 | Koblish et al. | |
| 2002/0091382 A1 | 7/2002 | Hooven | |
| 2002/0091383 A1 | 7/2002 | Hooven | |
| 2002/0091384 A1 | 7/2002 | Hooven et al. | |
| 2002/0103484 A1 | 8/2002 | Hooven | |
| 2002/0107513 A1 | 8/2002 | Hooven | |
| 2002/0107514 A1 | 8/2002 | Hooven | |

(56) References Cited

U.S. PATENT DOCUMENTS

| | | |
|---|---|---|
| 2002/0115993 A1 | 8/2002 | Hooven |
| 2002/0120316 A1 | 8/2002 | Hooven et al. |
| 2002/0128636 A1 | 9/2002 | Chin et al. |
| 2002/0143326 A1 | 10/2002 | Foley et al. |
| 2002/0183738 A1 | 12/2002 | Chee et al. |
| 2003/0018329 A1 | 1/2003 | Hooven |
| 2003/0024537 A1 | 2/2003 | Cox et al. |
| 2003/0029462 A1 | 2/2003 | Cox et al. |
| 2003/0032952 A1 | 2/2003 | Hooven |
| 2003/0065318 A1 | 4/2003 | Pendekanti |
| 2003/0065319 A1 | 4/2003 | Wellman |
| 2003/0065320 A1 | 4/2003 | Wellman et al. |
| 2003/0069572 A1 | 4/2003 | Wellman et al. |
| 2003/0069575 A1 | 4/2003 | Chin et al. |
| 2003/0083654 A1 | 5/2003 | Chin et al. |
| 2003/0093068 A1 | 5/2003 | Hooven |
| 2003/0109868 A1 | 6/2003 | Chin et al. |
| 2003/0125729 A1 | 7/2003 | Hooven et al. |
| 2003/0163128 A1 | 8/2003 | Patil et al. |
| 2003/0187460 A1 | 10/2003 | Chin et al. |
| 2003/0187461 A1 | 10/2003 | Chin |
| 2003/0199867 A1 | 10/2003 | Wellman |
| 2004/0102804 A1 | 5/2004 | Chin |
| 2004/0106918 A1 | 6/2004 | Cox et al. |
| 2004/0106937 A1 | 6/2004 | Berube et al. |
| 2004/0111101 A1 | 6/2004 | Chin |
| 2004/0138526 A1 | 7/2004 | Guenst |
| 2004/0216748 A1 | 11/2004 | Chin |
| 2004/0267303 A1 | 12/2004 | Guenst |
| 2005/0010201 A1 | 1/2005 | Abboud et al. |
| 2005/0075629 A1 | 4/2005 | Chapelon et al. |
| 2005/0107668 A1 | 5/2005 | Smith |
| 2005/0165432 A1 | 7/2005 | Heinrich |
| 2006/0184048 A1 | 8/2006 | Saadat |
| 2006/0270900 A1 | 11/2006 | Chin et al. |
| 2006/0271032 A1 | 11/2006 | Chin et al. |
| 2007/0129719 A1 | 6/2007 | Kendale et al. |
| 2007/0167828 A1 | 7/2007 | Saadat |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0015445 A1 | 1/2008 | Saadat et al. |
| 2008/0015569 A1 | 1/2008 | Saadat et al. |
| 2008/0033290 A1 | 2/2008 | Saadat et al. |
| 2008/0058591 A1 | 3/2008 | Saadat et al. |
| 2008/0058650 A1 | 3/2008 | Saadat et al. |
| 2008/0097476 A1 | 4/2008 | Peh et al. |
| 2008/0183036 A1 | 7/2008 | Saadat et al. |
| 2008/0188759 A1 | 8/2008 | Saadat et al. |
| 2008/0214889 A1 | 9/2008 | Saadat et al. |
| 2008/0275300 A1 | 11/2008 | Rothe et al. |
| 2008/0281293 A1 | 11/2008 | Peh et al. |
| 2009/0030276 A1 | 1/2009 | Saadat et al. |
| 2009/0062790 A1 | 3/2009 | Malchano et al. |
| 2009/0076498 A1 | 3/2009 | Saadat et al. |
| 2009/0125022 A1 | 5/2009 | Saadat et al. |
| 2009/0143640 A1 | 6/2009 | Saadat et al. |
| 2009/0221871 A1 | 9/2009 | Peh et al. |
| 2009/0227999 A1 | 9/2009 | Willis et al. |
| 2009/0275799 A1 | 11/2009 | Saadat et al. |
| 2010/0004506 A1 | 1/2010 | Saadat |
| 2011/0060227 A1 | 3/2011 | Saadat |
| 2011/0060298 A1 | 3/2011 | Saadat |
| 2016/0374754 A1* | 12/2016 | Asirvatham ............ A61B 18/02 606/41 |

FOREIGN PATENT DOCUMENTS

| | | |
|---|---|---|
| GB | 2094636 A | 9/1982 |
| GB | 2289510 A | 11/1995 |
| JP | 11-216189 A | 8/2011 |
| WO | 1993020770 A2 | 10/1993 |
| WO | 1993020886 A1 | 10/1993 |
| WO | 1994000050 A1 | 1/1994 |
| WO | 1994021167 A1 | 9/1994 |
| WO | 1994021168 A1 | 9/1994 |
| WO | 1994021665 A1 | 9/1994 |
| WO | 1995010318 A1 | 4/1995 |
| WO | 1995010319 A1 | 4/1995 |
| WO | 1995010321 A1 | 4/1995 |
| WO | 1995010978 A1 | 4/1995 |
| WO | 1995015115 A1 | 6/1995 |
| WO | 1995017222 A1 | 6/1995 |
| WO | 1995019738 A1 | 7/1995 |
| WO | 1995030380 A2 | 11/1995 |
| WO | 1996000036 A1 | 1/1996 |
| WO | 1996010961 A1 | 4/1996 |
| WO | 1996026675 A1 | 9/1996 |
| WO | 1996032885 A1 | 10/1996 |
| WO | 1996032897 A1 | 10/1996 |
| WO | 1996035469 A1 | 11/1996 |
| WO | 1996039966 A1 | 12/1996 |
| WO | 1997006727 A1 | 2/1997 |
| WO | 1997017904 A1 | 5/1997 |
| WO | 1997018853 A1 | 5/1997 |
| WO | 1997025916 A1 | 7/1997 |
| WO | 1997025918 A1 | 7/1997 |
| WO | 1997025919 A1 | 7/1997 |
| WO | 1997032525 A1 | 9/1997 |
| WO | 1997033526 A2 | 9/1997 |
| WO | 1997037607 A2 | 10/1997 |
| WO | 1997041793 A1 | 11/1997 |
| WO | 1997043970 A1 | 11/1997 |
| WO | 1997045156 A2 | 12/1997 |
| WO | 1998002201 A1 | 1/1998 |
| WO | 1998017187 A1 | 4/1998 |
| WO | 1998024488 A2 | 6/1998 |
| WO | 1998026724 A1 | 6/1998 |
| WO | 1998037822 A1 | 9/1998 |
| WO | 1998048881 A1 | 11/1998 |
| WO | 1998049957 A1 | 11/1998 |
| WO | 1998052465 A1 | 11/1998 |
| WO | 1999000064 A1 | 1/1999 |
| WO | 1999002096 A1 | 1/1999 |
| WO | 1999004696 A1 | 2/1999 |
| WO | 1999048421 A1 | 9/1999 |
| WO | 1999049788 A1 | 10/1999 |
| WO | 1999056812 A2 | 11/1999 |
| WO | 1999059486 A2 | 11/1999 |
| WO | 2000045706 A1 | 8/2000 |
| WO | 2000057495 A1 | 9/2000 |
| WO | 2001003594 A1 | 1/2001 |
| WO | 2001005305 A1 | 1/2001 |
| WO | 2001028623 A2 | 4/2001 |
| WO | 2001045550 A2 | 6/2001 |
| WO | 2001066189 A1 | 9/2001 |
| WO | 2001070112 A1 | 9/2001 |
| WO | 2001072234 A1 | 10/2001 |
| WO | 2001072373 A2 | 10/2001 |
| WO | 2001082778 A2 | 11/2001 |
| WO | 2002005720 A1 | 1/2002 |
| WO | 2002005722 A1 | 1/2002 |
| WO | 2002005868 A2 | 1/2002 |
| WO | 2002007774 A2 | 1/2002 |
| WO | 2002009610 A1 | 2/2002 |
| WO | 2002021995 A2 | 3/2002 |
| WO | 2002024050 A2 | 3/2002 |
| WO | 2002026142 A1 | 4/2002 |
| WO | 2002030310 A1 | 4/2002 |
| WO | 2002040093 A2 | 5/2002 |
| WO | 2002045608 A2 | 6/2002 |
| WO | 2003053259 A2 | 7/2003 |
| WO | 2004028233 A2 | 4/2004 |
| WO | 2006127238 A2 | 11/2006 |
| WO | 2006127241 A2 | 11/2006 |

OTHER PUBLICATIONS

Balkhy et al. "Minimally Invasive Atrial Fibrillation Ablation Combined with a New Technique for Thoracoscopic Stapling of the Left Atrial Appendage: Case Report" pp. 1-2, http://www.hsforum.com/vol7/issue6/2004.html, 2004.

(56) References Cited

OTHER PUBLICATIONS

Benussi et al. "Surgical Ablation of Trial Fibrillation Using the Epicardial Radiofrequency Approach: Mid-Term Results and Risk Analysis" Ann Thorac Surg 74:1050-57 (2002).
Bernhard "Cardiovascular Endoscopy: Historical Perspectives" Endovascular Surgery, W.B. Saunders Co., pp. 13-30 (1989).
Chen et al. "Specialized Conductive Cells in Human Pulmonary Veins: Facts and Controversy" J. Cardiovasc Electrophysiol. 14:810-11 (Aug. 2003).
Chen et al. "Initiation of Atrial Fibrillation by Ectopic Beats Originating From the Pulmonary Veins" Circulation 100:1879-86 (1999).
Cox et al. "Current Status of the Maze Procedure for the Treatment of Atrial Fibrillation" Seminars in Thoracic and Cardiovascular Surgery 12(1):15-19 (Jan. 2000).
Cox et al. "The Surgical Treatment of Atrial Fibrillation—II. Intraoperative electrophysiologic mapping and description of the electrophysiologic basis of atrial flutter and atrial fibrillation" J. Thorac Cardiovasc Surg. 101:406-26 (1991).
Cox et al. "The Surgical Treatment of Atrial Fibrillation—III. Development of a definitive surgical procedure" J. Thorac Cardiovasc Surg. 101(4):569:83 (1991).
Dill et al. "Pulmonary Vein Diameter Reduction After Radiofrequency Catheter Ablation for Paroxysmal Atrial Fibrillation Evaluated by Contrast-Enhanced Three Dimensional Magnetic Resonance Imaging" Circulation 107:846-50 (2007).
Fuster and Rydén et al. "ACC/AHA/ESC Executive Summary" JACC 38(4):1234-36 (Oct. 2001).
Gaita et al. "Atrial Mapping and Radiofrequency Catheter Ablation in Patients with Idiopathic Atrial Fibrillation" Circulation 97:2136-45 (1998).
Gillinov et al. "Atrial Fibrillation: Current Surgical Options and Their Assessment" Ann Thorc Surg 74:2210-17 (2002).
Gillinov et al. "Atricure Bipolar Radiofrequency Clamp for Intraoperative Ablation of Atrial Fibrillation" Ann Thorac Surg. 74:2165-68 (2002).
Gillinov et al. "Microwave Ablation of Atrial Fibrillation During Mitral Valve Operations" Ann. Thorac. Surg. 74:1259-61 (2002).
Güden et al. "Intraoperative Saline-Irrigated Radiofrequency Modified Maze Procedure for Atrial Fibrillation" Ann Thorac Surg 74:S1301-6 (2002).
Hammer et al. "Irrigated Bipolar Radiofrequency Ablation with Transmurality Feedback for the Surgical Cox-Maze Procedure" The Heart Surgery Forum, #2003-11770, 6(5):418-23, (2003).
Haïssaguerre et al. "Electrophysiological Breakthroughs from the Left Atrium to the Pulmonary Veins" Circulation 102:2463-2465 (2000).
Haïssaguerre et al. "Spontaneous Initiation of Atrial Fibrillation by Ectopic Beats Originating in the Pulmonary Veins" The New England Journal of Medicine, 339(10):659-666 (1998).
Hornero et al. "Biatrial Radiofrequency Ablation for Atrial Fibrillation: Epicardial and Endocardial Surgical Approach" Interactive Cardiovascular and Thoracic Surgery 1:72-77 (2002).
Kamohara et al. "A novel device for left atrial appendage exclusion" The Journal of Thoracic and Cardiovascular Surgery 130(6):1639-44 (2005).
Keane et al. "Pulmonary Vein Isolation for Atrial Fibrillation" Rev Cardiovasc Med. 3(4) 167-75 (2002).
Keane et al. Linear Atrial Ablation with a Diode Laser and Fibberoptic Catheter Circulation (1999) 100:e59-60) Available at http://www.circulationaha.org.
Kress et al. "Validation of a Left Atrial Lesion Pattern for Intraoperative Ablation of Atrial Fibrillation" Ann Thorac Surg. (2002) 73:1160-8.
Kondo et al. "Left Atrial Maze Procedure: A Useful Addition to Other Corrective Operations" Ann Thorac Surg. (2003) 75:1490-4.
Lévy et al. "International Consensus on Nomenclature and Classification of Atrial Fibrillation: A Collaborative Project of the Working Group on Arrhythmias and the Working Group of Cardiac Pacing of the European Society of Cardiology and the North American Society of Pacing and Electrophysiology" J. Cardiovascular Electrophysiology (Apr. 2003) 14(4):443-5.
Lin et al. "Pulmonary Vein Morphology in Patients with Paroxysmal Atril Fibrillation Initiated by Ectopic Beats Originating from the Pulmonary Veins" Circulation (2000) 101:1274-81.
Maessen et al. "Beating-Heart Surgical Treatment of Atrial Fibrillation with Microwave Ablation" Ann Thorac Surg. (2002) 74:S1307-11.
Melo et al. "Endocardial and Epicardial Radiofrequency Ablation in the Treatment of Atrial Fibrillation with a New Intra-Opertative Device" Eur J Cardio-thoracic Surg. (2000) 18:182-6.
Mitchell et al. "Linear Atrial Ablations in a Canine Model of Chronic Atrial Fibrillation—Morphological and Electrophysiological Observations" Circulation (1998) 97:1176-85.
Mohr et al. "Curvative Treatment of Atrial Fibrillation with Intraoperative Radiofrequency Ablation: Short-term and midterm results" J. Thoracic & Cardiovasc Sug.(2002)123(5):919-27.
National Institute for Clinical Excellence, Interventional Procedures Programme (Jul. 2004) pp. 1-12.
Natale et al. "First Human Experience with Pulmonary Vein Isolation Using a Through-the-Balloon Circumferential Ultrasound Ablation System for Recurrent Atrial Fibrillation" Circulation (2000) 102:1879-82.
Organ "Electrophysiologic Principles of Radiofrequency Lesion Making" Appl. Appl. Neurophysiol. (1976/77) 39:69-76.
Pasic et al. "Intraoperative Radiofrequency Maze Ablation for Atrial Fibrillation: The Berlin Modification" Ann Thorac Surg. (2001) 72:1484-91.
Saltman et al. "A Completely Endoscopic Approach to Microwave Ablation for Atrial Fibrillation" The Heart Surgery Forum (2003) #2003-11333, 6(3). Available at www.hsforum.com/vol6/issue3/2003-11333.html.
Saltman "Microwave Ablation—A New Use in an Old Technology" Business Briefing: US Cardiology (2004) pp. 1-8.
Song et al. "Recent Advances in Surgery for Atrial Fibrillation" Atrial Fibrillation Special Report webpage (Nov. 2004) pp. 1-12.
Stabile et al. "Is Pulmonary Vein Isolation Necessary for Curing Atrial Fibrillation?" Circulation (2003) 108:657.
Sueda et al. "Efficacy of Pulmonary Vein Isolation for the Elimination of Chronic Atrial Fibrillation in Cardiac Valvular Surgery" Ann Thorac Surg. (2001)71:1189-93.
Thomas et al. "Comparision of Epicardial and Endocardial Linear Ablation Using Handheld Probes" Ann Thorac Surg. (Feb. 2003) 75(2):543-8 (abstract).
Williams et al. "Application of Microwave Energy in Cardiac Tissue Ablation: From in Vitro Analyses to Clinical Use" Ann Thorac. Surg. (2002) 74:1500-5.
Williams et al. "Surgical Treatment of Atrial Fibrillation Using Radiofrequency Energy" Ann Thorac Surg. (2001) 71:1939-44.
International Search Report and Written Opinion for PCT/US08/10657 dated Nov. 19, 2008.
W. Gorisch et al., Heat-induced contraction of blood vessels, 2 Lasers Surg Med. 1-13 (1982), abstract only (Exhibit C1).
A. D'Avila et al., Effects of radiofrequency pulses delivered in the vicinity of the coronary arteries: implications for nonsurgical transthoracic epicardial catheter ablation to treat ventricular tachycardia, 25 Pacing Clin Electrophysiol 1488-95 (2002), abstract only (Exhibit D1).
P. Chatelain, Acute coronary occlusion secondary to radiofrequency catheter ablation of a left lateral accessory pathway, 16 Eur Heart J 859-61 (1995), abstract only (Exhibit E1).
S. Ouali et al., Acute coronary occlusion during radiofrequency catheter ablation of typical atrial flutter, 13 J Cardiovasc Electrophysiol. 1047-9 (2002), abstract only (Exhibit F1).
T. Paul et al., Complete occlusion of the left circumflex coronary artery after radiofrequency catheter ablation in an infant, 14 J Cardiovasc Electrophysiol. 1004-6 (2003), abstract only (Exhibit G1).
H. Bertram et al., Coronary artery stenosis after radiofrequency catheter ablation of accessory atrioventricular pathways in children

(56) References Cited

OTHER PUBLICATIONS with Ebstein's malformation, 103 Circulation 538-43 (2001), abstract only (Exhibit H1).

* cited by examiner

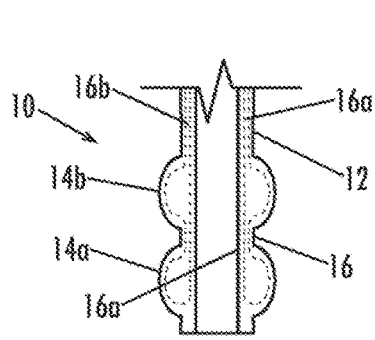
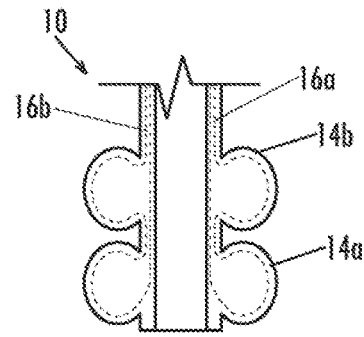
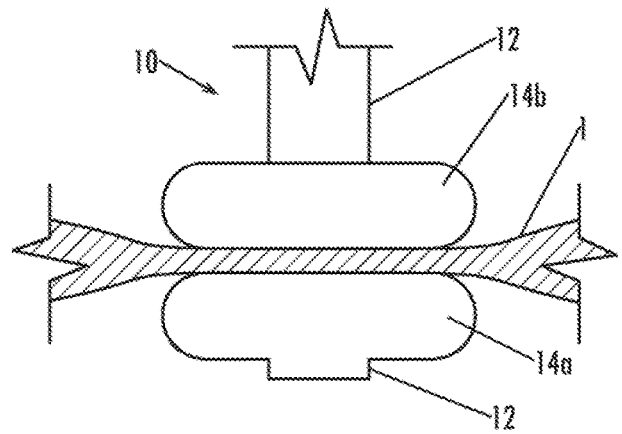
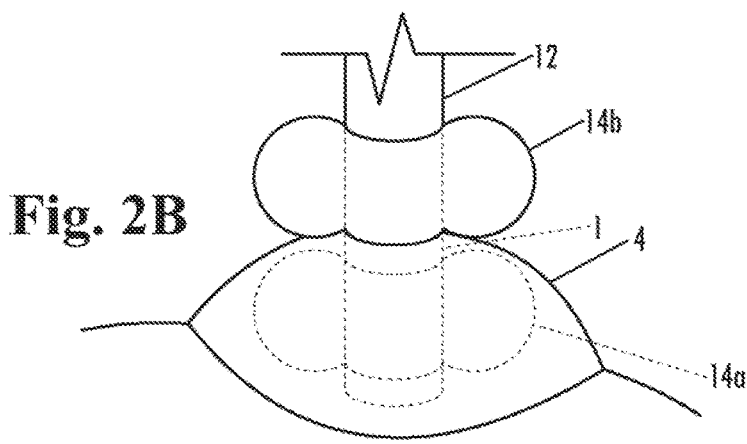

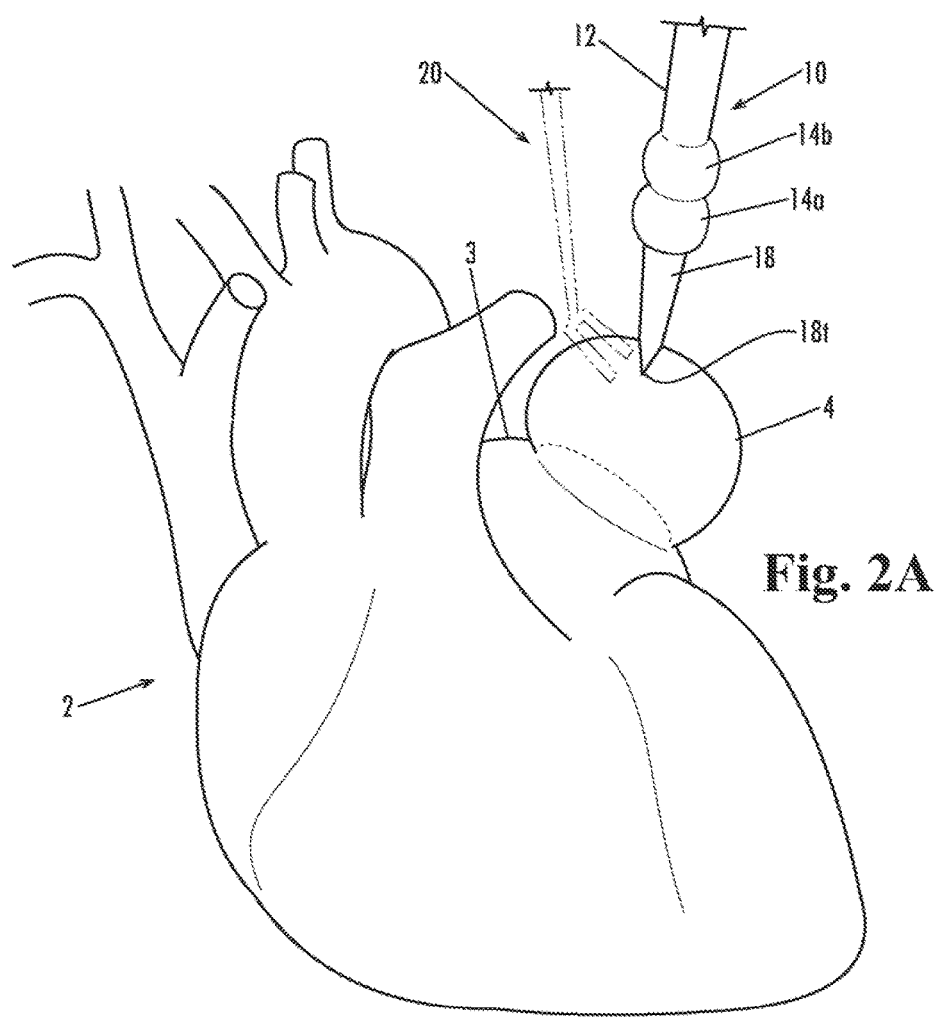
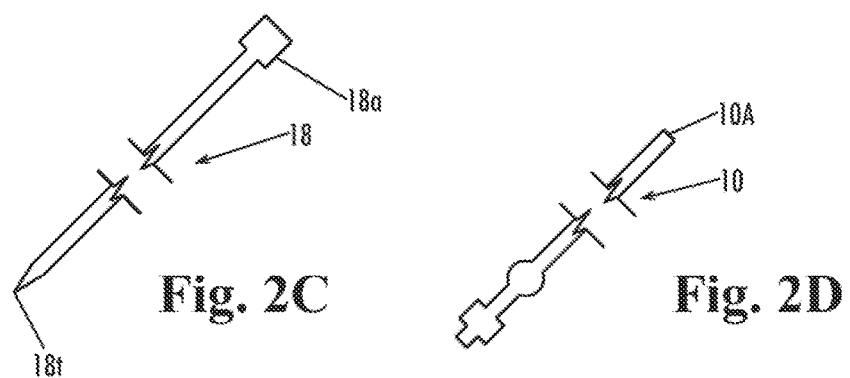

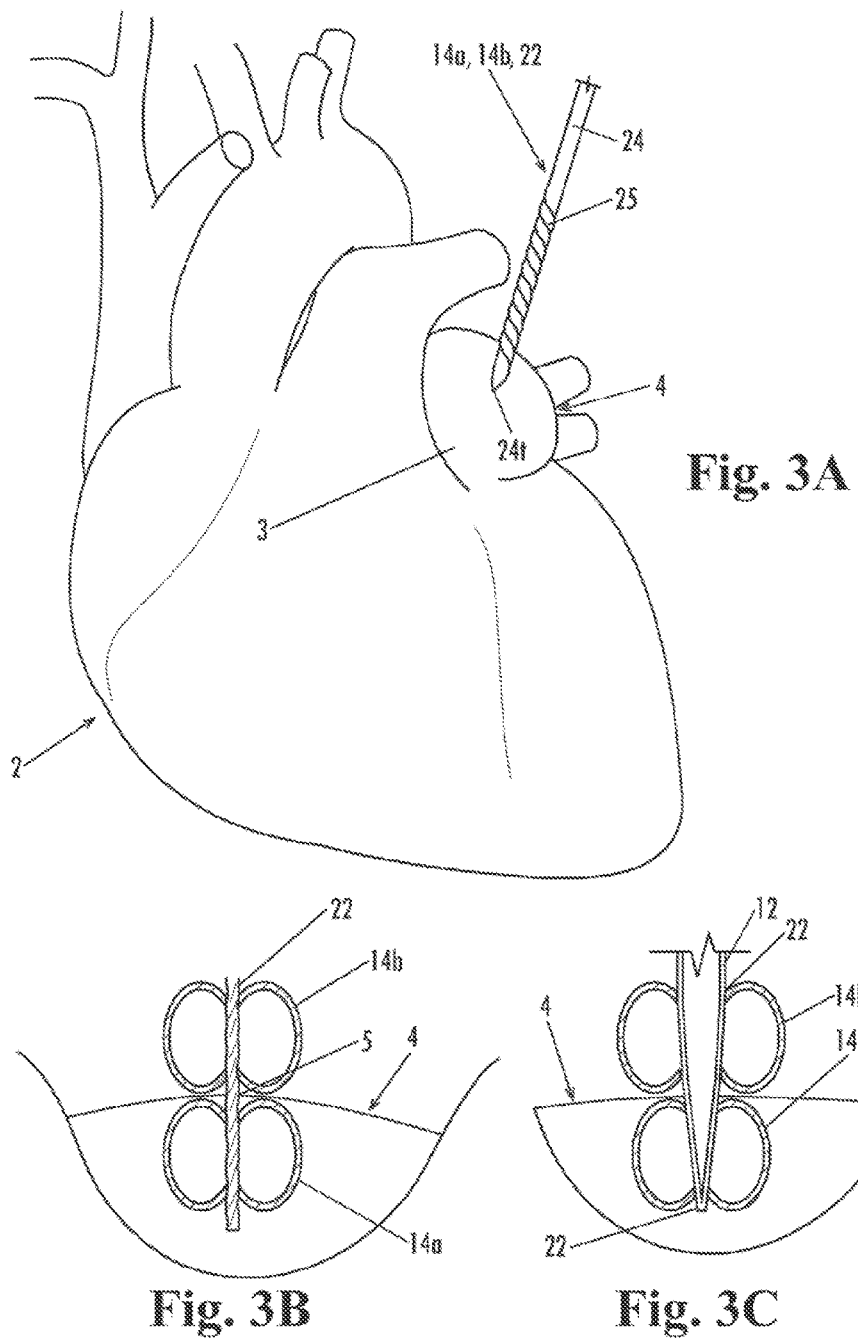

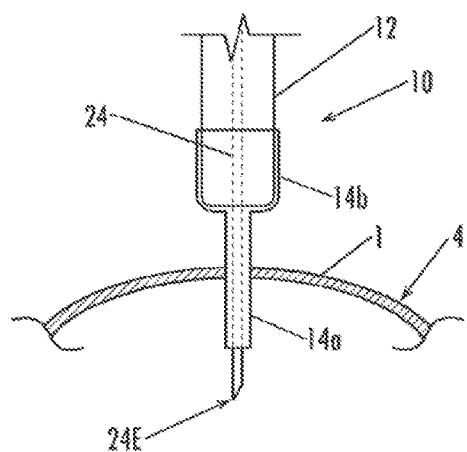
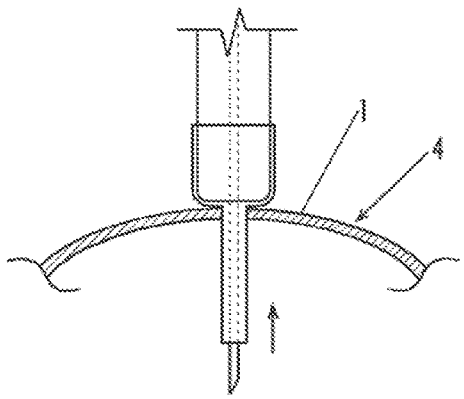
Fig. 4A    Fig. 4B
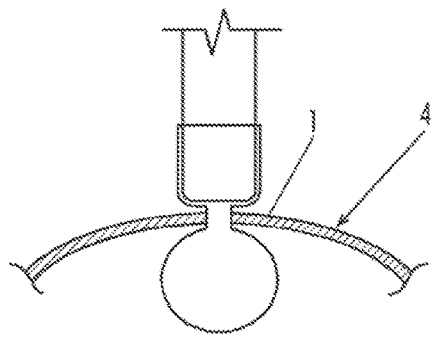
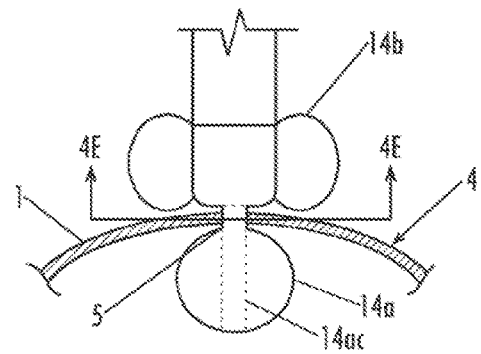
Fig. 4C    Fig. 4D
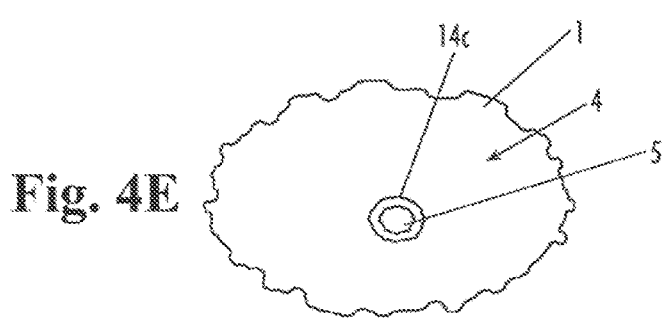
Fig. 4E

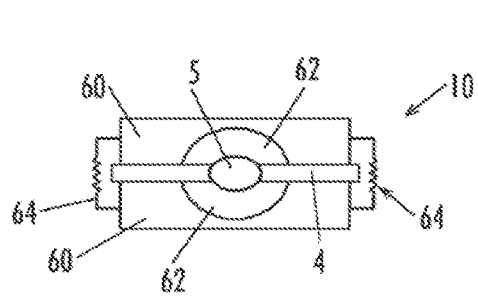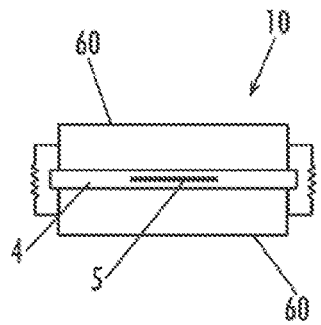
Fig. 8A  Fig. 8B
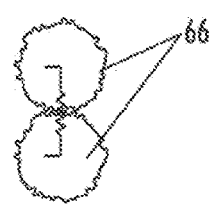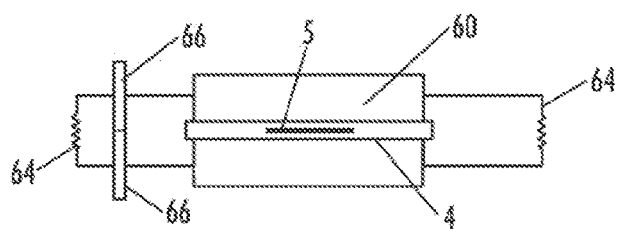
Fig. 8C  Fig. 8D
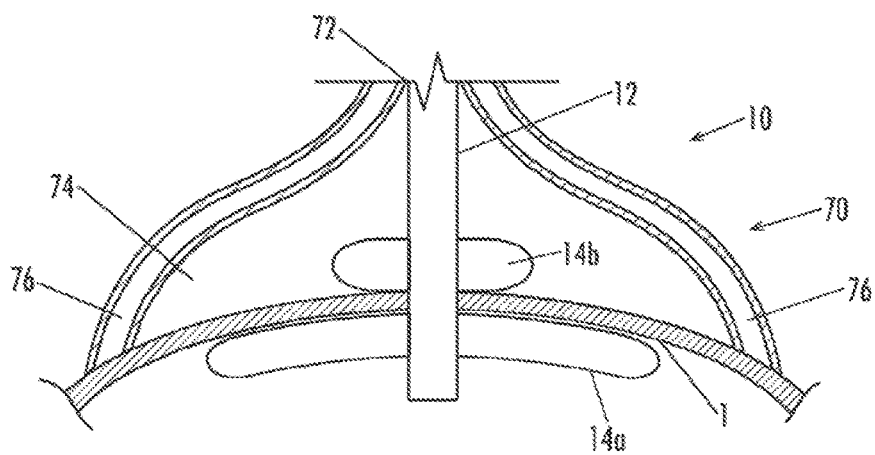
Fig. 9

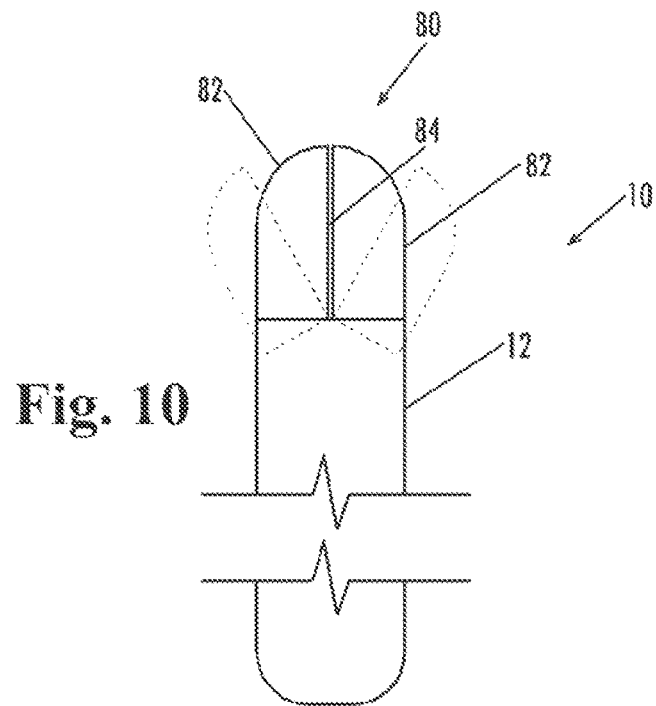
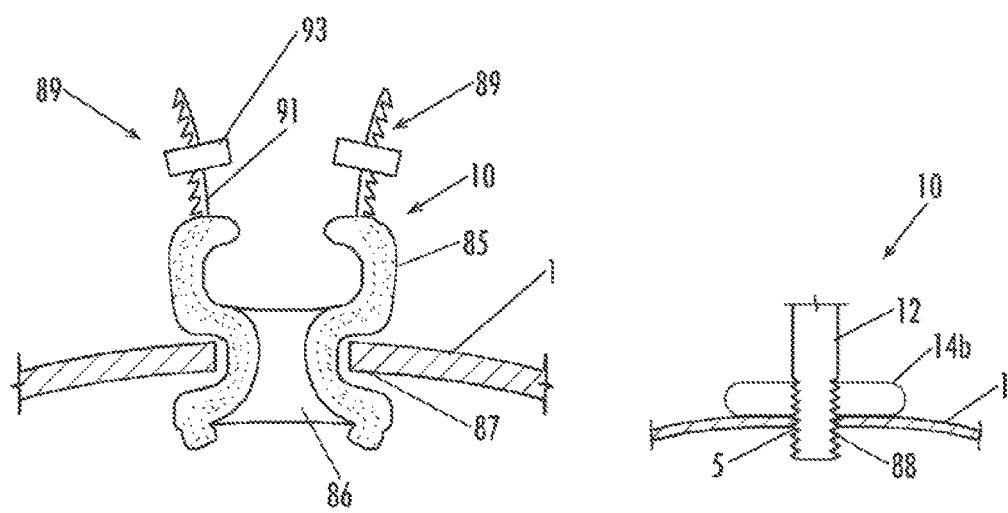
Fig. 10   Fig. 11   Fig. 12

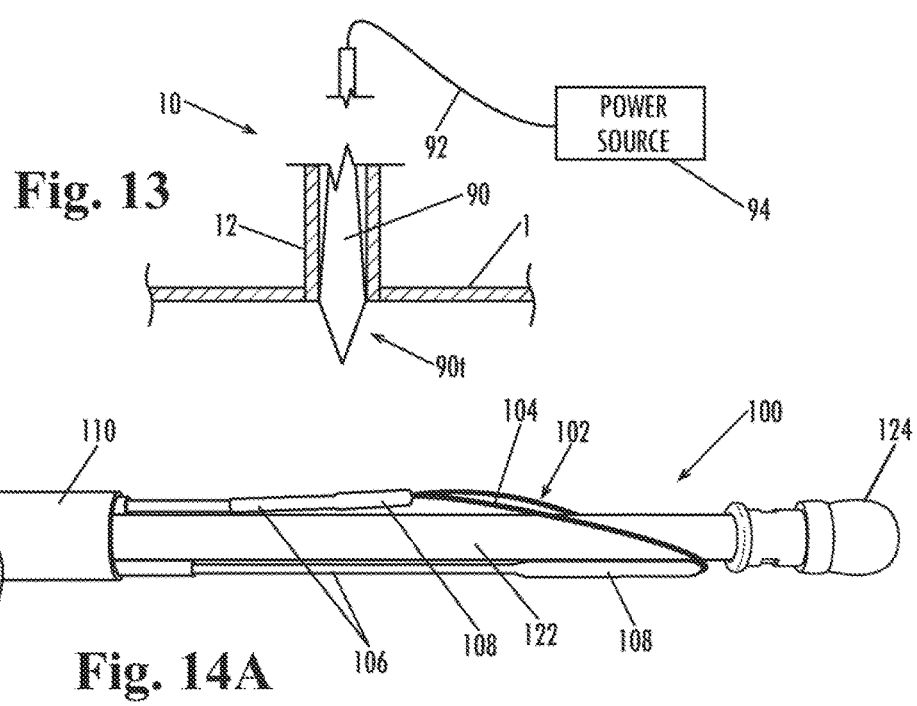
Fig. 13
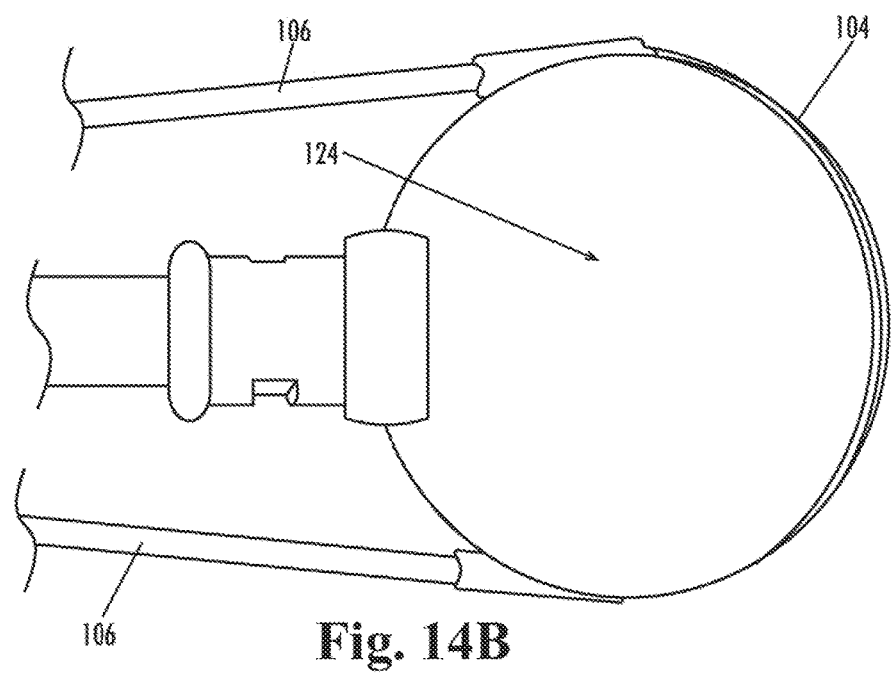
Fig. 14A
Fig. 14B

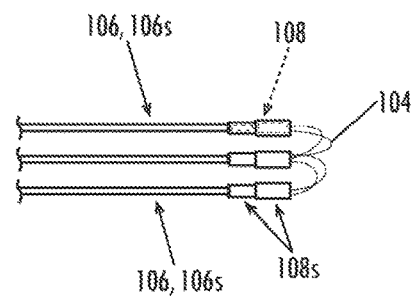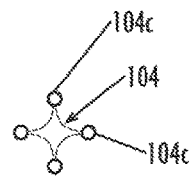
Fig. 15A      Fig. 15B
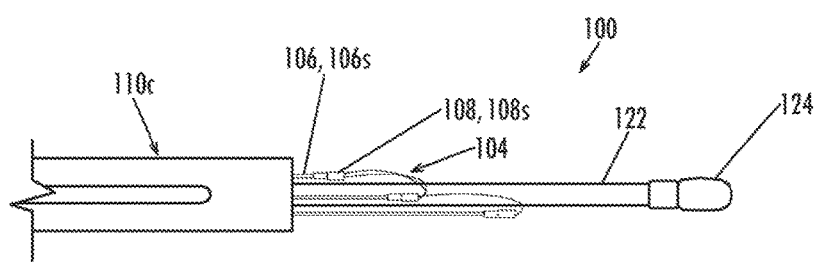
Fig. 15C
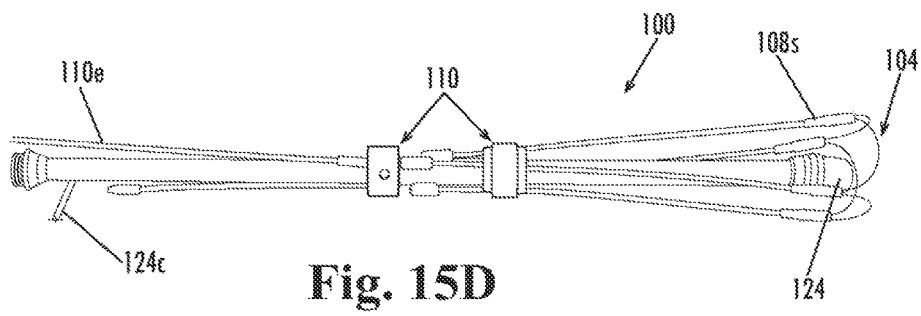
Fig. 15D
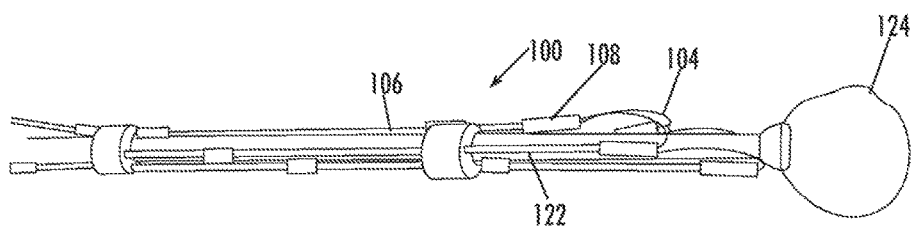
Fig. 15E

DEVICES AND METHODS FOR MINIMALLY-INVASIVE SURGICAL PROCEDURES

CROSS-REFERENCE

This application is a continuation of, pursuant to 35 U.S.C. § 120, U.S. patent application Ser. No. 12/245,246, filed. Oct. 3, 2008, which is a non-provisional of and claims the benefit of priority to, U.S. Provisional Application No. 60/997,985, filed Oct. 5, 2007, pursuant to 35 U.S.C. § 119(e), which applications are incorporated herein, in their entirety, by reference thereto.

FIELD OF THE INVENTION

The present invention relates to the field of minimally invasive surgery and provides devices, instruments and methods for minimally invasive surgical procedures.

BACKGROUND OF THE INVENTION

A continuing trend in the performance of cardiac surgical procedures, as well as other surgical procedures performed on an internal organ or tissue of an organism is toward minimizing the invasiveness of such procedures. When entering a fluid containing internal organ to provide access for inserting tools therethrough to perform one or more surgical procedures, it would be desirable to provide a hemostatic port that prevents or minimizes introduction of air or other intended fluids or substances into the organ, while at the same time preventing substantial losses of blood or other fluids out of the organ, and while still providing an access port through which instruments can gain access to an intended surgical target site.

It would be further desirable to install such a port device in as atraumatic fashion as possible, by minimally invasive methods.

Examples of cardiac surgical procedures that could benefit from such a device include, but are not limited to: endocardial ablation procedures, valve surgeries, closure of patent foramen ovales, or for any other type of cardiac procedure requiring access into the heart.

In the cardiac field, cardiac arrhythmias, and particularly atrial fibrillation are conditions that have been treated with some success by various procedures using ninny different types of ablation technologies. Atrial fibrillation continues to be one of the most persistent and common of the cardiac arrhythmias, and may further be associated with other cardiovascular conditions such as stroke, congestive heart failure, cardiac arrest, and/or hypertensive cardiovascular disease, among others. Left untreated, serious consequences may result from atrial fibrillation, whether or not associated with the other conditions mentioned, including reduced cardiac output and other hemodynamic consequences due to a loss of coordination and synchronicity of the beating of the atria and the ventricles, possible irregular ventricular rhythm, atrioventricular valve regurgitation, and increased risk of thromboembolism and stroke.

As mentioned, various procedures and technologies have been applied to the treatment of atrial arrhythmias/fibrillation. Drug treatment is often the first approach to treatment, where it is attempted to maintain normal sinus rhythm and/or decrease ventricular rhythm. However, drug treatment is often not sufficiently effective and further measures must be taken to control the arrhythmia.

Electrical cardioversion and sometimes chemical cardioversion have been used with less than satisfactory results, particularly with regard to restoring normal cardiac rhythms and the normal hemodynamics associated with such.

A surgical procedure known as the MAZE III (which evolved from the original MAZE procedure) procedure involves electrophysiological mapping of the atria to identify macroreentrant circuits, and then breaking up the identified circuits (thought to be the drivers of the fibrillation) by surgically cutting or burning a maze pattern in the atrium to prevent the reentrant circuits from being able to conduct therethrough. The prevention of the reentrant circuits allows sinus impulses to activate the atrial myocardium without interference by reentering conduction circuits, thereby preventing fibrillation. This procedure has been shown to be effective, but generally requires the use of cardiopulmonary bypass, and is a highly invasive procedure associated with high morbidity.

Other procedures have been developed to perform transmural ablation of the heart wall or adjacent tissue walls. Transmural ablation may be grouped into two main categories of procedures: endocardial and epicardial. Endocardial procedures are performed from inside the wall (typically the myocardium) that is to be ablated, and is generally carried out by delivering one or more ablation devices into the chambers of the heart by catheter delivery, typically through the arteries and/or veins of the patient. Surgical epicardial procedures are performed from the outside wall (typically the myocardium) of the tissue that is to be ablated, often using devices that are introduced through the chest and between the pericardium and the tissue to be ablated. However, mapping may still be required to determine where to apply an epicardial device, which may be accomplished using one or more instruments endocardially, or epicardial mapping may be performed. Various types of ablation devices are provided for both endocardial and epicardial procedures, including radiofrequency (RF), microwave, ultrasound, heated fluids, cryogenics and laser. Epicardial ablation techniques provide the distinct advantage that they may be performed on the beating heart without the use of cardiopulmonary bypass.

When performing procedures to treat atrial fibrillation, an important aspect of the procedure generally is to isolate the pulmonary veins from the surrounding myocardium. The pulmonary veins connect the lungs to the left atrium of the heart, and join the left atrial wall on the posterior side of the heart. When performing open chest cardiac surgery, such as facilitated by a full sternotomy, for example, epicardial ablation may be readily performed to create the requisite lesions for isolation of the pulmonary veins from the surrounding myocardium. Treatment of atrial ablation by open chest procedures, without performing other cardiac surgeries in tandem, has been limited by the substantial complexity and morbidity of the procedure. However, for less invasive procedures, the location of the pulmonary veins creates significant difficulties, as typically one or more lesions are required to be formed to completely encircle these veins.

One example of a less invasive surgical procedure for atrial fibrillation has been reported by Saltman, "A Completely Endoscopic Approach to Microwave Ablation for Atrial Fibrillation", The Heart Surgery Forum, #2003-11333 6 (3), 2003, which is incorporated herein in its entirety, by reference thereto. In caning out this procedure, the patient is placed on double lumen endotracheal anesthesia and the right lung is initially deflated. Three ports (5 mm port in fifth intercostal space, 5 mm port in fourth intercostal space, and a 10 mm port in the sixth intercostal space) are created through the right chest of the patient, and the pericardium is then dissected to enable two catheters to be placed, one into the transverse sinus and one into the oblique sinus. Instruments are removed from the right chest, and the right lung is re-inflated. Next, the left lung is deflated, and a mirror reflection of the port pattern on the right chest is created through the left chest. The pericardium on the left side is dissected to expose the left atrial appendage and the two catheters having been initially inserted from the right side are retrieved and pulled through one of the left side ports. The two catheter ends are then tied and/or sutured together and are reinserted through the same left side port and into the left chest. The leader of a Flex 10 microwave probe (Guidant Corporation, Santa Clara, Calif.) is sutured to the end of the upper catheter on the right hand side of the patient, and the lower catheter is pulled out of a right side port to pull the Flex 10 into the right chest and lead it around the pulmonary veins. Once in proper position, the Flex 10 is incrementally actuated to form a lesion around the pulmonary veins. The remaining catheter and Flex 10 are then pulled out of the Chest and follow-up steps are carried out to close the ports in the patient and complete the surgery.

Although advances have been made to reduce the morbidity of atrial ablation procedures, as noted above, there remains a continuing need for devices, techniques, systems and procedures to further reduce the invasiveness of such procedures, thereby reducing morbidity, as well as potentially reducing the amount of time required for a patient to be in surgery, as well as reducing recovery time. There remains a continuing need as well for minimizing the invasiveness of other surgical procedures performed within the heart.

There remains a continuing need for minimizing the invasiveness of the procedures for providing access to other internal organs and tissue as well.

SUMMARY OF THE INVENTION

The present invention provides an assembly usable in performing minimally-invasive ablation procedures is provided that includes: an elongated shaft; a balloon fitted over a distal end of the elongated shaft, the balloon being configured to assumed a deflated configuration, as well as an inflated configuration wherein the balloon has an outside diameter greater than an outside diameter of the balloon in the deflated configuration; and a halo comprising wires configured to be positioned proximal of the balloon in a retracted configuration and movable to a position distal of the balloon in an expanded configuration, wherein, when in the expanded configuration, the halo defines an area larger than a contracted area defined by the halo when in the retracted configuration.

In at least one embodiment, the halo is advanceable over the balloon when the balloon is in the inflated configuration.

In at least one embodiment, the halo comprises superelastic wires that expand a configuration of the halo when moving from the retracted configuration to the expanded configuration.

In at least one embodiment, the superelastic wires slide over the balloon and the balloon deforms somewhat as the halo passes from the retracted configuration to deploy over the balloon to the expanded configuration.

In at least one embodiment, a plurality of push rods are connected to the halo, the push rods being axially slidable relative to the shaft to move the halo from the retracted configuration position and the deployed, expanded configuration position and vice versa.

In at least one embodiment, an actuator is connected to proximal ends of the push rods, the actuator being slidable over the shaft.

In at least one embodiment, the actuator comprises an extension extending proximally to a proximal end portion of the shaft.

In at least one embodiment, the halo is electrically connectable to a source of ablation energy proximal of the assembly.

In at least one embodiment, the halo is connectable to a source of ablation energy proximal of the assembly.

In at least one embodiment, a conduit connecting with the balloon extends proximally of a proximal end of the shaft, the conduit being connectable in fluid communication with a source of pressurized fluid.

In at least one embodiment, the shaft comprises a cannula, the cannula being configured and dimensioned to receive an endoscope shaft therein, with a distal tip of the endoscope being positionable within the balloon.

In at least one embodiment, the shaft comprises a shaft of an endoscope.

In at least one embodiment, the halo is formed of two wires and forms a substantially oval shape when in the expanded configuration.

In at least one embodiment, the halo forms an encircling shape when in the expanded configuration.

In at least one embodiment, the halo is formed of four wires and forms a substantially quadrilateral shape when in the expanded configuration.

An instrument usable in performing minimally-invasive ablation procedures is provided that includes: an elongated shaft a balloon fitted over a distal end of the elongated shaft, the balloon being configured to assume a deflated configuration, as well as an inflated configuration wherein the balloon has an outside diameter greater than an outside diameter of the balloon in the deflated configuration; and a halo comprising wires configured to be positioned proximal of the balloon in a retracted configuration and movable to a position distal of the balloon in an expanded configuration, wherein, when in the expanded configuration, the halo defines an area larger than a contracted area defined by the halo when in the retracted configuration; and an endoscope having a distal tip thereof positioned adjacent to an opening of the balloon or within the balloon.

In at least one embodiment, the shaft comprises a shaft of the endoscope.

In at least one embodiment, the shaft comprises a cannula and wherein a shaft of the endoscope is received in the cannula.

In at least one embodiment, the halo is advanceable over the balloon when the balloon is in the inflated configuration.

In at least one embodiment, the halo comprises superelastic wires that expand a configuration of the halo when moving from the retracted configuration to the expanded configuration.

In at least one embodiment, the superelastic wires slide over the balloon and the balloon deforms somewhat as the halo passes from the retracted configuration to deploy over the balloon to the expanded configuration.

In at least one embodiment, a plurality of push rods are connected to the halo, the push rods being axially slidable relative to the shaft to move the halo from the retracted configuration position and the deployed, expanded configuration position and vice versa.

In at least one embodiment, an actuator is connected to proximal ends of the push rods, the actuator being slidable over the shaft.

In at least one embodiment, the actuator comprises an extension extending proximally to a proximal end portion of the endoscope.

In at least one embodiment, the halo is electrically connectable to a source of ablation energy proximal of the instrument.

In at least one embodiment, the halo is connectable to a source of ablation energy proximal of the instrument.

In at least one embodiment, a conduit connecting with the balloon extends proximally of a proximal end portion of the shaft, the conduit being connectable in fluid communication with a source of pressurized fluid.

In at least one embodiment, the halo is formed of two wires and forms a substantially oval shape when in the expanded configuration.

In at least one embodiment, the halo forms an encircling shape when in the expanded configuration.

In at least one embodiment, the halo is formed of four wires and forms a substantially quadrilateral shape when in the expanded configuration.

These and other features of the invention will become apparent to those persons skilled in the art upon reading the details of the devices, assemblies, instruments and methods as more fully described below.

BRIEF DESCRIPTION OF THE DRAWINGS

FIGS. 1A-1B illustrate longitudinal sectional views of a hemostatic port device that can be installed by minimally invasive techniques.

FIG. 1C shows a view of the device of FIGS. 1A-1B having been installed through an opening in tissue, and expandable members of the device having been expanded to capture the tissue therebetween and form a hemostatic seal therewith.

FIGS. 2A and 2B illustrate steps in one example of installation of a port device in the left atrial appendage of the heart of a patient.

FIGS. 2C and 2D illustrate an arrangement configured for quick and easy removability of a dilator from to a port device.

FIGS. 3A-3C illustrate another version of a port device and procedural steps included in its installation.

FIGS. 4A-4E illustrate another version of a port device and procedural steps included in its installation.

FIGS. 8A-8B illustrate a port device that can be used to provide an opening into an atrial appendage for insertion of tools and/or devices therethrough to carry out a procedure inside a chamber of the heart.

FIGS. 8C-8D illustrate mechanical linkage that may be provided so that rotation of only one cylinder of the device of FIGS. 8A-8B causes linked rotation of both rollers.

FIG. 9 illustrates a partial sectional view of another port device.

FIG. 10 illustrates a port device comprising a cannula having a closable distal end portion.

FIG. 11 illustrates another version of a port device.

FIG. 12 illustrates another version of a port device.

FIG. 13 illustrates another version of a port device.

FIG. 14A illustrates a distal end portion of an assembly that can be inserted through a port device to visualize structures in the internal chamber accessed through the port device as well as to perform ablation procedures.

FIG. 14B shows the distal end portion of the assembly of FIG. 14A with balloon inflated/expanded and halo deployed.

FIGS. 15A-15B illustrate a halo assembly wherein the halo is formed from four superelastic wires FIG. 15C shows a portion of an assembly having a four-wire halo.

FIG. 15D illustrates an assembly having a four wire halo, with the halo shown in the deployed position and expanded configuration, and with the balloon in a deflated, non-expanded configuration.

FIG. 15E shows the assembly of FIG. 15D with the halo in a retracted position and compressed configuration, and wherein the balloon has been inflated/expanded.

DETAILED DESCRIPTION OF THE INVENTION

Figure 5A:
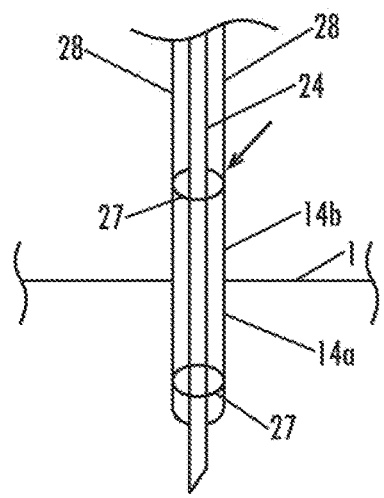
FIGS. 5A-5D illustrate another version of a port device and procedural steps included in its installation.
Figure 5B:
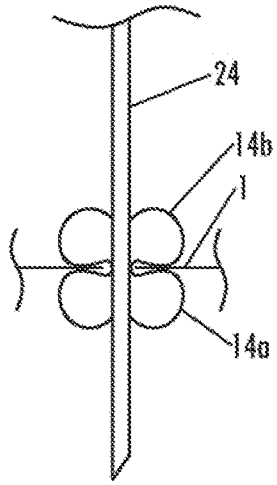

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a lumen" includes a plurality of such lumens and reference to "the target" includes reference to one or more targets and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "open-chest procedure" refers to a surgical procedure wherein access for performing the procedure is provided by a full sternotomy or thoracotomy, a sternotomy wherein the sternum is incised and the cut sternum is separated using a sternal retractor, or a thoracotomy wherein an incision is performed between a patient's ribs and the incision between the ribs is separated using a retractor to open the chest cavity for access thereto.

The term "closed-chest procedure" or "minimally invasive procedure" refers to a surgical procedure wherein access for performing the procedure is provided by one or more openings which are much smaller than the opening provided by an open-chest procedure, and wherein a traditional sternotomy is not performed. Closed-chest or minimally invasive procedures may include those where access is provided by any of a number of different approaches, including mini-sternotomy, thoracotomy or mini-thoracotomy, or less invasively through a port provided within the chest cavity of the patient, e.g., between the ribs or in a subxyphoid area, with or without the visual assistance of a thoracoscope. It is further noted that minimally invasive procedures are not limited to dosed-chest procedures but may be carried out in other reduced-access, surgical sites, including, but not limited to, the abdominal cavity, for example.

The term "reduced-access surgical site" refers to a surgical site or operating space that has not been opened fully to the environment for access by a surgeon. Thus, for example, closed-chest procedures are carried out in reduced-access surgical sites. Other procedures, including procedures outside of the chest cavity, such as in the abdominal cavity or other locations of the body, may be carried out as reduced access procedures in reduced-access surgical sites. For example, the surgical site may be accessed through one or more ports, cannulae, or other small opening(s), sometimes referred to as "minimally invasive surgery". What is often referred to as endoscopic surgery is surgery carried out in a reduced-access surgical site.

Devices and Methods

FIGS. 1A-1B illustrate longitudinal sectional views of a hemostatic port device 10 that can be installed by minimally invasive techniques described herein. Device 10 includes a flexible, malleable or substantially rigid cannula 12 having two expandable members 14a and 14b mounted circumferentially around a distal end portion of cannula 12 wherein one of the expandable members 14a is mounted distally of the other 14b. Examples of materials from which cannula 12 may be made include but are not limited to: polycarbonate, stainless steel, polyurethane, silicone rubber, polyvinyl chloride, polyethylene, nylon, C-FLEX® (thermoplastic elastomer), etc. Expandable members 14a, 14b are typically mounted with a small space or gap 16 therebetween (e.g., about two to about 10 mm), where a tissue wall of an organ, conduit or other tissue is to be captured between the expandable members 14a, 14b. In the example shown in FIGS. 1A-1B, dedicated lumens 16a, 16b are provided to connect expandable members 14a, 14b in fluid communication with a source of pressurized fluid located proximal of the proximal end of device 10 for delivering pressurized fluid to inflate the expandable members 14a, 14b as shown in FIG. 1B. Alternatively, although less preferred, both expandable members 14a, 14b could be provided in fluid communication with a pressurized fluid source via a single lumen.

When inflated, expandable members 14a, 14b expand to expanded configurations which narrow the gap 16 therebetween (or completely eliminate the gap, as illustrated in FIG. 1B) when no tissue is provided therebetween, as the outside diameters of the expandable members increase significantly. These diameters will vary depending upon the specific application for which device 10 is to be used, and on the outside diameter of the cannula 12. In one specific example, the inside diameter of conduit 12 is about 10 mm, the outside diameter is greater than 10 mm and less than about 12 mm; and in the deflated, compact, or non-expanded configuration of expandable members 14a and 14b (shown in FIG. 1A), the expandable members 14a, 14b have outside diameters of about 12 mm to about 14 mm. While in an expanded configuration, the outside diameters of the expandable members 14a, 14b can range from about 100 mm to about 500 mm. FIG. 1C shows a view of device 10 having been installed through an opening in tissue 1 and expandable members 14a, 14b having been expanded to capture the tissue 1 therebetween and form a hemostatic seal therewith.

The proximal end portion of port device 10, i.e. the proximal portion of cannula 12 not having the expandable members 14a, 14h thereon may expand only a minimal distance proximally of expandable member 14b, e.g. about 0.5 to about 2 inches. Alternatively, depending upon the use of device 10, this proximal portion may extend a much greater distance. For example, in minimally invasive procedures where port device 10 is installed in an internal organ, the proximal end of device 10 will extend a sufficient length to be able to extend out of the patient when device 10 is installed in the organ as intended. In one example, where device 10 is installed in the left atrial appendage of the heart of a patient, the proximal end of conduit 10 extends from about 6 to about 10 inches proximally of the proximal surface of expandable member 14b.

in this embodiment, as well as any of the other embodiments described herein that include cannula 12, a hemostatic valve 15 may be provided within the proximal annular opening of cannula 12, to hemostatically seal the port when no instrument or device is being inserted therethrough. Additionally, valve 15 may at least partially seal against an instrument, tool or device as it is being inserted through cannula 12 so as to prevent or minimize loss of blood or other fluids through cannula 12 during such an insertion.

FIGS. 2A and 2B illustrate steps in one example of installation of port device 10 in the left atrial appendage 4 of the heart 2 of a patient. Atrial appendage management, and particularly left atrial appendage (LAA) management, is a critical part of the surgical treatment of atrial fibrillation. When using a minimally invasive approach (e.g. where surgical access is provided by thoracoscopy, mini-thoracotomy or the like), there is a high risk of complications such as bleeding when using contemporary atrial appendage management. Further, exposure and access to the base of the atrial appendage to be treated is limited by the reduced-access surgical site. Since the atrial appendage is typically closed off, ligated, clamped, sutured, removed (e.g., transected), or otherwise isolated from circulation in the heart, one aspect of the present invention provides devices and methods for establishing access to the left atrium of the heart by installing port device 10 in the atrial appendage 4. Advantageously, this reduces the number of openings that need to be made in the heart, such as to perform ablation, for example, since the atrial appendage would be cut or ligated anyway, and it is also used here as the access location/opening into the heart for insertion of minimally invasive tools to perform a cardiac procedure. Such procedures, as well as ligating or occluding the atrial appendage 4 can be performed while the heart continues to beat, and all by a minimally invasive approach. Such procedures may be performed solely from an opening in the left chest, or may be performed with additional openings in the chest, but still with only access through the left atrial appendage. It is again noted here that the present devices an methods are not limited to installation in the left atrial appendage or to either atrial appendage, but can be installed anywhere on the heart to provide access to one or more internal chambers thereof. Still further, the devices and methods described herein can be used to gain access to other internal organs, vessels, or tissues having an internal fluid containing chamber, by minimally invasive procedures, while preventing air or other unwanted substances from entering such chamber and while providing a hemostatic seal with the entry opening in the tissue to substantially prevent blood or other fluids from exiting such chamber via the opening.

FIG. 2A illustrates a removable dilator 18, extending distally of the distal end of device 10, being used to pierce through the tissue wall of the left atrial appendage to form an opening therein. Optionally, graspers, or some other endoscopic clamping tool 20 may be used to engage the atrial appendage 4 to provide a traction force against the force of the dilator against the atrial appendage as it pierces through. Dilator 8 can be conically shaped, as shown, so as to dilate the opening formed by tip 18t as the dilator is advanced further distally into the left atrial appendage. As the dilator 18 is inserted all the way through the opening, the distal end portion of device 10 follows and expandable member 14a is positioned inside the tissue wall of the atrial appendage while expandable member 14b is positioned just outside the tissue wall of the atrial appendage 4. Expandable member 14a is next inflated so as to expand it to have an outside diameter that prevents it form being pulled back through the opening in the atrial appendage 4. At this time, the dilator 18 can be retracted and removed from the device 10. Alternatively, expandable member 14b may first be expanded, prior to withdrawal of the dilator 18. Dilator 18 may be simply held in the relative position shown in FIG. 2A as it is inserted through the atrial appendage, with device 10 being held stationary relative to dilator 18 and thus advanced along with it. Alternatively, dilator 18 may be removably and temporarily attached to device 10. One configuration for such removable attachment is illustrated in FIGS. 2C and 2D, wherein the proximal end portion of dilator 18 is provided with an enlarged diameter proximal end portion 18a that acts as a stop against the proximal end 10a of device 10. In this way, dilator 18 can be slid into device 10 and used therein with the distal end portion extending from the distal end of device 10 as shown in FIG. 2A. Removal of dilator 18 can be performed by simply sliding dilator 18 back out of device 10. Of course, other alternative mechanical connecting configuration can be substituted for this arrangement, as would be readily apparent to one of ordinary skill in the mechanical arts.

After inflation of expandable member 14a, the second expandable member 14b can be inflated to expand (either before or after removal of dilator 18, as noted) to, together with expanded expandable member 14b, form a hemostatic seal of the opening through the atrial appendage. This seal is very atraumatic as the expandable members 14a, 14b do not expand radially within and against the opening, but apply axial compression to the tissues surrounding the opening and to the interface with the opening) to seal it. This is particularly important when the access opening is made in the atrial appendage 4, as the tissue of the atrial appendage 4 tends to be very friable so that if a seal is attempted by expanding something radially within the opening, the tissue tends to tear or otherwise disintegrate or fail. Axial compression of the tissues does not pose such risks, but actually helps maintain the integrity of these tissues and thus forms the seal in a very atraumatic way. This also provides a very stable connection, as once the more distal expandable member 14a is expanded, as shown in FIG. 23, device 10 is not easily removed and very unlikely to be accidentally displaced or removed. The compressive forces provided by expandable member 14b further add to this stability. Optionally, expandable member 14b need not always even be expanded, as expandable member 14a may expand sufficiently to compress against the inner wall surfaces of the atrial appendage to maintain device 10 in a stable position and to form a hemostatic seal of the opening through which device 10 passes. However, the additional stability and sealing provided by expandable member 14b makes expansion of the expandable member 14*b* a typical step that is performed during an installation of device 10. In one specific embodiment, with insertion of a device 10 having a 10 mm cannula 12 expandable member 14*a*, 14*b* are provided as elastomeric balloons and each inflated with about 7 to about 10 cc of saline.

Expandable members are typically formed as inflatable balloons, e.g., comprising a compliant material such as latex, silicone, polyurethane, or the like, or a semi-compliant or non-compliant material such as nylon, polyethylene, polyester, polyamide, polyethylene terepthalate (PET) and urethane, for example, with compliant materials being preferred, since they can be compressed to a smaller cross-sectional area for delivery into the patient and through the opening in the tissue. Alternative forms of expandable members 14*b* can be provided, including, but not limited to members comprising closed-cell foam that is compressible and self-expands when a compression three is removed, self expanding stents with attached graft material, etc. When self-expanding, a sheath, additional cannula or other structure for compressing the expandable members 14*a*, 14*b* can be used for delivery to the expandable members to the locations on opposite sides of the tissue wall in which the opening to be sealed is formed, and then removal of the sheath, cannula or other compression applying member is removed to allow the expandable members to self-expand, either sequentially (14*a* first, then 14*b*) or together.

FIGS. 3A-3C illustrate another version of a port device 10 and procedural steps included in its installation. Although shown being installed in a left atrial appendage, device 10 can be installed am where on the heart 2 for access into the heart 2. Further alternatively, device 10 can be installed in any of the other internal organs, vessels or other tissues described previously. In FIG. 3A, expandable members 14*a*, 14*b* and a sheath 22 are wrapped around an introducer needle 24 having a sharp distal tip 24*t*. The wrapped, compacted configuration of expandable members 14*a*, 14*h* and sheath 22 as shown in FIG. 3A can be maintained using a tie, an additional sheath wrapped around the compacted configuration, or a thin cannula that is slidably removable from the configuration, for example. Alternatively, the sheath 22 may include a superelastic material, such as nickel-titanium alloy or other superelastic material. For example, a stent or framework capable of collapsing and then resiliently returning to an expanded configuration can be provided, and can be covered by a non-porous material, such as silicone, or one of the other polymers noted herein for making sheath 22. Sheath 22 is a thin, flexible, tubular component, such as a piercing needle (can be any size, but typically 16 or 18 gauge) on which expandable members 14*a*, 14*b* are mounted, and, in the case where expandable members 14*a*, 14*b* are inflatable, also contains one or two lumens for inflating the expandable members 14*a*, 14*h*, wherein the one or two lumens are configured in the same manner as in the cannula 12 described with regard to FIG. 1A above. Sheath 22 and expandable members 14*a*, 14*h* (in a non-expanded, compact configuration) are twisted around introducer needle 24 to form a very compact cross-sectional area to minimize the site of the openings required for insertion into the patient and for insertion into the organ, vessel or other tissue, in this case, the left atrial appendage 4.

The assembly in the compact configuration is then driven against the target area (e.g., left atrial appendage) whereby driving the sharp distal tip 24*t* of introducer needle against the tissue pierces the tissue, thereby forming an opening that is no larger than it has to be to allow passage of the assembly therethrough. Alternatively, an incision can be made with an additional cutting instrument and then the introducer needle and compact configuration can be inserted through the incision. However, by making the opening with the introducer needle tip 24*t* and expanding it by driving the needle 24 and compact components 14*a* and 22 therethrough, this ensures that the opening is kept to a minimum size required. Further alternatively, a tool 20 may be used to provide a traction force on the atrial appendage or other tissue to be incised or pierced, to facilitate this step.

Once the needle tip 24*t* and expandable member 14*a* have been passed though the opening and positioned interiorly of the opening and the tissue wall of atrium 4, the compression member 25, in this case an additional outer sheath 25 is removed and expandable member 14*a* is expanded (in this case, inflated) thereby securing it within the atrial appendage 4. Expandable member 14*b* can be expanded either before or after withdrawal of needle 24 from the site, thereby forming an axially compressive hemostatic seal at and/or around the site of the opening 5. Next, a dilator 18 is inserted through sheath 22 to expand the inner diameter thereof, as well as the inner diameters of the expandable members 14*a*, 14*b* and cannula 12, configured with dilator 18 in any of the manners described above, is slid into the sheath 22, following dilator 18. Once cannula 12 has been inserted so that a distal end thereof is flush, or more typically, extending slightly distally (e.g., ranging from flush up to a distance of about 1 cm) from a distal end surface of expanded expandable member 14*a* dilator 18 is removed, thereby completing the installation of port device 10, which is now ready to receive instruments or other devices therethrough to carry out one or more surgical procedures.

FIGS. 4A-4E illustrate another version of a port device 10 and procedural steps included in its installation. Although shown being installed in a left atrial appendage, device 10 can be installed anywhere on the heart 2 for access into the heart 2. Further alternatively, device 10 can be installed in any of the other internal organs, vessels or other tissues described previously. In FIG. 4A, expandable member 14*a* is stretched over a distal end portion of an introducer needle 24 in a compact, non-expanded configuration, and expandable member 14*b* is stretched over a distal end portion of cannula 12, and the distal end portion of needle 24, together with expandable member 14*a* are delivered through an opening 5 that can be formed using any of the techniques described above with regard to FIGS. 3A-3C. Balloons 14*a*, 14*b* can be independently inflatable and the material extending between these balloons is a single layer (which may be the same or different material than that used to make the balloons) and that needs to be dilated after inflation of balloons 14*a*, 14*b*.

Expandable members 14*a*, 14*b* in this case are inflatable balloons, e.g., balloons formed of a thin layer of elastomer, such as silicone, latex, polyurethane etc. The material joining the two expandable members that is position through opening 5 can also be the same as the material for the expandable members, but is typically not inflated, only expanded by dilation. Device 10 also contains one or two lumens extending through cannula 12 and one extending through to join expandable member 14*a*, for inflating the expandable members 14*a*, 14*b*, wherein the one or two lumens are configured in the same manner as in the cannula 12 described with regard to FIG. 1A above.

Once expandable member/distal end of cannula are abutting or in close proximity to the outer surface of the tissue wall 1 of atrial appendage 4 as illustrated in FIG. 4B, expandable member 14*a* can be released from needle 24.

Expandable member 14a must be low profiled (cross-sectional dimension) to follow the needle hole during insertion. The expandable member be released from needle 24 after inflation of expandable member 14a by withdrawing the needle 24 proximally when expandable member 14a is attached to needle via a perforated sleeve. Alternatively, this tear away can occur from forces applied to it by expansion of the expandable member 14a alone. Further alternatively, release can be performed by release of a suture knot outside of the body to release tension on a suture holding balloon 14a to needle 24. Upon expanding the expandable member 14a to secure the device against the inner surface of the tissue wall 1, this prevents device 10 from being pulled out as needle 24 is retracted, and needle 24 can be removed from the site, see FIG. 4C. In FIG. 4D, expandable member 14b is expanded to, together with expandable member 14a, form an axially compressive seal of the opening 5, by atraumatically axially compressing against the inner and outer tissue walls surrounding opening 5. At this stage, device 10 is installed and configured to accept other instruments, devices, etc, therethrough for performance of one or more surgical procedures within the organ, vessel or other anatomical structure that device 10 provides access to. Installation of device 10, as well as the subsequent procedures performed through device 10 can all be performed in a minimally invasive manner. FIG. 4E is a sectional illustration of the opening 5 as formed and hemostatically sealed by device 10 in a manner as described with regard to FIGS. 4A-4D above. The connecting material 14c that connects expandable members 14a and 14b passes through opening 5 and is expandable by dilation as additional tools or devices are passed therethrough. Expandable member 14a is also annular and includes a central opening therethrough 14ac that permits passage of the additional tools and/or devices.

FIGS. 5A-5D illustrate another version of a port device 10 and procedural steps included in its installation. Although shown being installed in a left atrial appendage 4, device 10 can be installed anywhere on the heart 2 for access into the heart 2. Further alternatively, device 10 can be installed in any of the other internal organs, vessels or other tissues described previously. In this embodiment, expandable members 14a, 14b are formed of an elastomeric, biocompatible foam, such as a closed-cell (e.g., nitrile rubber, silicone rubber, polyethylene, polyurethane, polyvinyl chloride, or the like) foam wherein expandable members can be manipulated to assume a first, contracted conformation in which expandable members 14a, 14b each have a relatively small outside diameter, and to assume a second, expanded conformation in which expandable members 14a, 14b, each have a relatively larger, expanded outside diameter.

Figure 5C:
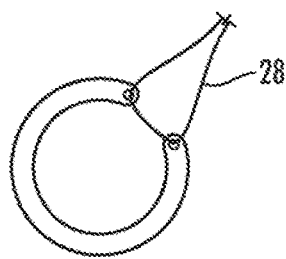
Figure 5D:
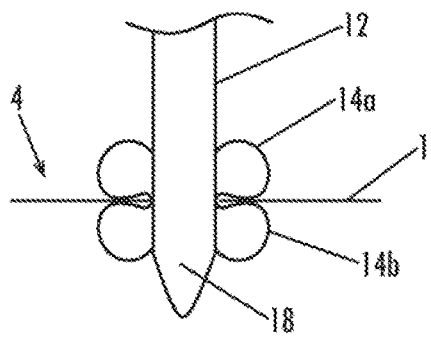

One wax of providing such expandable members is to mold the expandable members in a substantially hour-glass shape (similar to that shown in FIG. 5B, for example) with an annular opening running longitudinally through the center thereof to allow cannula 12 to be inserted therethrough. In this configuration, the contracted conformation can be achieved by stretching the expandable members 14a, 14b axially over a mandrel, such as an introducer needle 24, for example, as illustrated in FIG. 5A, and fixing the stretched foam material at a proximal end portion thereof and at a distal end portion thereof with releasable ties 27. Upon releasing ties 27, the expandable members return to their premolded hourglass-like shape illustrated in FIG. 5B. FIG. 5C illustrates wire or suture, or other tether material which is slidably received through ends of releasable tie 27 to maintain compression of tie 27 against portion 14a or 14h and mandrel 24, to maintain the tension on the expandable members 14a, 14b as shown in FIG. 5A and described above. Upon releasing one end of wire/suture/tether 28 and sliding it out of the ends of releasable tie 27, the compressive force is released, and the expandable member resumes its expanded configuration. Releasable tie may be fixed at one or more locations to the expandable member so that it need not be removed.

Accordingly, the expandable member 14a is inserted, together with introducer needle distal end portion 24 through the opening formed by tip 24t and into the atrial appendage 4 in a manner as described previously. Once in place, wires/sutures/tethers 28 are actuated to release the compressive forces by the releasable ties that are maintaining the expandable members 14a,14b stretched out in tension over the introducer 24, whereby expandable members retract toward one another, and radially expand to assume the hourglass configuration shown in FIGS. 5B and 5D. Regardless of whether expandable members 14a, 14b are sell-expanding, or are driven to expand, the expandable members axially compress the tissue in an atraumatic manner to hemostatically seal the opening 5. Once the expandable members 14a and 14b have assumed the expanded configurations, the introducer 24 is removed, and a dilator 18/cannula 12 combination can be inserted through the central opening of the expandable members to install cannula 12 in a manner as already described above, see FIG. 5D.

Figure 6A:
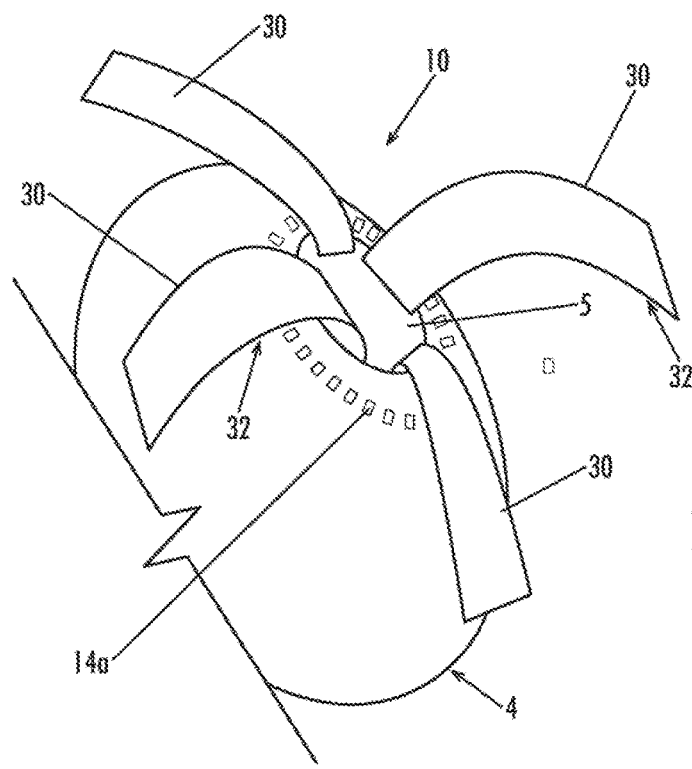
FIGS. 6A-6B illustrate another version of a port device.
Figure 6B:
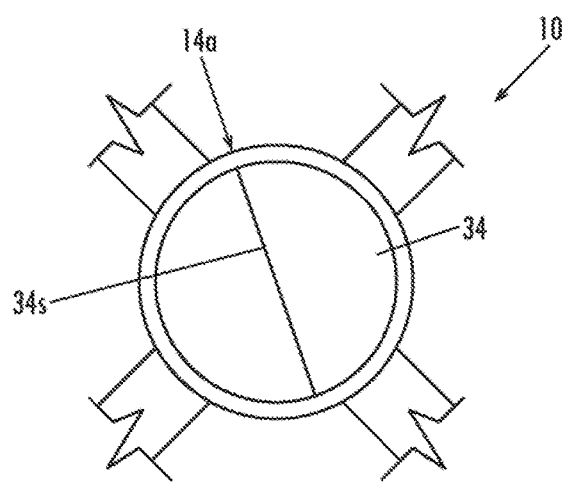

FIGS. 6A-6B illustrate another version of a port device 10 for any of the uses described previously herein. Thus, installed shown as installed in a left atrial appendage 4, device 10 can be installed anywhere on the heart 2 for access into the heart 2. Further alternatively, device 10 can be installed in any of the other internal organs, vessels or other tissues described previously. In this embodiment, expandable members 14a if formed of a resilient, self expanding unit that can be elastically deformed to assume a much smaller diameter than the expanded diameter illustrated in FIG. 6A. Thus, for installation of this device 10 a small hole 5 is cut through the tissue wall 1 of the organ, vessel or other tissue into which device is to installed (in this example, the left atrial appendage 4). The expandable member 14a, in the compressed or elastically deformed conformation having a much smaller diameter than in the expanded configuration, is inserted through the opening 5 and the allowed to expand in the cavity on the opposite side of the tissue wall 1. For example, expandable member 14a may be a ring of spring steel (stainless steel), an elastic polymer or a soft inelastic polymer, or a superelastic material, such as nickel-titanium alloy (e.g., Nitinol), or other biocompatible material having similar structural and elastic properties, that is solid and allows for inflation of the expandable member. Optionally, at least a surface of expandable member 14a that faces the tissue wall that it is to form a seal with, may be coated with silicone or other biocompatible elastomer or other biocompatible soft material to assist in making the seal of the expandable member 14a to the tissue wail. In the compressed/elastically deformed conformation, elastic member 14a can be delivered though opening 5 via a cannula 12, for example, or other structure designed to maintain the expandable member 14a in the compressed confirmation until being released therefrom by the cannula or other compressive structure.

Once expandable member 14a is allowed to expand, cloth (e.g. Dacron, woven polymer, or other known biocompatible fabrics acceptable for internal use) or non-compliant, but flexible polymer arms 30 that are attached to expandable member 14a and which extend out of opening 5 can be tensioned/retracted, to pull expandable member 14a against the inner surface of the tissue wall 1 thereby forming an atraumatic hemostatic seal. Flexible arms 30 may have an adhesive 32 coated on all or a portion of the side of each arm facing the external surface of the tissue wall 1, so that once expandable member 14a has been retracted sufficiently to form a hemostatic seal against the inner surface of tissue wall 1, arms 30 can be pressed against the outer surface of tissue wall 1, thereby adhering the arms to the tissue wall 1 and maintaining the hemostatic seal. Additionally or alternatively, arms 30 may be sutured, stapled and/or tacked to the tissue wall.

FIG. 6B illustrates a thin film 34 that extends across expandable member 14a and forms a seal therewith. Film 34 may be a thin sheet of silicone, latex, or polyurethane, for example. A slit 34s is provided in film 34 that functions like a one way valve. When installed as described with regard to FIG. 6a above, film 34 prevents substantial amounts of blood or other fluids from flowing therethrough and out of opening 5. However, when it is desired to insert a tool or device, this can be accomplished by passing the tool or device through the slit. After performing the intended function with the tool and the tool is removed, or when the device no longer extends through the slit, the slit automatically recluses, again preventing or substantially reducing fluid loss out of the opening 5.

Figure 7A:
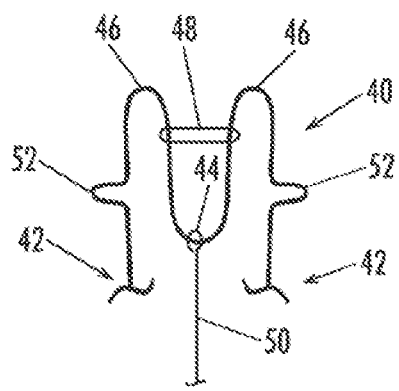
FIG. 7A illustrates a closure device that may be used to close an opening through a tissue wall upon removal of a port device therefrom.
Figure 7B:
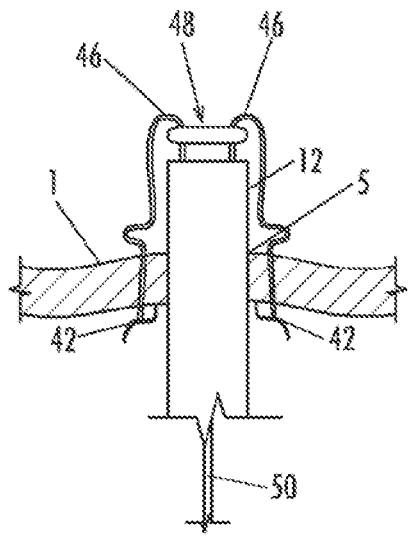
FIGS. 7B-7D show steps that may be performed using the device of FIG. 7A to close an opening.
Figure 7C:
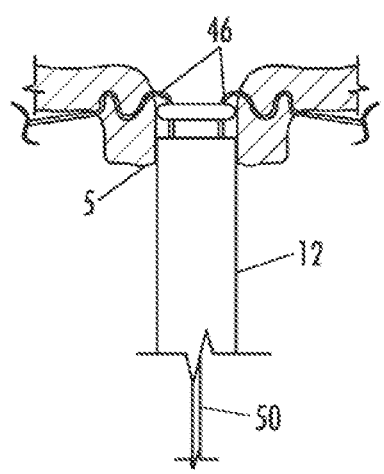
Figure 7D:
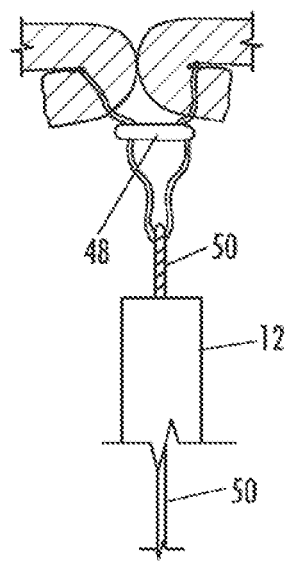

FIG. 7A illustrates a closure device 40 that may be used to close an opening 5 through a tissue wall upon removal of port device 10 therefrom. Device 40 is adapted for use with any of the devices 10 described herein that employ cannula 12. For those devices 10 that do not employ cannula 12, device 40 can still be used to perform closure after removal of such device 10 by providing a cannula with device 40 for delivery thereof FIGS. 7B-7D show steps that may be performed using device 40 to close opening 5. For devices 10 employing cannula 12, these steps are performed after compacting at least expandable member 14a back to a reduced outside diameter, compact configuration. For simplicity, expandable members 14a and 14b are not shown in FIGS. 7B-7D, as the same steps may be performed whether a device 10 having expandable member 14a in a compact conformation is used, or a cannula 12 having no expandable members is inserted after removal of a device 10 that does not employ cannula 12.

Device 40 comprises a malleable wire having barbs 42 formed at both ends thereof. Device 40 has a central acute bend 44 and a pair of additional acute bends 46 in an opposite direction. A locking ring 48 that is slidable over the wires of device 40 is initially positioned proximally adjacent this additional pair of bends 46. A pusher rod or wire 50 is attached to the central acute bend 44 and has sufficient column strength to push device 40 distally through cannula 12, and sufficient tensile strength to pull barbs 42 though the tissue wall 1. Bends 44, 46 allow device 40 to be elastically deformed/compressed to be pushed though cannula 12. Once barbed ends 42 clear the distal end of cannula 12, such as by pushing device 40 through cannula 12 by pushing on pusher rod/wire 50 from a location proximal of the proximal end of cannula 12 and outside of the patient's body, the barbed ends 42 spring radially outwardly beyond the outside diameter of cannula 12, Pusher rod/wire 50 can then be retracted proximally until bends 46 approach the distal end of cannula 12, as illustrated in FIG. 7B. Locking ring 48 remains positioned just proximal of bends 46 and may be positioned adjacent the distal end of cannula 12, as shown. In this position, locking ring helps improve the rigidity of the portions of device 40 that are external to cannula 12 to facilitate driving them through the tissue wall 1 as described hereafter.

Barbs 42 can be driven through the tissue wall 1 solely by retracting pusher wire/rod 50 relative to cannula 12, or alternatively, barbs can be positioned adjacent the external surface of tissue wall 1 through retracting pusher wire/rod 50, and then cannula 12 and pusher wire/rod 50 can be retracted together to drive barbs 42 through the tissue wall 1. In either case, after piercing through the tissue wall 1 with barbs 42, cannula 12 and pusher rod/wire 50 are retracted further together. As cannula 12 begins to exit the opening 5, the acute bends 46 begin to deform an increase in angle through right angle bends (FIG. 7C) to obtuse bend and then so that they are substantially straight or 180 degree bends (FIG. 7D), as the barbs 42 maintain their relative positions against the external surface of the tissue wall 1, since the barbs prevent the ends of the device 40 from pulling back through the wall 1 during this retraction step. This causes the edges of the tissue wall 1 that define opening 5 to begin everting, as shown in FIG. 7C. Once bends 46 have substantially straightened, cannula 12 can be retracted relative to device 40, and locking ring 48 can be distally advanced and locked into position over detents 52. This further everts the tissue edges and closes the opening 5 and locks ring 48 into position to maintain the closure, as shown in FIG. 7D. Endoscopic cutter or scissors (not shown) can be inserted through cannula 12 to cut pusher rod/wire 50, thereby severing it from device 40 and cannula 12 and pusher rod/wire 50 can then be removed from the patient to complete the closure and the procedure.

FIGS. 8A-8B illustrate another version of a port device 10 that can be used to provide an opening into an atrial appendage 4 for insertion of tools and/or devices therethrough to can out a procedure inside a chamber of the heart 2. Device 10 includes a pair of substantially cylindrical rollers 60 each having at least one scallop or concavity 62 formed therein and extending at least about 180 degrees circumferentially about the general cylindrical shape. Rollers 60 are positioned substantially parallel to one another and joined by a linkage 64 that permits the rollers to be separated from one another to increase a gap therebetween to allow the rollers to be placed over the atrial appendage 4 and then clamped on opposite sides thereof. Linkage 64 may be spring-loaded, so that rollers can be separated, for example, using graspers, and then upon release of the rollers by the graspers, spring-loaded linkage 64 resiliently draws rollers back toward one another to a configuration such as shown in FIGS. 8A and 8B.

Spring force provided by linkage 64 may be a predetermined number of pounds sufficient to clamp off the walls of the atrial appendage 4 to prevent blood flow therepast but not so great as to cause tissue damage or necrosis (e.g., about one to about four pounds force, combined). When scallops 62 are aligned as shown in FIG. 8A, they join to define an opening where an opening 5 in the atrial appendage tissue wall 5 can be formed for access inside the atrial appendage 4. As rollers are rolled to the configuration shown in FIG. 8B, where only the cylindrical surfaces abut the tissue wall, this effectively closes the opening 5, thereby substantially preventing fluid escape from the atrial appendage 4.

Rollers 60 may be independently rotated (such as by using graspers or other endoscopic tool, for example) to align the scallops 62 for opening the port, or to align the cylindrical surfaces to close the port. Alternatively, cylinders 60 may be linked, such as by gears 66 9 FIGS. 5C and 5D) or other mechanical linkage so that rotation of only one cylinder 60 serves to rotate both, and thus providing easier alignment of the scallops 62 or cylindrical surfaces, as the rotations are such as to guarantee equal rotations of both cylinders 60.

FIG. 9 illustrates a partial sectional view of another port device 10 that, in addition to cannula 12 and expandable members 14a, 14b that may be configured in any of the manners described above, a seal 70 (shown as a sectional view) is provided around cannula 12 at a location proximal of the expandable member 14b. Seal 70 includes a valve 72 such as a duck-bill or trap door type valve that doses of the chamber 74 defined around the opening when cannula 12 or cannula and expandable members 14a, 14b) are removed. Seal 70 may be provided with one or more vacuum channels 76 connectable to a source of vacuum external of the patient (via one or more vacuum lines) to form a vacuum seal with the outer surface of the tissue 1. Seal 70 may be engaged with the outer surface of the tissue wall 1, such as by applying vacuum in the manner described, to establish the chamber prior to inserting cannula and expandable member 14a through the tissue, and even prior to making the opening 5, so as to contain any blood loss that may occur as opening 5 is made and cannula 12 and expandable member 14a are initially inserted through the opening 5. Expandable member 14b may alternatively be replaced by a flange that is not expandable, but has the shape shown in FIG. 9.

FIG. 10 illustrates a port device 10 comprising a cannula 12 having a closable distal end portion 80. For example, distal end portion 80 may be bullet shaped and include a pair of pivotally mounted, spring-biased clamshell doors 82 that are spring loaded toward the closed position. An elastomeric seal 84 may optionally be provided on one or both clamshell doors 82 along the edges that abut one another during closing to further enhance the hemostatic seal. This bullet shaped distal end portion can be inserted through an opening 5 in tissue wall 1 to form an atraumatic, hemostatic seal that allows insertion of instruments and/or devices. Upon insertion of an instrument, tool or device from a proximal end through cannula 12, contact of the tool, instrument or device against the internal surfaces of the clamshell doors 82 drives them open, as illustrated, in phantom lines in FIG. 10. The bullet tip is elliptical in shape so that when clamshell doors 82 are open, the open edges of the clamshell doors are contoured to match or nearly match the shaft (typically cylindrical) of the instrument being inserted therethrough. This helps prevent fluid escaping therepast when the instrument is inserted through the open clamshell doors 82. Upon withdrawal of the tool or instrument, or when device no longer traverses the space between the clamshell doors 82, the clamshell doors automatically close, driven by the spring biasing, thereby re-establishing the hemostatic seal.

FIG. 11 illustrates another version of a port device 10 for any of the uses described previously herein. Thus, device 10 may be installed, through the wall of a left atrial appendage 4, a right atrial appendage, or through any wall of the heart 2 for access into the heart 2. Further alternatively, device 10 can be installed in any of the other internal organs, vessels or other tissues described previously. In this embodiment, the main body portion of device 10 includes a plug 85 that may be formed of a polymeric foam, for example. Plug 85 includes a central annulus 86 extending, therethrough along a longitudinal axis of the plug 85. A channel 87 is formed circumferentially in and around an external portion of the plug 85 to receive the tissue edges around the opening formed through the tissue wall 1. Compression members 89 are configured to axially compress the plug 85 to expand the channel radially outwardly into contact with the tissue wall edges, thereby sealing the opening. In one embodiment, compression members comprise elongate members 91 fixed to a distal portion of plug 85 and extending longitudinally through wall of the plug 85, wherein the walls are slidable with respect to the elongate members to allow compression with respect thereto. Proximal portions of elongate member 91 include ratcheted teeth that cooperate with pads 93 which can be advanced to lock down against the plug, like a zip-tie function. Pads 93 can be distally advanced over elongate member 91 and against plug 85 until plug compresses sufficiently to expand channel 87 sufficiently radially to seal off the opening. The elongate members may also be flexible, so that portions passing through the channel 87 tend to move radially outwardly as tension is generated in the elongate members 89.

FIG. 12 illustrates another version of a port device 10 for any of the uses described previously herein. Thus, device 10 may be installed through the wall of a left atrial appendage 4, aright atrial appendage, or through any wall of the heart 2 for access into the heart 2. Further alternatively, device 10 can be installed in any of the other internal organs, vessels or other tissues described previously. In this embodiment, cannula 12 is provided as a hollow screw and thus has a threaded distal end portion 88 that can be used to screw cannula 12 into and through the tissue wall 1. An expandable member 14b may be provided to inflate and axially compress the tissue Wail against the counterforce of the threads to atraumatically, hemostatically seal the opening 5.

FIG. 13 illustrates another version of a port device 10 for any of the uses described previously herein. Thus, device 10 may be installed through the wall of a left atrial appendage 4, a right atrial appendage, or through any wall of the heart 2 for access into the heart 2. Further alternatively, device 10 can be installed in any of the other internal organs, vessels or other tissues described previously. In this embodiment, a trocar 90 having a heatable, sharp distal tip portion 90t is inserted through cannula 12 during the formation of opening 5 and installation of cannula 12 therein. Trocar 90 includes a power cord 92 extending from a proximal end thereof that is electrically connectable to a power source 94 to provide energy to the distal tip portion 90t thereby heating it through resistive heating, for example. The heated, sharp tip 90t pierces easily though the tissue wall 1 by means of melting the tissue with an optional lesser degree of mechanical piercing. The distal end portion of cannula 12 can be coated with collagen or other biocompatible material that fuses or otherwise sticks to the tissue in the opening 5 when the tissue is heated by tip 90t passing therethrough. This thus forms a hemostatic seal between the tissue defining the opening 5 and the outer wall of cannula 12.

As noted earlier, with the minimally invasive installation of any of the port devices 10 described herein, instruments, tools and/or devices can then be inserted through the port device 10 for the performance of one or more minimally invasive surgical procedures. FIG. 14A illustrates a distal end portion of an assembly 100 that can be inserted through port device 10 to visualize structures in the internal chamber accessed through the port device 10 as well as to perform ablation procedures while directly visualizing the tissues to be ablated and with the ability to directly visualize the tissues as they are being ablated and after ablation. For example, when a port is installed through a tissue wall of the left atrial appendage 4, assembly 100, having an endoscope 200 mounted therein, can be inserted through port device 10 and used as an instrument to visualize structures on the wall of the left atrium and in the chamber of the left atrium.

Ablation around the pulmonary veins can be performed. Linear ablation lesions can be performed similarly, as will be described further below.

A halo assembly 102 is installed over shaft 122 (which may be the shaft of an endoscope or a cannula into which an endoscope shaft is inserted). Halo assembly includes an expandable halo 104 formed of electrically conducting superelastic wires, that are capable of being elastically deformed as they are drawn down (by retracting pushrods 106) to the compact configuration shown in FIG. 14A, but which elastically expand to an expanded configuration when they are pushed distally with respect to the shall 122. An endoscope shaft may be inserted through shaft 122. Monopolar or bipolar electrocautery current may be delivered to the wires of halo 104 to ablate tissue surfaces contacted by the wires. Halo 104 may be formed of two wires, in a substantially oval shape, as shown in FIG. 14A or with four wires, in a more circular or diamond shape when expanded. A pin 110p or other electrical connector is provided for connection to an external power source to supply current to the wires of halo 104. One or more of pushrods 106 electrically connect the pin or other electrical connector 110p with the wires of halo 104. A coupler 110f couples the assembly 102 to the endoscope 200 in the example shown in FIG. 14D. Stainless steel crimps 108 connect the pushrods 106 to halo 104 and help to keep the profile of halo 104 reduced when retracted, while allowing expansion of halo 104 over balloon 124 when balloon 124 is expanded. Pushrods 1011 retract to different retracted locations along cannula 122 so that one end of halo 104 is located more proximally than an opposite end as this facilitates reducing the overall diameter of the retracted halo 104. In the deployed configuration however, push rod 106 move the locations where they are connected to halo 104 all to substantially the same axial location relative to cannula 122, which facilitates expanding halo 104. Balloon 124 is in fluid communication with a source of pressurized fluid (e.g., saline) which can be inputted to greatly expand the size of the balloon to provide a viewing space into which the distal tip of the endoscope is inserted for viewing in an internal chamber of an organ, tissue or other structure having an internal chamber. Balloon 124 is typically made of an elastomer, such as silicone or latex, for example, and max be formed as what is sometimes referred to in the art as a balloon tip trocar (BTT). In at least one embodiment the wires of halo are made form Nitinol wire of about 0.012" diameter pre-shaped to form an encircling configuration when not under elastic compression. Superelastic wires having a diameter in a range of about 12 mm to about 25 mm are typically useable.

Pushrods 106 are connected proximally to an actuator 110 that is slidable over shall 122 to either retract halo 104 when actuator is retracted proximally along shall 122, or to extend and expand halo 104 when actuator is pushed distally with respect to shaft 122. In FIG. 14A, halos 104 is shown retracted, with actuator 110 in the retracted position relative to shaft 122, and balloon 124 is in a non-inflated state.

When balloon 124 is inflated and pressed up against a structure in an internal cavity, this substantially displaces blood or other fluid that may have been surrounding that structure and enables viewing of the structure via the distal tip of the endoscope residing in the inflated balloon.

FIG. 14B shows the distal end portion of assembly 100 where balloon 124 has been inflated/expanded, e.g. with saline and halo 104 is then extended over balloon 104 and positioned against a distal surface of balloon 124. Balloon 124 may be inflated by infusion through the inlet of conduit 124c (FIG. 14D) that provides fluid communication between a proximal end portion of the instrument and the balloon 124. For example, for a balloon that is provided over the end of a cannula 122 having an outside diameter of about 5 mm to about 7 mm, 124 can be expanded up to at least about 30 nm in diameter, thus allowing a relatively large area of anatomy to be viewed at once. Because of the expansion of the superelastic wires in halo 104 and the compliance of balloon 124, halo 104 can be slid over the balloon 124 in the expanded configuration shown. Alternatively, halo 104 can be expanded first and then balloon 124 can be inflated to result in the same configuration shown in FIG. 14B. However, balloon 124 is typically inflated first, as the inflated balloon is used to first inspect the surgical site and locate a target area to be ablated. Then halo 104 is deployed over balloon 124 to the configuration shown in FIG. 14B and the halo can then be accurately positioned on the location to be ablated, since the surgeon can now view the target tissue as well as the halo 104 through balloon 124 and the endoscope.

Figure 14C:
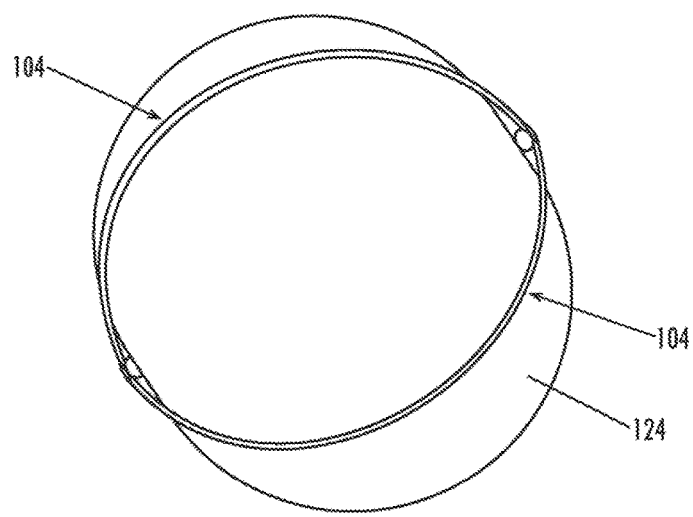
FIG. 14C is a distal end view of the balloon and halo of FIG. 14B.

FIGS. 14A and 14B show an example of a halo apparatus in which halo 104 is formed from two wires. FIG. 14C shows a distal end view of FIG. 14C, showing the substantially oval shape formed by halo 104 in the expanded configuration against the distal surface of balloon 124.

Figure 14D:
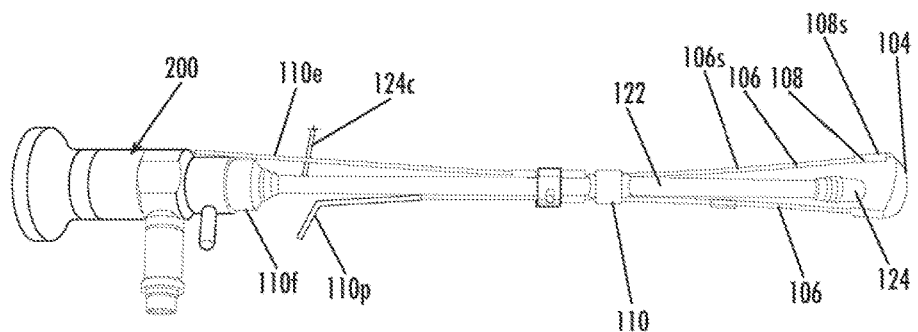
FIG. 14D shows the assembly of FIG. 14A with balloon in a non-inflated, configuration, with halo deployed in the extended and expanded configuration, and with an endoscope fully inserted.

As noted, shaft 122 may be provided as a cannula into which the shaft of an endoscope 200 can be inserted to provide a viewing and ablation instrument. FIG. 14D shows balloon in a non-inflated, non-expanded or deflated configuration with halo 104 deployed in the extended and expanded configuration. Endoscope 200 (5 mm Scholly Model 259008 0°/WA, in the embodiment shown) is inserted into shaft (cannula) 122 to place the distal tip of endoscope 200 within balloon 124. Endoscope 200 may be connected to cannula 122 by threading at proximal portions thereof, or by bayonet: connector, or other mechanical connector.

Pushrods 106 interconnect halo 104 and actuator 110 which is slidable over shaft 122. An extension 110e of actuator 110 is provided to allow manipulating from a location proximal of the assembly 100, typically in the vicinity of the proximal end portion of endoscope 200. In at least one embodiment, the wires forming halo 104 have a diameter of about 0.014" and are formed of Nitinol (nickel-titanium alloy) and pushrods 106 are stainless steel and have a diameter of about 0.037". Crimps 108 may be coated with white heat shrink tubing 108s and pushrods 106 may be coated with heat shrink tubing 106s (clear, in the example of FIG. 14D) which, in one particular embodiment, increases the overall diameter of pushrods 106 from about 0.037" to about 0.047" In other embodiments, pushrods having, smaller outside diameters are used.

FIGS. 15A-158 illustrate a halo assembly wherein halo 104 is formed from four superelastic wires. FIG. 15B is an illustration of a distal end view of halo 104 showing the substantially diamond-shaped or quadrilateral configuration of halo 104 and connection points 104c where pushrods 106 connect via crimps 108. FIG. 15C shows a portion of assembly 100 having a four-wire halo 104 and in which actuator 110 has been incorporated into a halo cover 110c. In one specific embodiment, halo cover has an outside diameter of about 0.375".

Figure 15F:
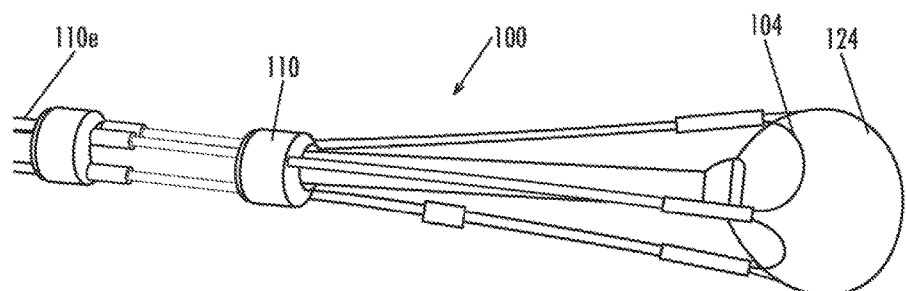
FIG. 15F shows the halo beginning to be deployed over the expanded/inflated balloon.
Figure 15G:
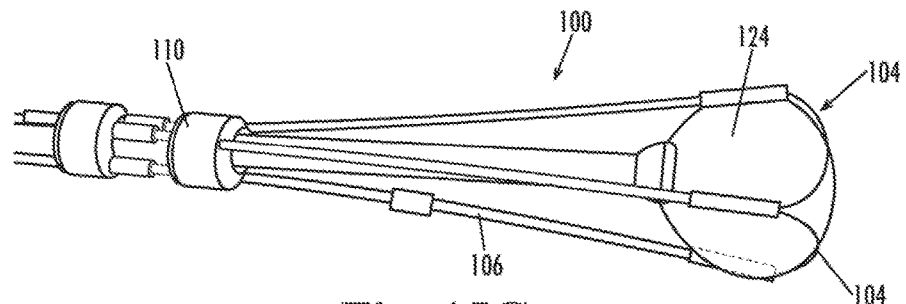
FIG. 15G shows the halo fully deployed over the inflated balloon so that it resides against the distal surface of the inflated balloon.
Figure 15H:
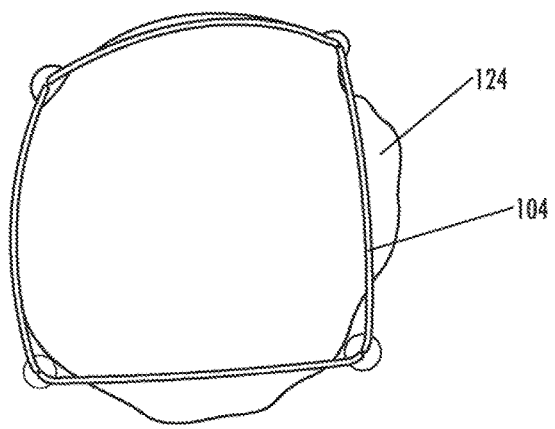
FIG. 15H shows the substantially expanded configuration of the halo at the distal surface of balloon.

FIG. 15D illustrates assembly 100 having a four wire halo 104 with halo 104 shown in the deployed position and expanded configuration, while balloon 124 is deflated, in a non-expanded configuration. FIG. 15E shows the assembly of FIG. 15D with halo 104 in a retracted position and compressed configuration, and wherein balloon 124 has been inflated/expanded. FIG. 15F shows the halo 104 beginning to be deployed over the expanded/inflated balloon 124 by manipulating actuator 110,110e, such as by pushing on the actuator extension 110e to drive actuator 110, pushrods 106 and halo 104 distally relative to balloon 124, and wherein halo 104 begins to expand as it is distally driven. FIG. 15G shows halo 104 fully deployed over the inflated balloon 124 so that it resides against the distal surface of the inflated balloon 124, FIG. 15H shows the substantially expanded configuration of halo 104 at the distal surface of balloon 124 in a distal end view of the balloon 124 and halo 104 in the configuration shown in FIG. 15G. It can be observed that the halo configuration is much closer to a circular configuration that that shown in FIG. 15B and is substantially square.

Figure 16:
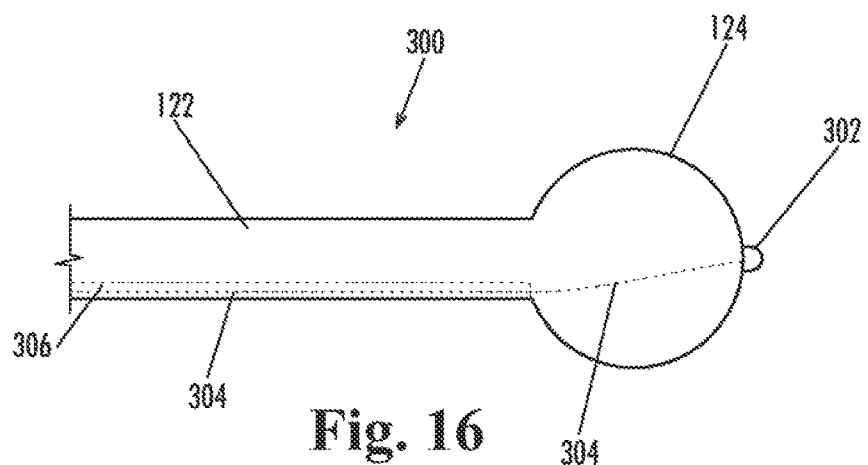
FIG. 16 illustrates a distal end portion of an assembly configured to form a linear lesion while directly viewing the tissue in which the lesion is being formed.

FIG. 16 illustrates a distal end portion of an assembly 300 configured to form a linear lesion while directly viewing the tissue in which the lesion is being formed. Similar to assembly 100, assembly 300 includes a cannula 122 having an inflatable balloon mounted over the distal end thereof. Cannula 122 is configured and dimensioned to receive the shaft of endoscope 200 so that the distal tip of endoscope 200 can be positioned at the opening or within balloon 124 for visualization through the balloon. FIG. 16 shows balloon in an inflated (expanded) configuration. A conduit 306 extends through cannula 122 and is in fluid communication with balloon 124 and configured to be connected in fluid communication with an inflation source (e.g., pressurized saline, or other suitable fluid) proximal of the assembly 300. An electrical connector (e.g., wire) 304 extends from ablation element 302 out of the proximal end portion of cannula 122 to be connected to a power source for supplying power to the ablation element 302 to perform ablation. For example, ablation element 302 may be a monopolar or dipolar conductive element that cauterizes contacted tissue when power is supplied thereto. Alternatively, other types of ablation energy may be used, such as, but not limited to: radio frequency (RF) energy, microwave energy, cryogenic, laser, etc. or chemical substance. Connector 304 may extend parallel to conduit 206 or through conduit 306, for example.

Ablation element comprises a metallic tip 302 mounted to a distal surface of balloon 124, preferably centrally mounted on the distal surface, although other locations may be chosen for mounting on the distal surface. Upon insertion of endoscope 200 into assembly 300 and then insertion of this instrument through a minimally invasive opening (such as provided via installation of one of the port devices 10 described herein, for example), balloon 124 can then be inflated, as shown, and then the instrument can be manipulated to slide the distal surface of the inflated balloon 124 along anatomical structures in the space into which the instrument was inserted. For example, in the case where the instrument is inserted through the left atrial appendage, and one or more encircling lesions have been performed around pulmonary vein ostia (such as by using a device of the types described in FIGS. 14A-15H, for example), the inflated balloon 124 and endoscope 200 can be manipulated to visualize the pulmonary ostia, the encircling lesion(s) and the mitral annulus. Once the surgeon has familiarized himself/herself with these locations, a linear lesion can be ablated to connect the encircling lesion(s) with the mitral annulus, by applying energy to ablation element 302 and dragging the ablation element from the encircling lesion(s) to the mitral annulus or vice versa, while viewing the ablation procedure, including the element 302 applying energy to the target tissue, through balloon 124 and endoscope 200.

A similar procedure can be performed using an instrument comprising an endoscope 200 inserted into an assembly 100 to form one or more encircling lesions around the pulmonary veins. In this procedure, identification and viewing of the location of the pulmonary veins can be conducted with balloon 124 inflated and halo 104 still in the retracted position and configuration. Once the surgeon has familiarized himself/herself with these locations, one or more encircling lesions can be ablated around the pulmonary veins by first deploying the halo to the deployed and expanded configuration on the distal surface of the expanded balloon 124, positioning the balloon against the target tissue so that the halo (as visualized through the balloon 124 and endoscope 2000 encircles the pulmonary ostia to be ablated around, and applying energy to halo 104 to create an encircling lesion while viewing the ablation procedure, including the halo 104 applying energy to the target tissue, through balloon 124 and endoscope 200. It is further noted, that during sliding movements of the expanded balloon 124 against the tissue surface, balloon 124 can tend to deform somewhat due to the forces of the friction between the balloon and the tissue during sliding movements and the compliant nature of the balloon material. When halo 104 is deployed over the balloon 124 as described above, the structure of the halo 104 helps to rigidify the balloon structure somewhat during these movements, thereby reducing the amount of balloon lag and time that it takes for the balloon to become axially aligned with the cannula 122 after a sliding movement.

Figure 17:
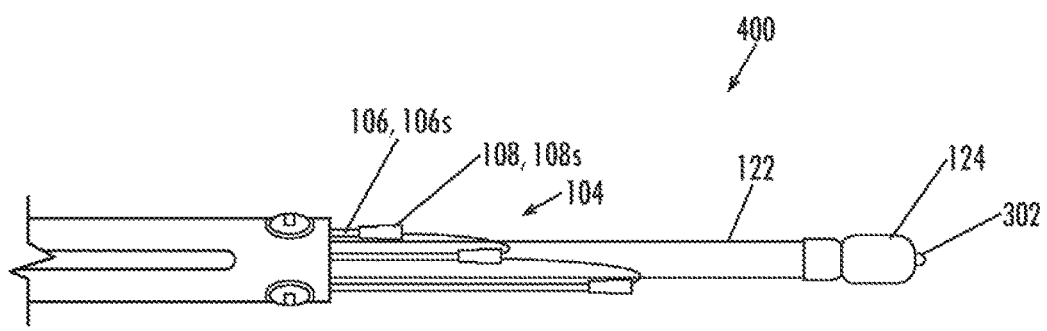
FIG. 17 illustrates an assembly that combines the linear ablation capabilities of the assembly of FIG. 16 with the encircling lesion forming capabilities of a halo.

FIG. 17 illustrates an assembly 400 that combines the linear ablation capabilities of assembly 300 with the encircling lesion forming capabilities of halo 104 in assembly 100. In this case, ablation element 302 and halo 104 are independently connectable to one or external energy sources and are independently controllable, so that ablation energy can be applied though element 302 without applying ablation energy to halo 104, and vice versa. Accordingly, using an instrument formed by inserting an endoscope 200 into assembly 400, one or more encircling lesions can be formed around the pulmonary veins in a manner as described above. Then, by either retracting halo 104 or leaving it in the deployed configuration, expanded balloon 124 can be manipulated to locate and visualize the target location for forming a linear ablation lesion, such as to connect the encircling lesion(s) with the mitral annulus, for example, and energy can be applied through ablation element 302 while dragging it and visualizing the lesion formation in a manner as described above. Since the balloon 124 is filled with saline, this acts to protect the balloon material from damage by the ablation element 302 and/or halo 104 as ablation energies are delivered therethrough to ablate the target tissues that the halo 104 or ablation element 302 and balloon 124 are contacted against during the ablation.

Figure 18:
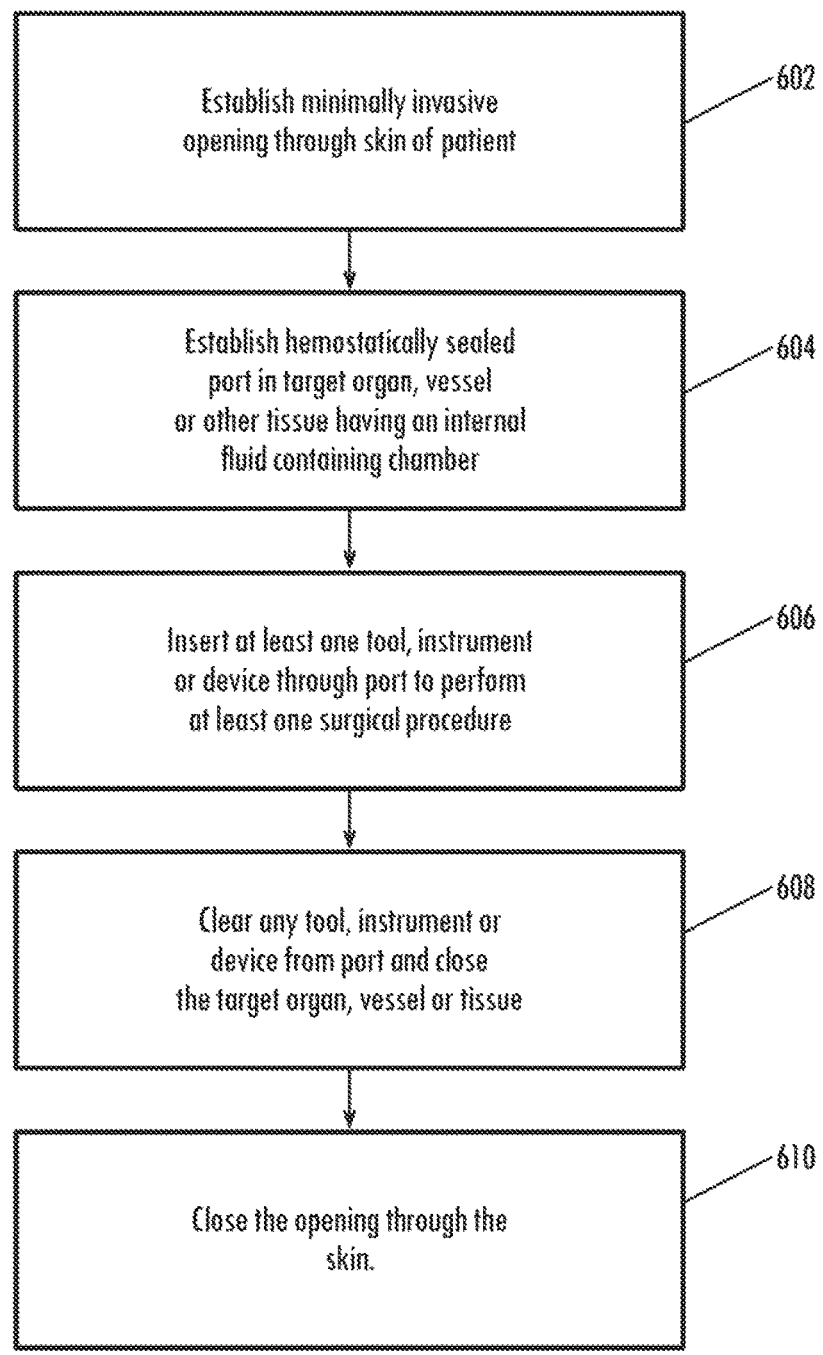
FIG. 18 illustrates steps that may be carried out during a minimally invasive procedure using one or more of the devices and/or instruments described herein.

FIG. 18 illustrates steps that may be carried out during a minimally invasive procedure using one or more of the devices and/or instruments described herein. At step 602, after prepping a patient for surgery, a minimally invasive opening is made in the patient, through the skin, in a location determined to best provide access to the organ, vessel or tissue in which a surgical procedure is to be conducted. Examples of such an opening include, but are not limited to, a thoracotomy, a mini-thoracotomy, establishment of a percutaneous port to the thoracic or abdominal cavity, or a percutaneous puncture at any location through the skin providing an access route to the target site.

At step 604, a hemostatically sealed port is established through the wall of an organ, vessel or tissue having an inner, fluid containing chamber (referred to as the target tissue), inside which a surgical procedure is to be conducted. Examples of target tissues (organ, vessel or other tissue) in which a hemostatically sealed port device may be installed through a wall thereof were described above. In one embodiment, a port device is installed through the wall of a left atrial appendage. In another embodiment, a port device 10 is installed though a wall of the heart at or near the apex of the heart to provide access to the left ventricle chamber. The hemostatically sealed is port is installed/established solely by minimally invasive techniques, wherein a port device 10 and any tools used to install the port device 10 are advanced to the target tissue through a minimally invasive opening in the patient. Many of the port devices 10 described herein have a cannula having sufficient length to extend out of the opening through the skin of the patient (and thus outside of the patient) even when the hemostatic seal is made to establish the port through the target organ, vessel or other tissue. Once the hemostatic port 10 has been successfully installed, at least one tool, instrument and or device are passed through the port and into the internal chamber to conduct at least one step of a surgical procedure, see step 606. Many different surgical procedures are possible, including those practiced by current endoscopic methods. In one example, atrial ablation is performed in any of the manners described above. In another example, heart valve surgery is conducted, and/or a heart valve prosthesis having already been implanted is directly visually inspected. After completion of the at least one surgical procedure step, the port is cleared of all tools, instrument and devices and the opening through the wall of the target tissue is closed, step 608. After this, closure of the patient is completed, including closing the opening through the skin, step 610.

Figure 19:
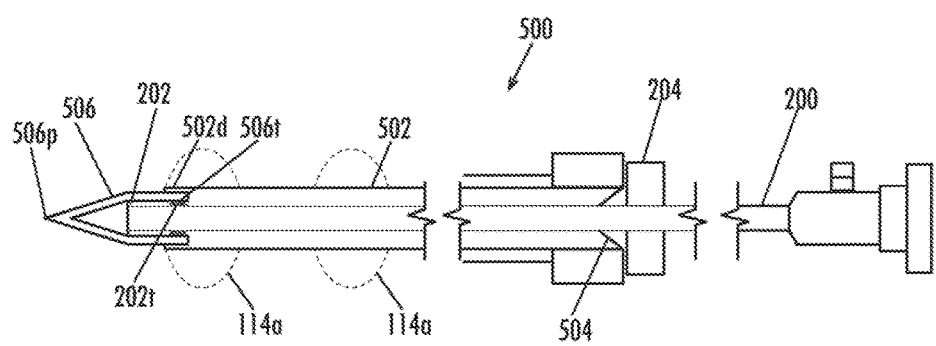
FIG. 19 illustrates an endoscopic trocar assembly configured to receive an endoscope therein for use as an instrument to visualize piercing through a tissue wall and gaining access to an interior chamber located inside the tissue wall.

FIG. 19 illustrates an endoscopic trocar assembly 500 configured to receive an endoscope 200 therein for use as an instrument to visualize piercing through a tissue wall 1 and gaining access to an interior chamber located inside the tissue wall 1. In one particular embodiment the instrument comprising the vocal assembly 500 with endoscope 200 inserted therein, as illustrated in FIG. 19, is used to gain entry into the left ventricle by piercing the tissue wall of the heart near the apex. It is noted that this instrument is not limited to this use, but can be used in similar manner to gain access and visualize the process of gaining access as the sharp distal tip of the instrument pierces through the tissue wall 1 of any of the organs, vessels, or tissues described above.

The endoscopic trocar assembly 500 includes a rigid trocar sleeve 502 typically having an outside diameter of about 5 mm to about 10 mm and in which a hemostatic valve 504 is provided in the annular space thereof, at a proximal end portion thereof. Optionally, the distal portion may be provided with expandable members 14a and 14b, shown in phantom lines in FIGS. 19 and 20A, in the expanded configurations in both views. The obturator inside the trocar 502 is formed by endoscope 200 having a distal, transparent tip covering the distal end 202 of the endoscope 200. Distal tip 506 is sharp at the distal end thereof and may form a pointed tip. For example, distal tip 506 may be conically tapering down to a sharp point 506p. The proximal end of trocar 502 functions as a stop when contacted by stop member 204 on endoscope 200 when endoscope 200 has been fully inserted into trocar 502. Tip 506 has an outside diameter smaller than the inside diameter of trocar 502 so that it is readily slidable through the trocar, and the majority of tip 506 extends distally of the distal end 502d of trocar 502 when endoscope 200 is fully inserted into trocar 502.

Likewise, the distal end 202 of endoscope 200 extends distally of the distal end 502d of trocar 502 in this configuration. The sharp, transparent distal tip 506 is attached to the distal end 202 of endoscope 200 such as by mating threads 506t, 202t, or other mechanical connection members, in any case, forming a fluid tight seal against the endoscope 200.

Figure 20A:
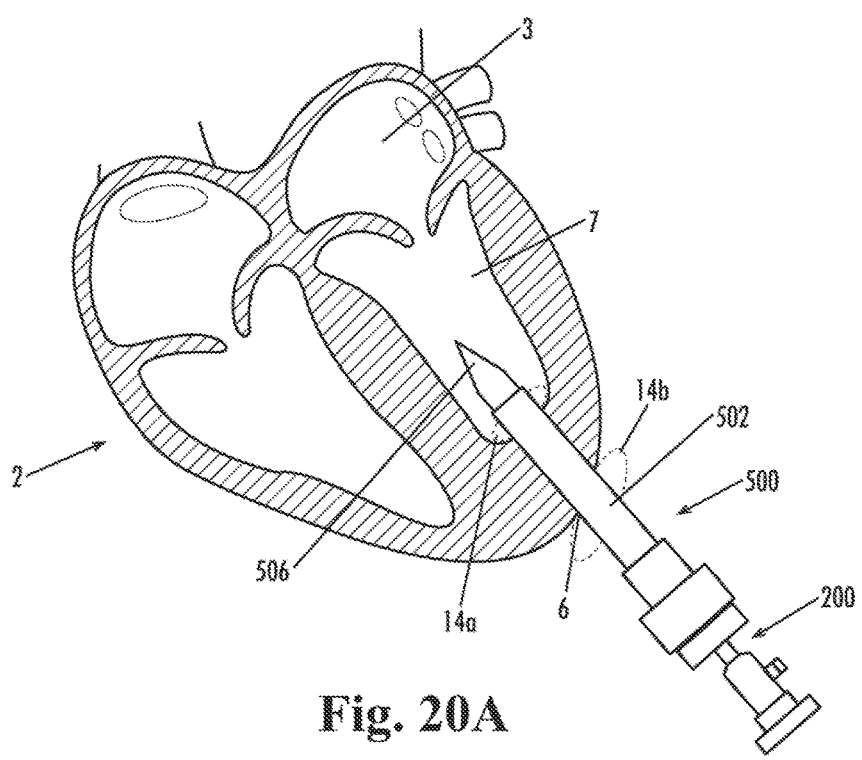
FIGS. 20A-20B illustrate steps of using the assembly and endoscope described with regard to FIG. 19.
Figure 20B:
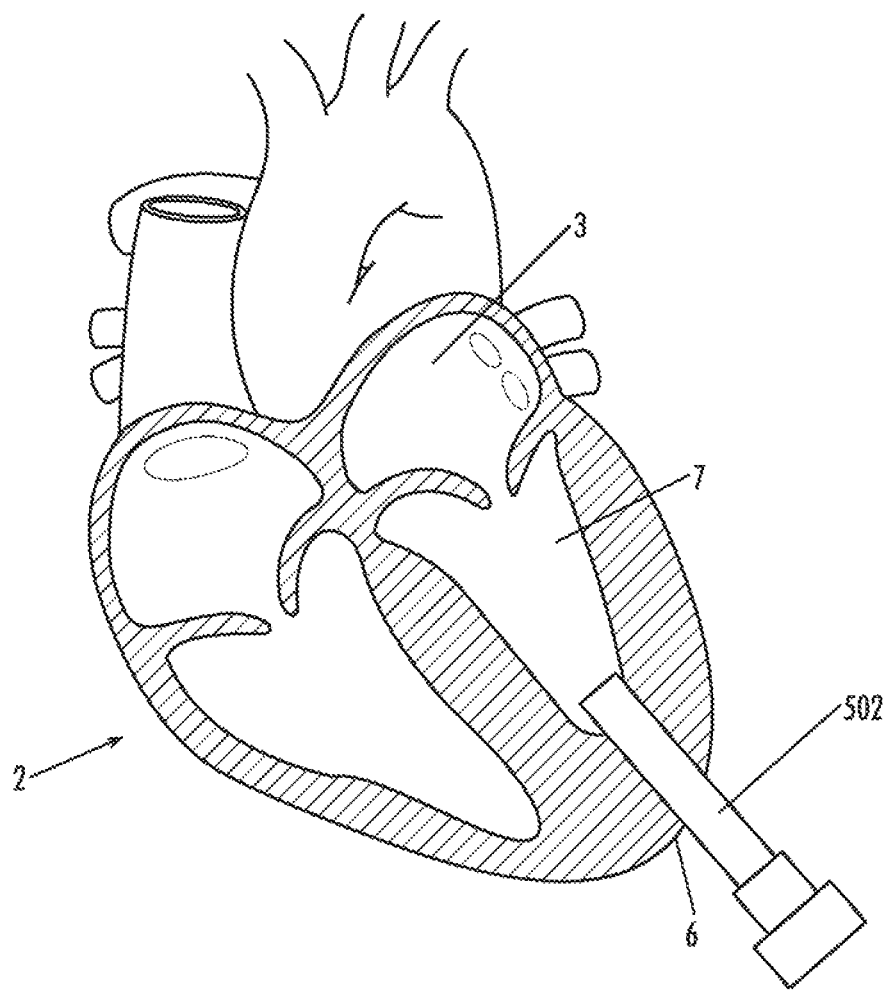

FIG. 20A illustrates use of the instrument comprising the endoscopic trocar assembly 500 and endoscope 200 to advance through the myocardium of the heart 2 at a location near the apex 6 of the heart to access the left ventricle 7. Following the creation of an opening through the skin of the patient such as in a manner described with regard to step 602 above, for example) and a pathway to the vicinity of the apex 6 of the heart 2, the instrument is delivered through the minimally invasive opening, aligned with a location near the apex 6 and driven into the myocardium to pierce the myocardial tissue wall with sharp tip 506. Visualization of the piercing of tip 506 through the myocardial wall can be accomplished through endoscope 200 and clear up 506. Upon visualization of blood via this visualization technique, this is confirmation that the myocardium has been pierced through and the endoscopic obturator (i.e., endoscope 200 and tip 506) is removed from trocar 502, leaving trocar 502 in place through the myocardial wall and into the ventricle 7, as illustrated in FIG. 20B. In the optional embodiment, where expandable members 14a and 14b are employed, these expandable members are provided in a compressed, compact configuration close to the trocar 502 as the trocar is inserted. Expandable member 14a may then be expanded/inflated and the trocar 502 can be retracted to pull expanded expandable member 14a into contact with the internal myocardial wall of the left ventricle near the apex. Expandable member 14b can then be expanded/inflated to form a hemostatic seal of the entry into the ventricle, together with expanded, expandable member 14a, as illustrated in FIG. 20A. Endoscope 200 may be withdrawn form trocar 502 either before or after expansion of the expandable members. Whether or not expandable members 14a,14b are used, instruments, tools and/or devices may then be introduced through trocar 502, with hemostatic valve 504 forming a hemostatic seal, substantially preventing outflow of blood/fluids from the ventricle. Instruments that can be inserted and used include, but are not limited to endoscopic balloon cannulae each having an operating channel through which surgical procedures can be performed on the endocardial surface and on the cardiac valves.

Figure 20C:
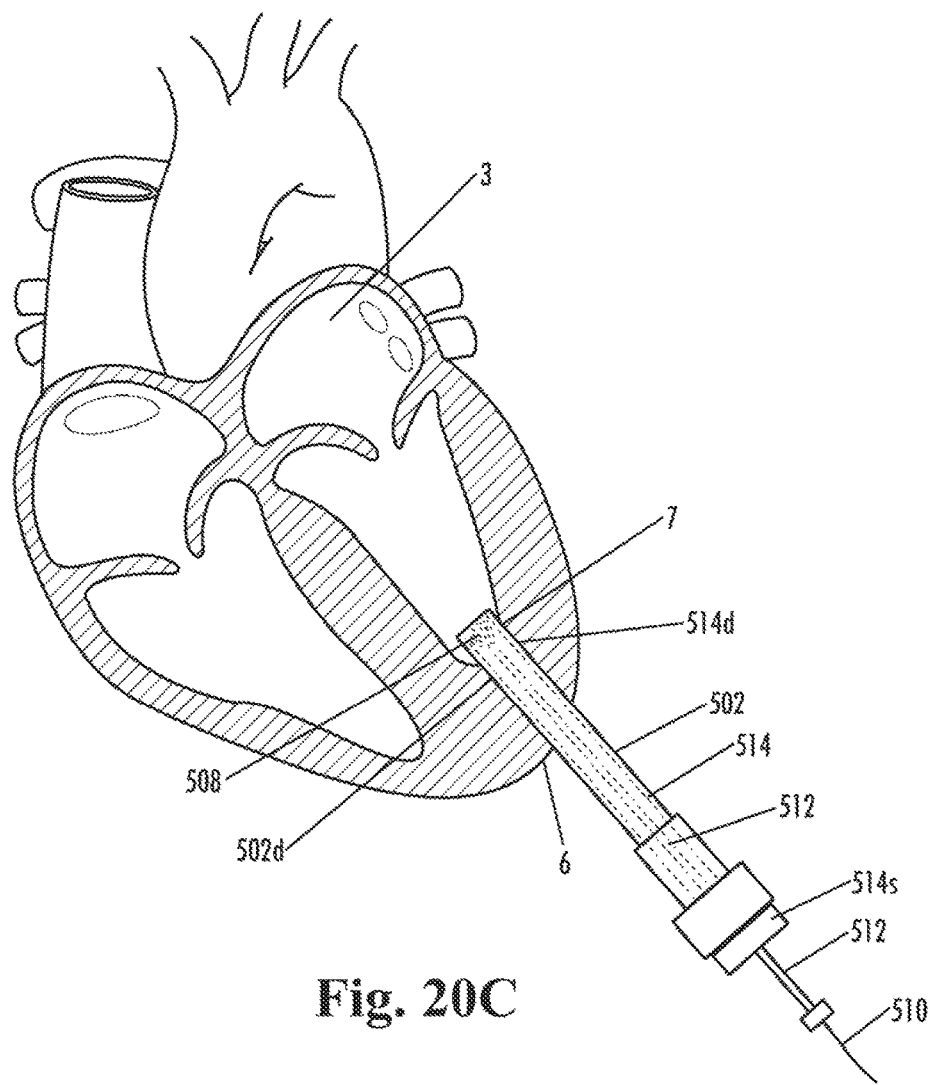
FIGS. 20C-20F illustrate using the trocar of FIG. 19 with the assembly of FIG. 21A to close the tract formed by the procedure of FIGS. 20A-20B.
Figure 21A:
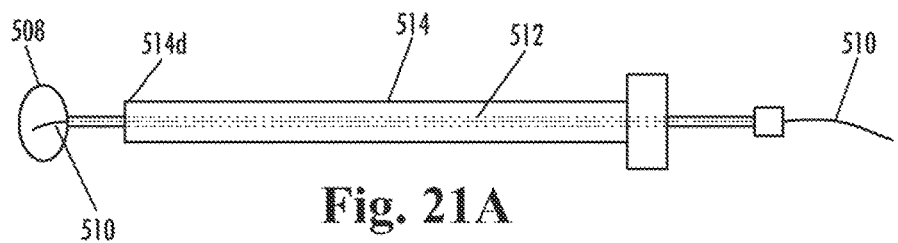
FIGS. 21A-21C illustrate an assembly useable in a minimally invasive procedure to seal a tract or opening through the wall of an organ vessel or other tissue.

Following performance of an endocardial procedure, a seal 508 is introduced to close the tract formed by the endoscopic trocar 502. FIG. 21A illustrates seal 508. Seal 508 may be constructed of a sheet of prosthetic graft material e.g., woven polyester or Dacron, and is attached to a suture 510 that may be nylon or polypropylene, for example. Suture 510 runs through the lumen of an inner tube 512 that is rigid and may have an outside diameter of about 1 mm to about 2 mm, for example. Inner tube 512 extends through an outer sleeve 514 having an outer diameter sized to form a slip fit inside endoscopic trocar cannula 502. The length of outer sleeve 514 is slightly longer than trocar 502 so that the distal end 514d extends slightly distally of the distal end 502d of vocal 502, when sleeve 514 is fully inserted into trocar 502 as illustrated in FIG. 20C. Sleeve 514 includes a stop 514s that abuts against, the proximal end of trocar 502 when sleeve 514 has been fully inserted into trocar 502.

Figure 20D:
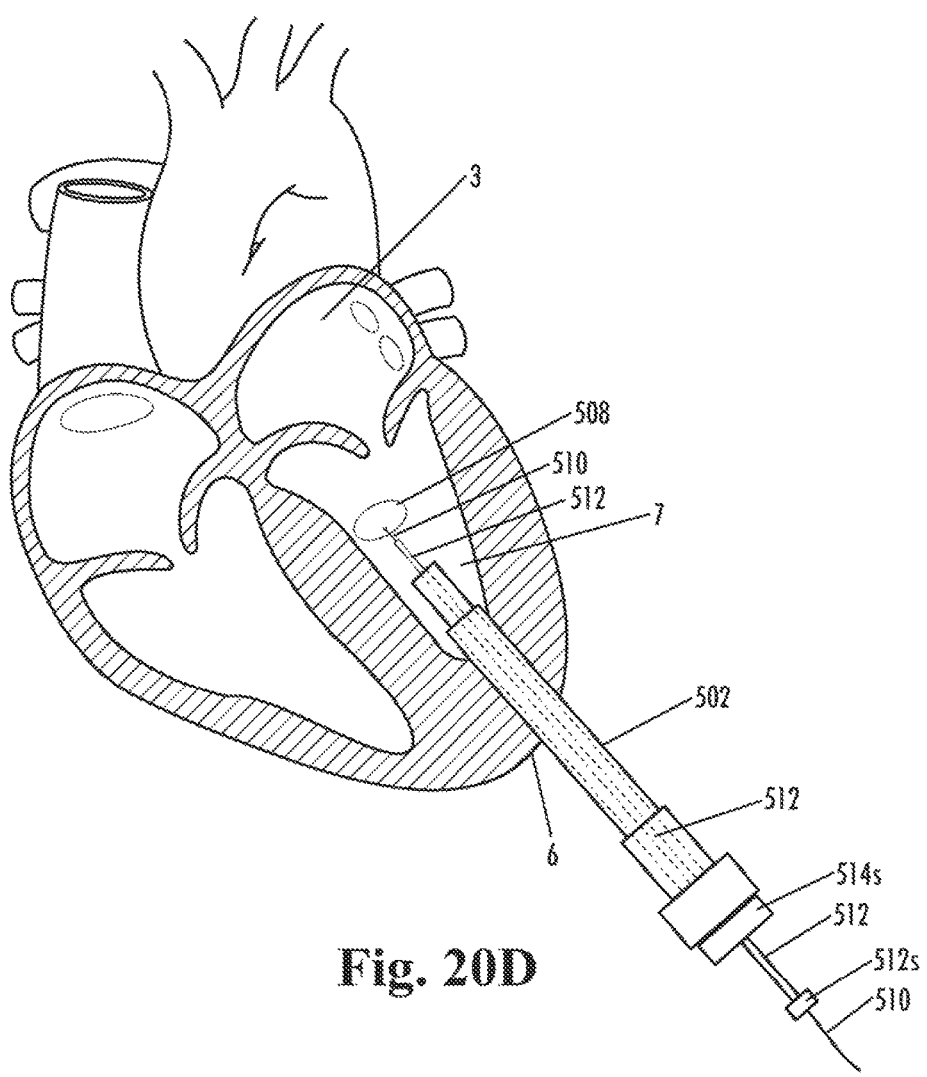
Figure 20E:
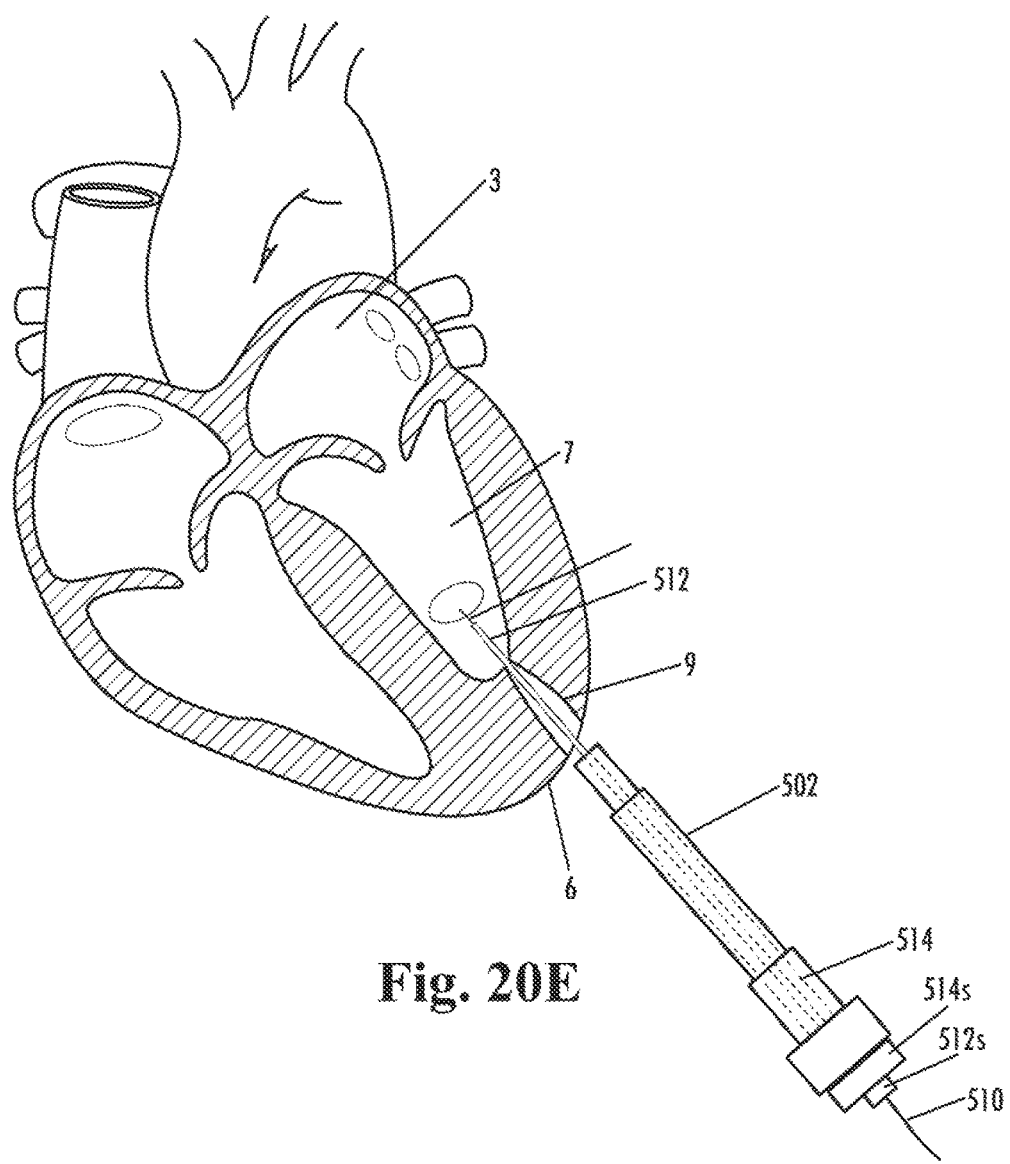
Figure 21B:
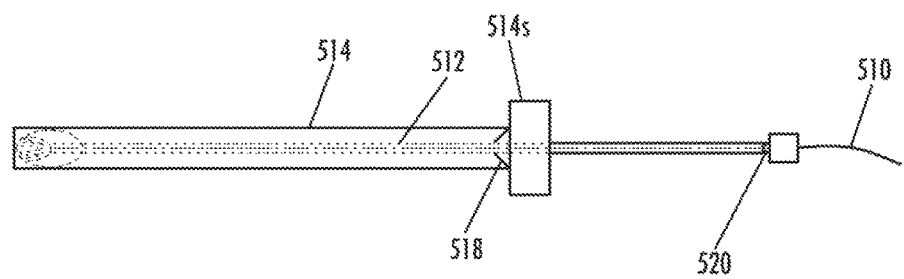
Figure 21C:
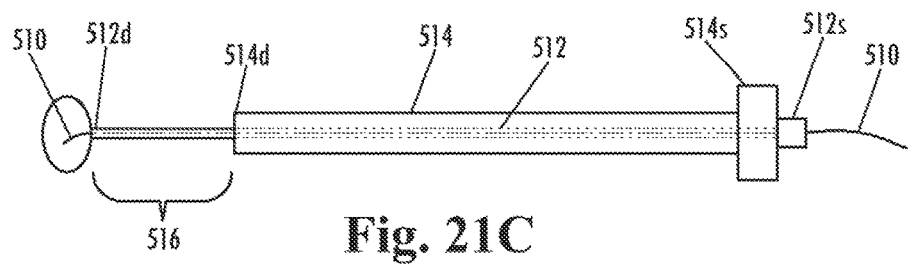

The length of inner tube 512 is selected so that when inner tube 512 is fully inserted into outer sleeve 514 (i.e., when stop 512s abuts stop 514 as shown in FIGS. 21C and 20E), the distal end 512d extends distally from distal end 514d by a distance that is greater than the thickness of the myocardium. Typically, this length should be selected so that seal 508 extends a distance 516 of about 6 cm distally of distal end 514d when inner tube 512 is fully inserted in sleeve 514 and seal 508 extends distally from, but contacts distal end 512d. A hemostatic valve or seal 518 in the proximal end portion of outer sleeve 514 allows inner tube 512 to slide with respect thereto while maintaining a fluid tight seal, and a hemostatic valve or seal 520 in the proximal end portion of inner tube 514 allows suture 510 to slide relative to inner tube 512 while maintaining a fluid tight seal (see FIG. 21B).

The inner tube 512 and suture 510 can be retracted relative to sleeve 514 to pull the seal into sleeve 514, as illustrated in FIG. 21B. In use, the sealing assembly is inserted into trocar 502 with the seal (or membrane seal) 508 in the retracted position, as shown in FIG. 20C. The inner tube 512 is next distally advanced by a predetermined distance (which can be indicated by an optionally placed mark on the outside of the inner tube 512 at a proximal portion thereof extending proximally from sleeve 514 to push seal 508 out of outer sleeve 514 and into the ventricle, as illustrated in FIG. 20D.

Figure 20F:
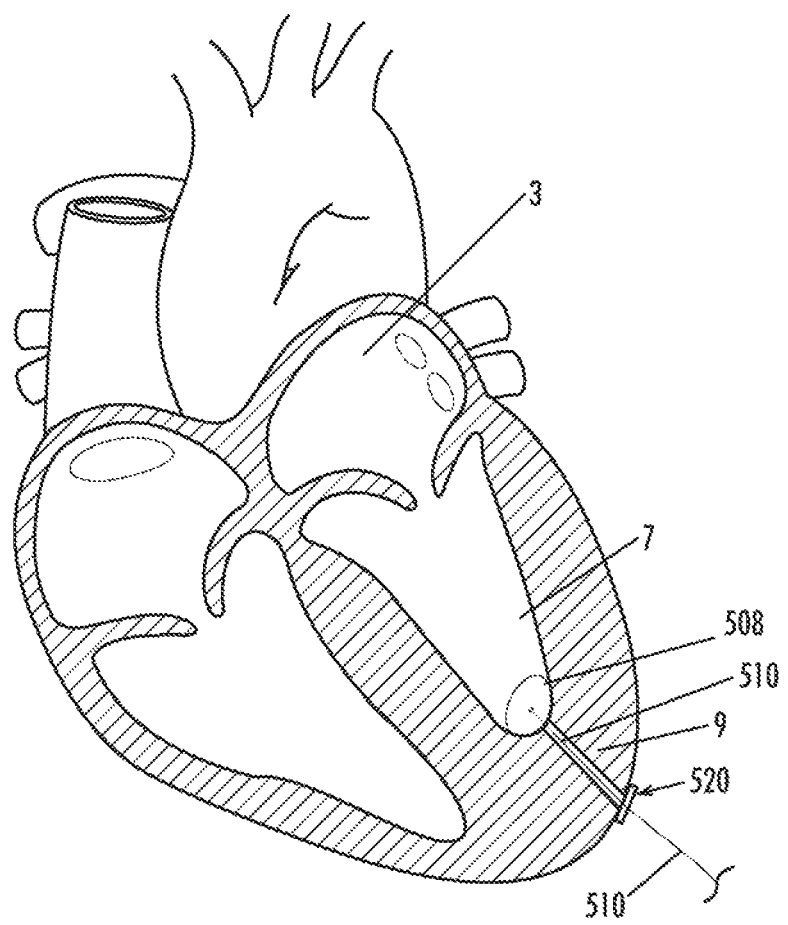
Figure 20G:
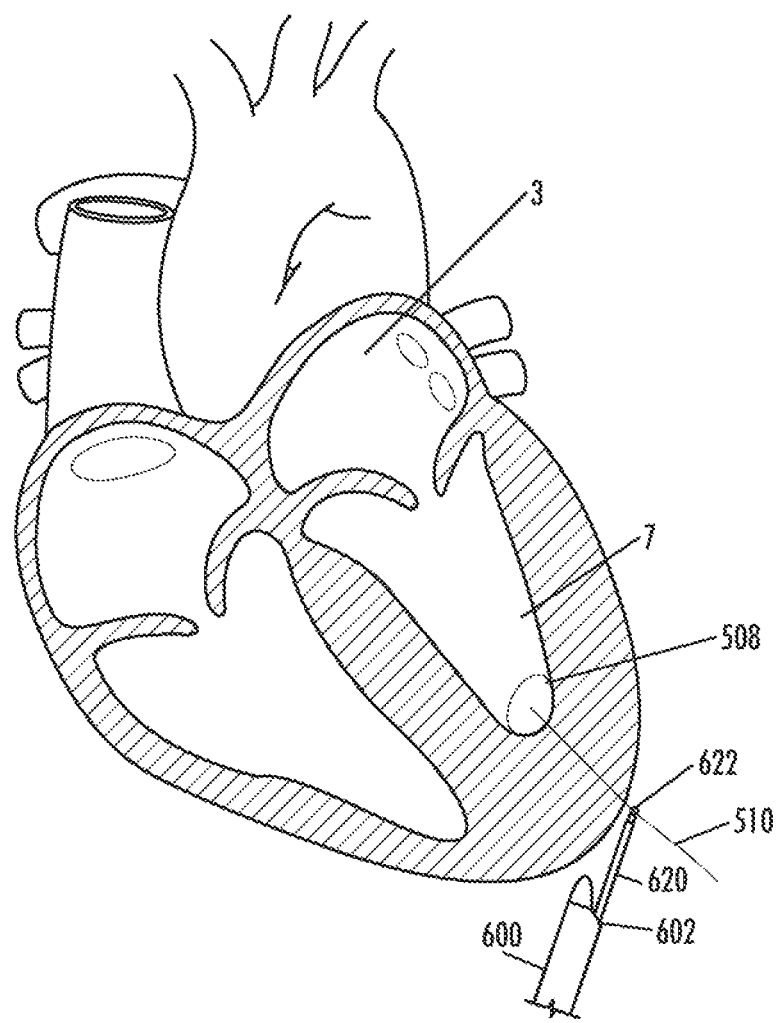
FIG. 20G illustrates use of a sliding suture loop inside a knot pusher to secure a seal against the inner wall of the left ventricle.

While holding inner tube 512 stationary relative to the heart 2, trocar 502 and outer sleeve 514 are next retracted proximally back to a position where stop 514s abuts stop 512s as shown in FIG. 20E, leaving only inner tube 512 inside the tract 9 vacated by trocar sleeve 502. This permits the tract 9 to shrink down to the size (inside diameter) about equal to the outside diameter of inner tube 512, thereby ensuring that seal 8 stays inside the ventricle 7 and is not pulled out through the trocar sleeve 502 or through a large diameter tract through the myocardium. After allowing the tract 9 to shrink down around inner tube 512, inner tube 512 is pulled out of tract 9 and out of the body (trocar 502 and sleeve 514 are also removed from the body, either at the same time as removal of inner tube 512 or just prior thereto), leaving seal 8 inside the ventricle 7 tethered to suture 510 which extends out of the body. A vascular clip 520 is placed on the outside wall of the ventricle 7 opposite seal 508 which is drawn against the inside, surface of the wall of the ventricle 7 as shown in FIG. 20F. Vascular clip may be advanced over suture 510 using an endoscopic clip applier advanced through the working channel 602 of an endoscopic visualization cannula 600 (e.g., Flex View from Boston Scientific Cardiac Surgery, Santa Clara Calif.). Alternatively, a sliding suture loop 622 inside a knot pusher tube 620 (similar to an Endoloop from Tyco Autosuture Corp., or the like) may be placed through the working channel 602 of endoscopic visualization channel 600, advanced over suture 510, cinched down on the outside wall of the ventricle 7 opposite seal 508, which is drawn against the insider surface of the wall of ventricle 7, see FIG. 20G. The tails of suture 510 and sliding suture loop 622 can be cut oil with endoscopic shears under visualization through use of endoscopic visualization cannula 600. Vascular clip 520 or cinched suture loop 622 thus maintains seal 508 compressed against the inner surface of the myocardial wall, thereby covering the tract 9, with seal 508 anchored in place to provide hemostasis to the ventricular tract 9.

Alternative to the use of a sheet of prosthetic graft material to form seal 508, seal 508 may be provided as a collagen plug that is installed to close and seal the tract formed by the endoscopic trocar 502. These embodiments of seal 508 can be placed in the same manner as described above with regard to placement of the seal made from a sheet of prosthetic graft material. However, rather than forming a seal over the inside wall surface of the wall in which the opening has been formed and which is being sealed off, these embodiments of seal are pulled at least partially into the opening (in a direction from the inside wall surface toward the outside wall surface) to wedge within the wall (myocardial wall or other wall having been pierced) in order to seal the opening. In the case of a trans-apical procedure on the heart, this provides post procedure: hemostasis.

Figure 22A:
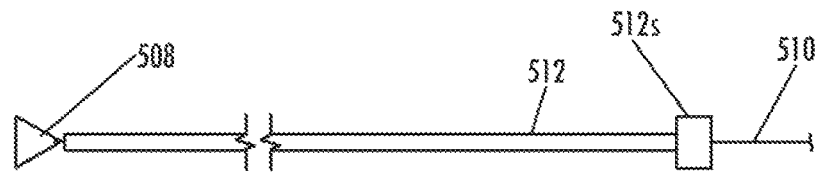
FIG. 22A illustrates a conical or wedge-shaped seal comprising collagen, connected to a suture which passes through an inner tube.
Figure 22B:
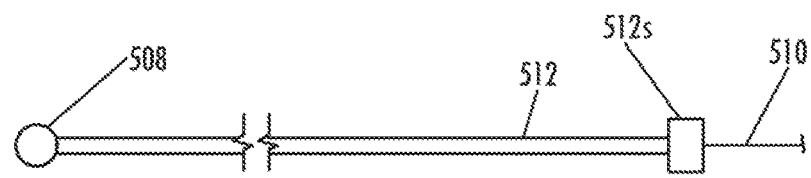
FIG. 22B illustrates a spherical or ball-shaped seal comprising collagen, connected to a suture which passes through an inner tube.

The collagen material from which seal 508 is made in these embodiments induced fibrotic growth into seal 508 and seal 508 also bio-absorbs over time, leaving a permanent tissue seal. FIG. 22A illustrates a conical or wedge-shaped seal 508 comprising collagen, as connected by suture 510 which passes through inner tube 512. For simplicity of illustration, outer sleeve 514 has not been shown in FIG. 22A, but would be used during installation of seal 508, as noted. FIG. 22B illustrates a spherical or ball-shaped seal 508 comprising collagen, as connected by suture 510 which passes through inner tube 512. For simplicity of illustration, outer sleeve 514 has not been shown in FIG. 223, but would be used during installation of seal 508, as noted.

Figures 23A, 23B:
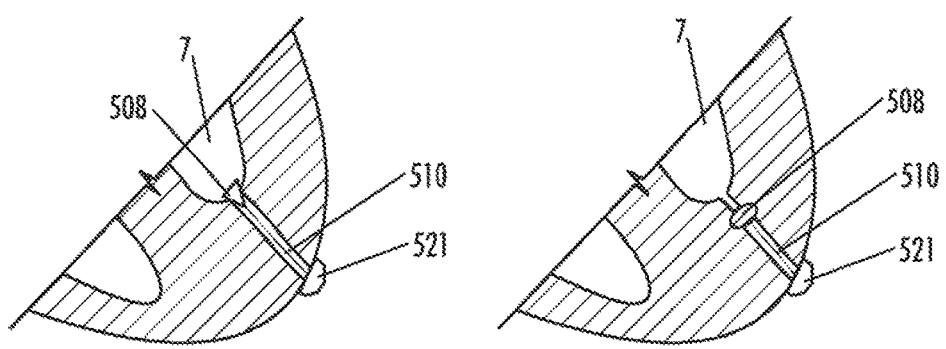
FIG. 23A illustrates a conical or wedge-shaped seal having been wedged into the opening in the myocardial wall to seal the opening.
FIG. 23B illustrates a spherical or ball-shaped seal inserted into the tract in the myocardial wall to seal the same.

FIG. 23A illustrates a conical or wedge-shaped seal 508 having been wedged into the opening in the myocardial wall to seal the opening. Alternatively, the seal 508 may be bullet-shaped and inserted in the same way. FIG. 23B illustrates a spherical or ball-shaped seal 508 inserted into the tract in the myocardial wall to seal the same. In these embodiments, suture or tether 510 may be made of a bioabsorbable material, so that the suture 510 bio-absorbs as well as the seal 508, thereby leaving a completely natural seal. These embodiments may be anchored in any of the same ways described above with the regard to the seals 508 made from a sheet of graft material. In the examples shown in FIGS. 23A and 23B, clip 521 has been anchored to suture 510 against the external surface of the myocardium, to prevent seal 508 from migrating out of the tract and into the left ventricle.

The present invention includes a port device for establishing a hemostatically sealed port through an opening in a tissue wall wherein an inside surface of the tissue wail interfaces with a fluid containing chamber, the device including: a cannula configured to be inserted through the opening in the tissue wall; and a first feature configured to impart an axial force on the tissue wall in a direction away from the fluid containing chamber, wherein axial force on the tissue wall forms a hemostatic seal substantially preventing fluid from escaping through the opening between said cannula and the opening.

In at least one embodiment, a second feature is configured to impart an axial force on the tissue wall in a direction opposing the axial force imparted by the first feature, wherein the tissue wall is axially compressed to form the hemostatic seal.

In at least one embodiment, the first feature comprises an expandable member configured to assume a collapsed configuration with a relatively smaller diameter, and an expanded configuration with a relatively larger diameter, wherein the expandable member expands radially away from the cannula upon expanding.

In at least one embodiment, the first feature comprises a first expandable member configured to assume a collapsed configuration with a relatively smaller diameter, and an expanded configuration with a relatively larger diameter, wherein the expandable member expands radially away from the cannula upon expanding, and wherein the second feature comprises a second expandable member configured to assume a collapsed configuration with a relatively smaller diameter, and an expanded configuration with a relatively larger diameter, wherein the second expandable member expands radially away from the cannula upon expanding; and wherein the first expandable member is located around a distal end portion of the cannula and the second expandable member is located proximally adjacent the first expandable member such that expansion of the first and second expandable members when positioned on opposite sides of the tissue wall axially compresses the tissue wall.

In at least one embodiment, the first and second expandable members comprise first and second balloons.

In at least one embodiment the cannula is rigid.

In at least one embodiment, the first and second balloons are interconnected by a thin, flexible tubular sheath, and the cannula is insertable though central openings formed in the first and second balloons and through the tubular sheath.

In at least one embodiment, the first and second features comprise elastomeric foam, wherein the first and second features are extendable along the cannula in a first configuration having a relatively smaller diameter and wherein the first and second features are configurable to a second, expanded configuration wherein each of the first and second features assume a relatively larger diameter, wherein the first and second features expand radially away from the cannula.

In at least one embodiment, at least one actuator is provided for axially compressing the first and second features to move from the first configuration to the second, expanded configuration.

In at least one embodiment, the first feature is located around a distal end portion of the cannula and the second feature is located proximally adjacent the first feature such that expansion of the first and second features when positioned on opposite sides of the tissue wall axially compresses the tissue wall.

In at least one embodiment, a closure assembly, configured to close the opening after removal of the cannula, is provided.

In at least one embodiment, the closure assembly comprises a double-ended wire having barbs at both ends and configured to be delivered through the cannula, the barbs being drivable though the tissue wall in a direction from the inside surface to the outside surface.

In at least one embodiment, a locking ring is slidable into detents provided on the wire of the closure assembly to maintain the barbs in a configuration holding tissue edges around the opening in a closed, everted orientation.

In at least one embodiment, a pusher element is attachable to the wire and has a length greater than a length of the cannula, and the pusher element is sufficiently rigid to push the wire through the cannula.

In at least one embodiment, a seal member extending over the cannula and surrounds the fast feature.

In at least one embodiment, the first feature comprises screw threading on a distal end portion of the cannula, and the second feature comprises an expandable member configured to assume a collapsed configuration with a relatively smaller diameter, and an expanded configuration with a relatively larger diameter, wherein the second expandable member expands radially away from the cannula upon expanding.

An assembly for establishing a hemostatically sealed port through an opening in a tissue wall is provided, wherein an inside surface of the tissue wall interfaces with a fluid containing chamber, and the assembly comprises: a port device including a cannula having a biocompatible material on a distal end portion thereof that fuses or adheres to the tissue wall at the perimeter of the opening when heated, and a trocar having a sharp distal tip heatable to a temperature to at least partially melt tissue of the tissue wall as it is advanced therethrough, wherein the trocar is slidable through the cannula.

An assembly for establishing a hemostatically sealed port through an opening in a tissue wall is provided, wherein an inside surface of the tissue wall interfaces with a fluid containing chamber, and the assembly comprises: a port device including a cannula configured to be inserted through the opening in the tissue wall and a first feature configured to impart an axial force on the tissue wall in a direction away from the fluid containing chamber, wherein axial force on the tissue wall forms a hemostatic seal substantially preventing fluid from escaping through the opening between the cannula and the opening; and a dilator insertable through the cannula and having a sharp distal tip, wherein the sharp tip of the dilator is adapted to form the opening through the tissue and wherein the dilator dilates the opening formed by the sharp tip and the cannula is advanced through the dilated opening together with the dilator.

In at least one embodiment, the dilator is removably attachable within the cannula.

In at least one embodiment, the port device further comprises a second feature configured to impart an axial force on the tissue wall in a direction opposing the axial force imparted by the first feature, wherein the tissue wall is axially compressed to form the hemostatic seal.

In at least one embodiment, the first feature comprises a first expandable member configured to assume a collapsed configuration with a relatively smaller diameter, and an expanded configuration with a relatively larger diameter, wherein the expandable member expands radially away from the cannula upon expanding: wherein the second feature comprises a second expandable member configured to assume a collapsed configuration with a relatively smaller diameter, and an expanded configuration with a relatively larger diameter, wherein the second expandable member expands radially away from the cannula upon expanding; and wherein the first expandable member is located around a distal end portion of the cannula and the second expandable member is located proximally adjacent the first expandable member such that expansion of the first and second expandable members when positioned on opposite sides of the tissue wall axially compresses the tissue wall.

In at least one embodiment, the first and second expandable members comprise first and second balloons.

An assembly for establishing a hemostatically sealed port through an opening in a tissue wall is provided, wherein an inside surface of the tissue wall interfaces with a fluid containing, chamber, and the assembly comprises: a port device including first and second annularly shaped balloons interconnected by a thin, flexible tubular sheath; and an inserter having a sharp distal tip for creating the opening through the tissue wall; wherein the first and second balloons and the tubular sheath are wrappable around the introducer to provide a first compact configuration having a reduced cross-sectional area, and wherein, upon creating the opening with the distal tip and inserting a distal end portion of the introducer and the first balloon through the tissue wall, the first and second balloons are inflatable to expand to a second, expanded configuration that unwraps the first and second balloons and the sheath, and wherein the first and second balloons axially compress the tissue wall.

In at least one embodiment, a cannula is insertable through the second balloon, the tubular sheath and the first balloon in the second, expanded configuration.

In at least one embodiment the cannula is rigid.

An assembly for establishing a hemostatically sealed port through an opening in a tissue wall is provided, wherein an inside surface of the tissue wall interfaces with a fluid containing chamber, and the assembly comprises: a port device including a first expandable portion and a second expandable portion; a rigid cannula; and an introducer having a sharp distal tip for creating the opening through the tissue wall; wherein the first expandable portion is placed in a compact configuration over a distal end portion of the introducer and the second expandable portion is placed in a compact configuration over a distal end portion of the cannula; and wherein, upon creating the opening with the distal tip and inserting the distal end portion of the introducer and the first expandable portion through the tissue wall, the first and second expandable portions are expanded to a second, radially expanded configuration wherein the first and second expandable portions axially compress the tissue wall.

In at least one embodiment, the introducer is removed after the expansion of the expandable portions, leaving the port device forming a hemostatically sealed port through the tissue wall.

A port device for establishing a hemostatically sealed port through an opening in a tissue wall is provided, wherein an inside surface of the tissue wall interfaces with a fluid containing chamber, and the device comprises: a first feature configured to impart an axial force on the tissue wall in a direction away from the fluid containing chamber; and a second feature configured to impart an axial force on the tissue wall in a direction opposing the axial force imparted by the first feature, wherein the tissue wall is axially compressed to form the hemostatic seal.

In at least one embodiment, the first feature comprises a resilient, self-expanding ring.

In at least one embodiment, the ring comprises a super-elastic material.

In at least one embodiment, the second feature comprises a plurality of flexible arms attached to the first feature and adapted to extend through the opening.

In at least one embodiment, the flexible arms each comprise an attachment feature adapted to attach the flexible arms, respectively to an outer surface of the tissue wall.

In at least one embodiment, the attachment features comprise adhesive,

In at least one embodiment, a thin film extends across the ring and forms a seal therewith.

In at least one embodiment, the film comprises a slit therethrough.

A closure device for closing an opening in a tissue wall is provided, wherein an inside surface of the tissue wall interfaces with a fluid containing chamber, and the device is deliverable through a cannula and closure is performed as a minimally invasive: procedure. The device includes a double-ended wire having barbs at both ends and configured to be delivered through the cannula, the barbs being drivable though the tissue wall in a direction from the inside surface to the outside surface; and a locking ring slidable into detents provided on the wire to maintain the barbs in a configuration holding tissue edges around the opening in a closed, everted orientation.

In at least one embodiment, a pusher element is attachable to the wire and has a length greater than a length of the cannula, and the pusher element is sufficiently rigid to push the wire through the cannula.

A port device for establishing a hemostatically sealed port through an opening in a tissue wall is provided, wherein an inside surface of the tissue wall interfaces with a fluid containing chamber, and the device comprises: first and second rollers extending substantially parallel to one another and mechanically linked to allow separation thereof to increase a space therebetween and movement together to reduce the space; and at least one scallop provided in each roller, wherein the rollers are rotatable to align the scallops to form an opening aligned with the opening in the tissue wall, and wherein the rollers are further rotatable to align cylindrical surfaces thereof with each other to close the opening in the tissue wall and form a hemostatic seal.

In at least one embodiment, the rollers are resiliently biased toward one another.

A port device for establishing a hemostatically sealed port through an opening in a tissue wall is provided, wherein an inside surface of the tissue wall interfaces with a fluid containing chamber, and the device comprises: a cannula having a closable distal end portion, the distal end portion comprising a plurality of spring-biased clamshell doors openable to allow an instrument to be passed therethrough, the clamshell doors being spring-biased to a closed configuration.

In at least one embodiment, the distal end portion is bullet-shaped when the clamshell doors are in the closed configuration.

A port device for establishing a hemostatically sealed port through an opening in a tissue wall is provided, wherein an inside surface of the tissue wall interfaces with a fluid containing chamber, and the device comprises, a plug having a central annulus extending therethrough along a longitudinal axis of the plug; a channel formed circumferentially in and around an external portion of the plug and compression members configured to compress the plug to expand the channel into contact with wall edges of an opening through a tissue wall.

An assembly usable in performing minimally-invasive ablation procedures is provided that includes: an elongated shaft, a balloon fitted over a distal end of the elongated shaft, the balloon being configured to assumed a deflated configuration, as well as an inflated configuration wherein the balloon has an outside diameter greater than an outside diameter of the balloon in the deflated configuration; and a halo comprising wires configured to be positioned proximal of the balloon in a retracted configuration and movable to a position distal of the balloon in an expanded configuration, wherein, when in the expanded configuration, the halo defines an area larger than a contracted area defined by the halo when in the retracted configuration.

In at least one embodiment, the halo is advanceable over the balloon when the balloon is in the inflated configuration.

In at least one embodiment, the halo comprises superelastic wires that expand a configuration of the halo when moving from the retracted configuration to the expanded configuration.

In at least one embodiment, the superelastic wires slide over the balloon and the balloon deforms somewhat as the halo passes from the retracted configuration to deploy over the balloon to the expanded configuration.

In at least one embodiment, a plurality of push rods are connected to the halo, the push rods being axially slidable relative to the shaft to move the halo from the retracted configuration position and the deployed, expanded configuration position and vice versa.

In at least one embodiment, an actuator is connected to proximal ends of the push rods, the actuator being slidable over the shaft.

In at least one embodiment, the actuator comprises an extension extending proximally to a proximal end portion of the shaft.

In at least one embodiment, the halo is electrically connectable to a source of ablation energy proximal of the assembly.

In at least one embodiment, the halo is connectable to a source of ablation energy proximal of the assembly.

In at least one embodiment, a conduit connecting with the balloon extends proximally of a proximal end of the shalt the conduit being connectable in fluid communication with a source of pressurized fluid.

In at least one embodiment, the shaft comprises a cannula, the cannula being configured and dimensioned to receive an endoscope shaft therein, with a distal tip of the endoscope being positionable within the balloon.

In at least one embodiment, the shaft comprises a shaft of an endoscope.

In at least one embodiment, the halo is formed of two wires and forms a substantially oval shape when in the expanded configuration.

In at least one embodiment, the halo forms an encircling shape when in the expanded configuration.

In at least one embodiment, the halo is formed of four wires and forms a substantially quadrilateral shape when in the expanded configuration.

An instrument usable in performing minimally-invasive ablation procedures is provided that includes: an elongated shaft a balloon fitted over a distal end of the elongated shaft, the balloon being configured to assume a deflated configuration, as well as an inflated configuration wherein the balloon has an outside diameter greater than an outside diameter of the balloon in the deflated configuration; and a halo comprising wires configured to be positioned proximal of the balloon in a retracted configuration and movable to a position distal of the balloon in an expanded configuration, wherein, when in the expanded configuration, the halo defines an area larger than a contracted area defined by the halo when in the retracted configuration; and an endoscope having a distal tip thereof positioned adjacent to an opening of the balloon or within the balloon.

In at least one embodiment, the shaft comprises a shaft of the endoscope.

In at least one embodiment, the shaft comprises a cannula and wherein a shaft of the endoscope is received in the cannula.

In at least one embodiment, the halo is advanceable over the balloon when the balloon is in the inflated configuration.

In at least one embodiment, the halo comprises superelastic wires that expand a configuration of the halo when moving from the retracted configuration to the expanded configuration.

In at least one embodiment, the superelastic wires slide over the balloon and the balloon deforms somewhat as the halo passes from the retracted configuration to deploy over the balloon to the expanded configuration.

In at least one embodiment, a plurality of push rods are connected to the halo, the push rods being axially slidable relative to the shaft to move the halo from the retracted configuration position and the deployed, expanded configuration position and vice versa.

In at least one embodiment, an actuator is connected to proximal ends of the push rods, the actuator being slidable over the shaft.

In at least one embodiment, the actuator comprises an extension extending proximally to a proximal end portion of the endoscope.

In at least one embodiment, the halo is electrically connectable to a source of ablation energy proximal of the instrument.

In at least one embodiment, the halo is connectable to a source of ablation energy proximal of the instrument.

In at least one embodiment, a conduit connecting with the balloon extends proximally of a proximal end portion of the shaft, the conduit being connectable in fluid communication with a source of pressurized fluid.

In at least one embodiment, the halo is formed of two wires and forms a substantially oval shape when in the expanded configuration.

In at least one embodiment, the halo forms an encircling shape when in the expanded configuration.

In at least one embodiment, the halo is formed of four wires and forms a substantially quadrilateral shape when in the expanded configuration.

An instrument facilitating the making of an opening, by endoscopic techniques, through a tissue wall is provided, wherein an inside surface of the tissue wall interfaces with a fluid containing chamber, while directly visualizing the making of the opening, the instrument comprising: a rigid trocar sleeve; and an endoscope slidable within the trocar sleeve and fitted with a transparent, sharp tip over a distal end of the endoscope, wherein the transparent, sharp tip is also slidable within the trocar.

In at least one embodiment, a stop is provided on a shaft of the endoscope, wherein, when the endoscope is inserted into the trocar sleeve to an extent where the stop abuts a proximal end of the trocar sleeve, the distal end of the endoscope and the transparent sharp tip are positioned distally adjacent a distal end of the trocar sleeve.

A sealing assembly for closing, an opening, by endoscopic techniques, through a tissue wall is provided, wherein an inside surface of the tissue wall interfaces with a fluid containing chamber, and the assembly comprises: a seal, an inner tube; a suture attached to the seal and extending through the inner tube, the suture have sufficient length to extend proximally of the inner tube when the seal is positioned distally of a distal end of the inner tube: and an outer sleeve configured to allow the inner tube to be advanced therethrough.

In at least one embodiment, the inner tube is rigid.

In at least one embodiment, the seal comprises woven polyester or Dacron.

In at least one embodiment, the seal has a surface area larger than an area of the opening to be closed.

In at least one embodiment, the suture comprises at least one of nylon and polypropylene.

In at least one embodiment, a trocar sleeve is provided, wherein the outer sleeve has an outside diameter sized to form a slip fit inside the trocar sleeve.

In at least one embodiment, the outer sleeve has a length greater than a length of the trocar sleeve.

In at least one embodiment the trocar sleeve is rigid.

In at least one embodiment, the inner tube has a length greater than a length of the outer sleeve.

In at least one embodiment, the inner tube comprises a stop on a proximal end portion thereof, wherein when the inner tube is inserted into the outer sleeve to an extent where the stop abuts a proximal end of the outer sleeve, a distal end of the inner tube extends distally of a distal end of the outer sleeve by a predetermined distance that is greater than a thickness of the tissue wall.

In at least one embodiment, the predetermined distance is about 6 cm.

In at least one embodiment, the suture and the inner tube are retractable, relative to the outer sleeve, to draw the seal into a distal end portion of the outer sleeve.

In at least one embodiment, the seal is deformed when it is drawn into the distal end portion of the outer sleeve.

A method of establishing a hemostatically sealed port through an opening in a tissue wall is provided, wherein an inside surface of the tissue wall interfaces with a fluid containing chamber, the method including the steps of: providing a minimally invasive opening through the skin of a patient; advancing a sharp instrument, through the minimally invasive opening to the tissue wall: establishing an opening through the tissue wall, by manipulating the instrument from outside of the patient; and installing a port device though the opening in the tissue wall and forming a hemostatic seal between the port device and the opening, by manipulations performed by an operator outside of the patient.

In at least one embodiment, the installing comprises inserting a distal end portion of the port device including a distal end portion of a cannula and a first expandable member through the opening through the tissue wall to position the first expandable member inside of an inside surface of the tissue wall; and expanding the first expandable member.

In at least one embodiment, a second expandable member is expanded at a location outside of an outside surface of the tissue wail, wherein the first and second expandable members axially compress the tissue wall.

In at least one embodiment, the first expandable member is an inflatable balloon.

In at least one embodiment, the first expandable member comprises polymer foam.

In at least one embodiment, the first expandable member comprises an expandable stent.

In at least one embodiment, the second expandable member is an inflatable balloon.

In at least one embodiment, the second expandable member comprises polymer foam.

In at least one embodiment, the second expandable member comprises an expandable stent.

In at least one embodiment, at least one surgical procedure is performed through the tissue wall by inserting at least one tool, instrument or device through the port device and manipulating the at least one tool, instrument or device from a location outside of the patient.

In at least one embodiment, the tissue wall is a tissue wall of an atrial appendage.

In at least one embodiment, the atrial appendage is the left atrial appendage.

In at least one embodiment, the tissue wall is a myocardial wall of the heart of the patient.

In at least one embodiment, the opening is made in the myocardial wall at or near the apex of the heart, providing access to the left ventricle.

In at least one embodiment, a proximal end portion of the cannula extends out of the patient, through the minimally invasive opening through the skin, after the step of installing the device to form the hemostatic seal.

In at least one embodiment, the step of establishing an opening through the tissue wall comprises piercing the tissue wall and dilating the tissue wall with a dilator, and wherein a portion of the port device, following the dilator is inserted through the opening through the tissue walk after which the dilator is removed.

In at least one embodiment, the step of establishing an opening through the tissue wall comprises piercing the tissue wall with a sharp tip of an inserter, and wherein first and second expandable members are compressed and wrapped around the inserter, wherein the installing the port device comprises inserting the first expandable member through the opening through the tissue wall, expanding the first expandable member inside of the tissue wall, expanding the second expandable member outside of the tissue wall, and withdrawing the inserter.

In at least one embodiment, a rigid cannula is inserted through annular openings in the first and second expanded expandable members.

In at least one embodiment, the step of establishing an opening through the tissue wall comprises piercing the tissue wall with a sharp tip of an inserter, and wherein a first expandable members is placed, in a non-expanded configuration over a distal end portion of the inserter, and a second expandable member is placed, in a non-expanded configuration over a distal end of a cannula, and wherein the installing the port device comprises inserting the distal end portion of the inserter and first expandable, member through the opening through the tissue wall, expanding the first expandable member inside of the tissue wall, expanding the second expandable member outside of the tissue wall, and withdrawing the inserter.

In at least one embodiment, the step of establishing an opening through the tissue wall comprises piercing the tissue wall with a sharp tip of an inserter, and wherein an expandable member is placed, in a non-expanded configuration over a distal end portion of the inserter, and wherein the installing the port device comprises inserting the distal end portion of the inserter and a first expandable portion of the expandable member through the opening through the tissue wall, expanding the first expandable portion inside of the tissue wall, expanding a second expandable portion of the expandable member outside of the tissue wall, and withdrawing the inserter.

In at least one embodiment, a rigid cannula is inserted through annular openings in the first and second expanded expandable portions.

In at least one embodiment, the step of installing comprises inserting a resilient ring portion of the port device, while in a reduced size configuration through the opening through the tissue wall: allowing the resilient ring to expand to an expanded configuration; drawing the ring against an inner surface of the tissue wall, and fixing a plurality of arms attached to the ring and extending through the opening in the tissue wall to an outer surface of the tissue wall.

In at least one embodiment, the step of installing comprises placing a pair of rollers on the tissue wall, against an outer surface thereof on opposite sides of the opening through the tissue wall; and compressing a double thickness of the tissue wall together by relative movement of the rollers toward one another.

In at least one embodiment, the rollers are rotated to align scallops provided in both rollers, thereby allowing access through the opening via an opening between the rollers provided by the scallops.

In at least one embodiment, the step of installing comprises placing a pair of rollers on the tissue wall, against an outer surface thereof on opposite sides of a target location where the opening through the tissue will is to be formed, compressing a double thickness of the tissue wall together by relative movement of the rollers toward one another; rotating the rollers to align scallops provided in both rollers, thereby allowing access to the tissue wall by the sharp instrument to form the opening through the tissue wall.

In at least one embodiment, a sealing member is sealed on an outer surface of the tissue wall, to establish a sealed working space: prior to at least one of: the establishing an opening through the tissue wall and the installing a port device though the opening.

In at least one embodiment, the step of installing comprises inserting a closable, bullet-shaped distal end of a cannula through the opening through the tissue wall, wherein the bullet-shaped distal end is pushable open by inserting a tool, instrument or device through the cannula, and is spring biased to automatically close when no tool, instrument or device is positioned between portions of the openable distal end, thereby hemostatically sealing the distal end.

In at least one embodiment, an ablation procedure is performed on an endocardial surface of the left atrium.

In at least one embodiment, at least one instrument is inserted into the left ventricle.

A method of performing ablation by minimally invasive methods while directly visualizing the ablation procedure is provided, including the steps of: advancing an instrument through a minimally invasive opening through the skin of a patient and through an opening through a tissue wall to enter a fluid containing chamber against an inner surface of which ablation is to be performed; expanding a balloon at a distal end of the instrument; contacting the expanded balloon against an inner surface of a wall of the chamber, visualizing the inner surface of the wall of the chamber in a location contacted; identifying a target location to ablate by the contacting and visualizing steps, while intermittently moving the balloon to contact different locations, if necessary until the target location is identified; advancing a halo over the balloon to position the halo around an identified location and against the target location to be ablated, between the target location and a distal surface of the balloon; and applying ablation energy though the halo while visualizing the halo and target location through the balloon.

In at least one embodiment, the chamber is the left atrium, the identified location is at least one pulmonary vein ostium, and the target location is an inside surface of the atrial wail surrounding the at least one pulmonary vein ostium.

In at least one embodiment, the step of applying ablation energy forms an encircling lesion in the tissue at the target location.

In at least one embodiment, the opening through the tissue wall includes a port, device installed therethrough forming a hemostatic seal between the port device and the opening, and wherein the instrument is inserted, through the port device.

In at least one embodiment, the instrument is removed from the patient, and the method further includes: advancing a second instrument through the minimally invasive opening through the skin of the patient and through the opening through the tissue wall to enter the chamber; expanding a balloon at a distal end of the second instrument; contacting the expanded balloon against an inner surface of a wall of the chamber to locate a lesion formed by the applying ablation energy; visualizing the lesion through the balloon contacting the lesion aligning an ablation element on a distal surface of the balloon to contact the lesion; applying ablation energy though the ablation element, while dragging the ablation element along tissue to form a linear lesion; and visualizing movement of the ablation element and formation of the linear lesion as the ablation element is dragged and ablation energy is applied.

A method of performing ablation by minimally invasive methods while directly visualizing the ablation procedure is provided, including the steps of: advancing an instrument through a minimally invasive opening through the skin of a patient and through an opening through a tissue wall to enter a fluid containing chamber against an inner surface of which ablation is to be performed; expanding a balloon at a distal end of the instrument; contacting the expanded balloon against an inner surface of a wall of the chamber; visualizing the inner surface of the wall of the chamber in a location contacted; identifying a target location to ablate by the contacting and visualizing steps, while intermittently moving the balloon to contact different locations, if necessary until the target location is identified; aligning an ablation element, on a distal surface of the balloon to contact the target location; applying ablation energy though the ablation element, while dragging the ablation element along tissue to form a linear lesion; and visualizing movement of the ablation element and formation of the linear lesion as the ablation element is dragged and ablation energy is applied.

A method of establishing, by endoscopic techniques, an opening through a tissue wall wherein an inside surface of the tissue wall interfaces with a fluid containing chamber, while visualizing the establishment of the opening, is provided, including the steps of: providing a minimally invasive opening through the skin of a patient, advancing an instrument including an endoscope having a sharp, transparent tip mounted on a distal end thereof, and a trocar, wherein the endoscope is slidably received in the trocar and the tip extends distally from a distal end of the trocar, through the minimally invasive opening to the tissue wall; and driving the sharp, transparent tip through the tissue wail while visualizing the passage of the sharp, distal tip into the tissue wall and through the wall, where the fluid is visualized, visualization being performed through the endoscope.

In at least one embodiment, the endoscope and sharp tip are withdrawn from the patient, leaving the trocar installed through the tissue wall to function as a port.

In at least one embodiment, a proximal end portion of the trocar extends out of the patient, through the minimally invasive opening through the skin when a distal end portion of the trocar is inserted through the tissue wall.

In at least one embodiment, at least one surgical procedural step is carried out that includes advancing at least one of a tool, instrument or device through the trocar and into the fluid containing chamber.

In at least one embodiment, the tissue wall is a myocardial wall of the heart.

In at least one embodiment, the tip is driven though the tissue wall at a location at or near the apex of the heart, and the chamber is the left ventricle.

In at least one embodiment, trocar is removed, the method further including hemostancally closing a tract left by insertion of the trocar through the opening through the tissue wall.

In at least one embodiment, the closing comprises: introducing a seal through the tract and into the chamber; retracting the seal against the tract opening and an inner surface of the tissue wall surrounding the tract opening, by retracting a suture attached to the seal and extending through the tract, through the opening through the skin and out of the patient; and advancing a clip over the suture and against an outer surface of the tissue wall to maintain tension on the suture, thereby maintaining the seal compressed against the inner surface.

In at least one embodiment, the closing comprises: introducing a seal through the tract and into the chamber;

retracting the seal against the tract opening and an inner surface of the tissue wall surrounding the tract opening, by retracting a suture attached to the seal and extending through the tract, through the opening through the skin and out of the patient; and advancing a suture loop over the suture and against an outer surface of the tissue wall, and cinching the suture loop against the outer surface of the tissue wall to maintain tension on the suture, thereby maintaining the seal compressed against the inner surface.

A method of hemostatically closing is provided, by minimally invasive procedures, a tract formed by insertion of a trocar through a tissue wall wherein an inside surface of the tissue wall interfaces with a fluid containing chamber, the method including the steps of inserting a seal through the trocar and into the chamber, the trocar having been inserted through a minimally invasive opening through the skin of a patient and through an opening in the tissue wall; retracting the trocar to remove it from the opening through the tissue wall; retracting the seal against the tract opening and an inner surface of the tissue wall surrounding the tract opening, by retracting a suture attached to the seal and extending through the tract, through the opening through the skin and out of the patient; and advancing a clip or suture loop over the suture and securing the clip or suture loop against an outer surface of the tissue wall to maintain tension on the suture, thereby maintaining the seal compressed against the inner surface.

Further provided is a method of hemostatically closing, by minimally invasive procedures, an opening where a cannula is placed through a tissue wall wherein an inside surface of the tissue wall interfaces with a fluid containing Chamber, the method including the steps of: delivering a closure assembly through the cannula and into the chamber, retracting the closure assembly to drive barbs of the closure assembly through the tissue wall in a direction from the inside surface to the outside surface; partially withdrawing the cannula to begin everting tissue edges defining the opening; completely withdrawing the cannula and sliding a locking ring on the closure assembly into a locked position to maintain the tissue edges everted and hemostatically sealing the opening.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An assembly configured to perform minimally-invasive ablation procedures, said assembly comprising:
    an elongated shaft;
    a balloon fitted over a distal end of said elongated shaft, said balloon being configured to assume a deflated configuration, as well as an inflated configuration wherein said balloon has an outside diameter greater than an outside diameter of said balloon in said deflated configuration;
    a halo comprising a plurality of electrically conducting wires configured to be positioned proximal of said balloon in a retracted configuration and movable to a position distal of said balloon in an expanded configuration suitable for tissue ablation, wherein, when in said expanded configuration, said halo defines an area larger than a contracted area defined by said halo when in said retracted configuration, and the wires ablate tissue surfaces contacting the wires when electrocautery current is delivered to the wires; and
    a plurality of push rods connected to the halo, wherein the push rods are axially slidable relative to the shaft to move the halo from the retracted configuration position and the deployed, expanded configuration position and vice versa, and wherein each push rod is connected to the halo.

2. The assembly of claim 1, wherein said halo is advanceable over said balloon when said balloon is in said inflated configuration.

3. The assembly of claim 1, wherein the wires are superelastic wires of the halo that expand a configuration of the halo when moving from said retracted configuration to said expanded configuration.

4. The assembly of claim 3, wherein said superelastic wires slide over said balloon and said balloon deforms somewhat as said halo passes from said retracted configuration to deploy over said balloon to said expanded configuration.

5. The assembly of claim 1., further comprising an actuator connected to proximal ends of said push rods, said actuator being slidable over said shaft.

6. The assembly of claim 5, wherein said actuator comprises an extension extending proximally to a proximal end portion of said shaft.

7. The assembly of claim 1, wherein said halo is connectable to a source of ablation energy proximal of said assembly.

8. The assembly of claim 1, further comprising a conduit connecting with said balloon and extending proximally of a proximal end of said shaft, said conduit being connectable in fluid communication with a source of pressurized fluid.

9. The assembly of claim 1, wherein said shaft comprises a cannula, said cannula being configured and dimensioned to receive an endoscope shaft therein, with a distal tip of said endoscope being positionable within said balloon.

10. The assembly of claim 1, wherein said shaft comprises a shaft of an endoscope.

11. The assembly of claim 1, wherein said halo is formed of two wires and forms a substantially oval shape when in said expanded configuration.

12. The assembly of claim 1, wherein said halo forms an encircling shape when in said expanded configuration.

13. The assembly of claim 1, wherein said halo is formed of four wires and forms a substantially quadrilateral shape when in said expanded configuration.

14. A viewing and ablation instrument configured to perform minimally-invasive ablation procedures, said instrument comprising:
    an elongated shaft;
    a balloon tip trocar comprising a balloon fitted over a distal end of said elongated shaft, said balloon being configured to assume a deflated configuration, as well as an inflated configuration wherein said balloon has an outside diameter greater than an outside diameter of said balloon in said deflated configuration; and
    a halo comprising a plurality of electrically conducting wires configured to be positioned proximal of said balloon in a retracted configuration and movable to a position distal of said balloon in an expanded configuration suitable for tissue ablation, wherein, when in said expanded configuration, said halo is configured to provide tissue surface ablation and said halo defines an area larger than a contracted area defined by said halo when in said retracted configuration and the wires ablate tissue surfaces contacting the wires when electrocautery current is delivered to the wires;

a plurality of push rods connected to the halo, wherein the push rods are axially slidable relative to the shaft to move the halo from the retracted configuration position and the deployed, expanded configuration position and vice versa, and wherein each push rod is connected to multiple wires of the plurality of wires; and an endoscope having a distal tip thereof positioned adjacent to an opening of said balloon or within said balloon.

15. The instrument of claim 14, wherein said shaft comprises a shaft of said endoscope.

16. The instrument of claim 14, wherein said shaft comprises a cannula and wherein a shaft of said endoscope is received in said cannula.

17. The instrument of claim 14, wherein said halo is advanceable over said balloon when said balloon is in said inflated configuration.

18. The instrument of claim 14, wherein the wires of said halo are electrically conducting superelastic wires that expand a configuration of said halo when moving from said retracted configuration to said expanded configuration.

19. The instrument of claim 18, wherein said superelastic wires slide over said balloon and said balloon deforms somewhat as said halo passes from said retracted configuration to deploy over said balloon to said expanded configuration.

20. The instrument of claim 14, wherein said halo provides tissue surface ablation when monopolar or bipolar electrocautery current is delivered to the electrically conducting wires of said halo.

21. An assembly configured to perform minimally-invasive ablation procedures, the assembly comprising:

an elongated shaft;

a balloon fitted over a distal end of the elongated shaft, wherein the balloon is configured to assume a deflated configuration, as well as an inflated configuration wherein the balloon has an outside diameter greater than an outside diameter of the balloon in the deflated configuration;

a halo comprising a plurality of electrically conducting superelastic wires configured to be positioned proximal of the balloon in a retracted configuration and movable to a position distal of the balloon in an expanded configuration suitable for tissue ablation, wherein, when in the expanded configuration, the halo defines an area larger than a contracted area defined by the halo when in the retracted configuration, and the wires ablate tissue surfaces contacting the wires when electrocautery current is delivered to the wires, wherein the superelastic wires elastically expand when moving from the retracted configuration to the expanded configuration, and wherein when the superelastic wires slide over the balloon as the halo passes from the retracted configuration to deploy over the balloon to the expanded configuration the balloon is deformed by the halo; and a plurality of push rods connected to the halo, wherein the push rods are axially slidable relative to the shaft to move the halo from the retracted configuration position and the deployed, expanded configuration position and vice versa, and wherein each push rod is connected to the halo.

22. The assembly of claim 21, wherein the electrically conducting superelastic wires are Nitinol wire having a diameter of about 0,012 inches to about 0.014 inches.

23. The assembly of claim 21, wherein the plurality of pushrods interconnect the halo and an actuator.

24. The assembly of claim 23, wherein each pushrod is connected to the halo via a connection point.

25. An assembly configured to perform minimally-invasive ablation procedures, said assembly comprising:

an elongated shaft;

a balloon fitted over a distal end of said elongated shaft, wherein the balloon is configured to assume a deflated configuration, as well as an inflated configuration wherein the balloon has an outside diameter greater than an outside diameter of the balloon in the deflated configuration; and a halo comprising a plurality of electrically conducting superelastic nickel-titanium alloy wires configured to be positioned proximal of the balloon in a retracted configuration and movable to a position distal of the balloon in an expanded configuration suitable for tissue ablation, wherein, when in the expanded configuration, said halo defines an area larger than a contracted area defined by the halo when in the retracted configuration, and the wires ablate tissue surfaces contacting the wires when electrocautery current is delivered to the wires; and a plurality of push rods connected to the halo, wherein the push rods are axially slidable relative to the shaft to move the halo from the retracted configuration position and the deployed, expanded configuration position and vice versa, and wherein each push rod is connected to two wires of the plurality of wires.

26. The assembly of claim 25, wherein the halo is formed of two wires providing a substantially oval shape when expanded.

27. The assembly of claim 25, wherein the halo is formed of four wires providing a quadrilateral configuration or diamond shape when expanded.

* * * * *